US009358287B2

(12) United States Patent
Harp et al.

(10) Patent No.: US 9,358,287 B2
(45) Date of Patent: *Jun. 7, 2016

(54) METHOD OF TREATING STRESS HYPERGLYCEMIA WITH HUMAN ANTIBODIES TO THE GLUCAGON RECEPTOR

(71) Applicant: Regeneron Pharmaceuticals, Inc., Tarrytown, NY (US)

(72) Inventors: Joyce Harp, White Plains, NY (US); Haruka Okamoto, Bronx, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/286,606

(22) Filed: May 23, 2014

(65) Prior Publication Data

US 2014/0255419 A1 Sep. 11, 2014

Related U.S. Application Data

(60) Division of application No. 13/900,275, filed on May 22, 2013, now Pat. No. 8,771,696, which is a continuation-in-part of application No. 13/301,944, filed on Nov. 22, 2011, now Pat. No. 8,545,847.

(60) Provisional application No. 61/416,409, filed on Nov. 23, 2010, provisional application No. 61/481,958, filed on May 3, 2011, provisional application No. 61/551,032, filed on Oct. 25, 2011, provisional application No. 61/650,966, filed on May 23, 2012, provisional application No. 61/787,748, filed on Mar. 15, 2013.

(51) Int. Cl.
| | |
|---|---|
| A61K 39/395 | (2006.01) |
| A61K 45/06 | (2006.01) |
| A61K 38/28 | (2006.01) |
| C07K 16/28 | (2006.01) |
| C07K 16/40 | (2006.01) |
| A61K 39/00 | (2006.01) |

(52) U.S. Cl.
CPC ............ *A61K 39/3955* (2013.01); *A61K 38/28* (2013.01); *A61K 39/39541* (2013.01); *A61K 45/06* (2013.01); *C07K 16/2869* (2013.01); *C07K 16/40* (2013.01); *A61K 2039/505* (2013.01); *A61K 2039/507* (2013.01); *C07K 2317/21* (2013.01); *C07K 2317/33* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,770,445 | A | 6/1998 | Kindsvogel et al. |
| 5,776,725 | A | 7/1998 | Kindsvogel et al. |
| 7,947,809 | B2 | 5/2011 | Yan et al. |
| 7,968,686 | B2 | 6/2011 | Korytko et al. |
| 8,088,731 | B2 | 1/2012 | Knudsen et al. |
| 8,158,759 | B2 | 4/2012 | Yan et al. |
| 8,545,847 | B2 | 10/2013 | Okamoto et al. |
| 2002/0106629 | A1 | 8/2002 | Murphy et al. |
| 2009/0041784 | A1 | 2/2009 | Yan et al. |
| 2011/0212092 | A1 | 9/2011 | Korytko et al. |
| 2011/0223160 | A1 | 9/2011 | Yan et al. |
| 2013/0251728 | A1 | 9/2013 | Harp et al. |

FOREIGN PATENT DOCUMENTS

| | | |
|---|---|---|
| WO | 2007/131237 A2 | 11/2007 |
| WO | 2008/036341 A2 | 3/2008 |
| WO | 2009/055783 A2 | 4/2009 |
| WO | 2012/071372 A2 | 5/2012 |

OTHER PUBLICATIONS

Bloom SR, et al., Q. J. Exp. Physiol. Cogn. Med. Sci., 58:99-108, 1973. Available online at—DOI: 10.1113/expphysiol.1973. sp002195.*
Jones BJ et al. Endocrinology, 153:1049-1054, 2012. Available online at—DOI: http://dx.doi.org/10.1210/en.2011-1979.*
Brand, et al., (1994) "Immunoneutralization of Endogenous Glucagon with Monoclonal Glucagon Antibody Normalizes Hyperglycaemia in Moderately Steptozotocin-diabetic Rats," Diabetologia, 37(10):985-993.
Buggy, et al., (1995) "Glucagon-Glucagon-Like Peptide 1 Receptor Chimeras Reveal Domains that Determine Specificity of Glucagon Binding," Journal Biological Chemistry, 270(13):7474-7478.
Buggy, et al., (1996) "Human Glucagon Receptor Monoclonal Antibodies: Antagonism of Glucagon Action and in Receptor Characterization," Hormone & Metabolic Research, 28(5):215-219.
Deane, et al., (2009) "The Effect of Exogenous Glucagon-Like Peptide-1 on the Glycaemic Response to Small Intestinal Nutrient in the Critically Ill: a Randomized Double-Blind Placebo-Controlled Cross Over Study," Critical Care, 13(3):R67.
Deane, et al., (2011) "Exogenous Glucagon-Like Peptide-1 Attenuates the Glycaemic Response to Postpyloric Nutrient Infustion in Critically Ill Patients with Type-2 Diabetes," Critical Care, 15(1):R35.

(Continued)

*Primary Examiner* — Robert Landsman
(74) *Attorney, Agent, or Firm* — Brownstein Hyatt Farber Schreck, LLP; Cara L. Crowley-Weber; Veronica Mallon

(57) ABSTRACT

The present invention provides antibodies that bind to the human glucagon receptor, designated GCGR and methods of using same. According to certain embodiments of the invention, the antibodies are fully human antibodies that bind to human GCGR. The antibodies of the invention are useful for lowering blood glucose levels and blood ketone levels and are also useful for the treatment of diseases and disorders associated with one or more GCGR biological activities, including the treatment of diabetes, diabetic ketoacidosis, long-term complications associated with diabetes, or other metabolic disorders characterized in part by elevated blood glucose levels, including stress hyperglycemia.

10 Claims, 9 Drawing Sheets

(56) References Cited

OTHER PUBLICATIONS

Kitabchi, et al., (Jul. 2009) "Hyperglycemic Crises in Adult Patients with Diabetes," Diabetes Care, 32:1335-1343.

Macneil, et al., (Jan. 14, 1994) "Cloning and Expression of a Human Glucagon Receptor," Biochemical and Biophysical Research Communications, 198(1):328-334.

Nauck, et al., (2004) "Blood Glucose Control in Health Subject and Patients Receiving Intravenous Glucose Infusion or Total Parenteral Nutrition Using Glucagon-Like Peptide 1," Science Direct, 118:89-97.

Rocha, et al., (Apr. 5, 1973) "Abnormal Pancreatic Alpha-Cell Function in Bacterial Infections," New England Journal of Medicine, 288(14):700-703.

Runge, et al., (2003) "Mechanisms of Signal Transduction: Three Distinct Epitopes on the Extracellular Face of the Glucagon Receptor Determine Specificity for the glucagon Amino Terminus," Journal Biological Chemistry, 278 (30):28005-28010.

The NICE-SUGAR Study Investigators, (Mar. 26, 2009) "Intensive versus Conventional Glucose Control in Critically Ill Patients," New England Journal of Medicine, 360(13):1283-1297.

Unson, et al., (1996) "Antibodies Against Specific Extracellular Epitopes of the Glucagon Receptor Block Glucagon Binding," Proc. Natl. Acad. Sci., 93(1):310-315.

Unson, et al., (2002) "Roles of Specific Extracellular Domains of the Glucagon Receptor in Ligand Binding and Signaling," Biochemistry, 41(39):11795-11803.

Van den Berghe, et al., (Nov. 8, 2001) "Intensive Insulin Therapy in Critically Ill Patients," New England Journal of Medicine, 345(19):1359-1367.

Van den Berghe, et al., (Nov. 2006) "Intensive Insulin Therapy in Mixed Medical/Surgical Intensive Care Units," Diabetes, 55:3151-3159.

Wright, et al., (2000) "Structure of Fab hGR-2 F6, a Competitive Antagonist of the Glucagon Receptor," Acta Cryst. D 56(5):573-580.

U.S. Appl. No. 14/014,517, filed Aug. 30, 2013.

International Search Report with respect to PCT/US2011/061766 mailed Nov. 8, 2012.

\* cited by examiner

```
                        SEQUENCE LISTING

<160> NUMBER OF SEQ ID NOS: 207

<210> SEQ ID NO 1
<211> LENGTH: 375
<212> TYPE: DNA
<213> ORGANISM: Artificial Sequence
<220> FEATURE:
<223> OTHER INFORMATION: Synthetic

<400> SEQUENCE: 1
caggtccagt tggtacagtc tggggctgac gtgaagaagc ctggggcctc agtgaaggtc      60
tcctgcaagg tttccggaca tatcctcact gatttatcca tgcactgggt gcgacagcct     120
cctggaaaag gacttgagtg gatggcaggt tttgatcctg aagaaggtaa aataatctac     180
gcacagaagt tccagggcag agtcaccatg accgaggaca tcctacaga cacagcctac      240 atggagctga gcagcctgag atctggggac acggccgttt attactgtgc aacaagcgat     300
attttgactg ggtattatag agactactac ggtttggacg tctggggcca agggaccacg     360
ctcaccgtct cctca                                                       375

<210> SEQ ID NO 2
<211> LENGTH: 125
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Gln Ser Gly Ala Asp Val Lys Lys Pro Gly Ala
 1               5                  10                  15

Ser Val Lys Val Ser Cys Lys Val Ser Gly His Ile Leu Thr Asp Leu
                20                  25                  30

Ser Met His Trp Val Arg Gln Pro Pro Gly Lys Gly Leu Glu Trp Met
            35                  40                  45

Ala Gly Phe Asp Pro Glu Glu Gly Lys Ile Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Gly Asp Thr Ala Val Tyr Tyr Cys
                85                  90                  95

Ala Thr Ser Asp Ile Leu Thr Gly Tyr Tyr Arg Asp Tyr Tyr Gly Leu
                100                 105                 110

Asp Val Trp Gly Gln Gly Thr Thr Leu Thr Val Ser Ser
        115                 120                 125

<210> SEQ ID NO 3
<211> LENGTH: 24
<212> TYPE: DNA
<213> ORGANISM: Artificial Sequence
<220> FEATURE:
<223> OTHER INFORMATION: Synthetic
```

```
<400> SEQUENCE: 3
ggacatatcc tcactgattt atcc                                          24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly His Ile Leu Thr Asp Leu Ser
 1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
tttgatcctg aagaaggtaa aata                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Phe Asp Pro Glu Glu Gly Lys Ile
 1               5

<210> SEQ ID NO 7
<211> LENGTH: 54
<212> TYPE: DNA
<213> ORGANISM: Artificial Sequence
<220> FEATURE:
<223> OTHER INFORMATION: Synthetic

<400> SEQUENCE: 7
gcaacaagcg atatttgac tgggtattat agagactact acggtttgga cgtc          54

<210> SEQ ID NO 8
<211> LENGTH: 18
<212> TYPE: PRT
<213> ORGANISM: Artificial Sequence
<220> FEATURE:
<223> OTHER INFORMATION: Synthetic

<400> SEQUENCE: 8

Ala Thr Ser Asp Ile Leu Thr Gly Tyr Tyr Arg Asp Tyr Tyr Gly Leu
 1               5                  10                  15

Asp Val

<210> SEQ ID NO 9
<211> LENGTH: 336
<212> TYPE: DNA
<213> ORGANISM: Artificial Sequence
<220> FEATURE:
<223> OTHER INFORMATION: Synthetic

<400> SEQUENCE: 9
```

```
gatattgtga tgactcagtc tccactcttc ctgcccgtca cccctggaga gccggcctcc    60
atctcctgca ggtctagtca gagcctcctg catagtaaag gatacaacta tttggattgg   120
tacctgcaga agccagggca gtctccacaa ctcctgatct atttgggttc taatcgggcc   180
tccggggtcc ctgacaggtt cagtggcagt ggatcaggca cagattttac actgaaaatc   240
agcagagtgg aggctgaaga tgttggggtt tattactgca tgcaaactct acaaactcct   300
cggacgttcg gccaagggac caaggtggaa atcaaa                             336
```

<210> SEQ ID NO 10
<211> LENGTH: 112
<212> TYPE: PRT
<213> ORGANISM: Artificial Sequence
<220> FEATURE:
<223> OTHER INFORMATION: Synthetic

<400> SEQUENCE: 10

Asp Ile Val Met Thr Gln Ser Pro Leu Phe Leu Pro Val Thr Pro Gly
1               5                   10                  15

Glu Pro Ala Ser Ile Ser Cys Arg Ser Ser Gln Ser Leu Leu His Ser
            20                  25                  30

Lys Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Arg Thr Phe Gly Gln Gly Thr Lys Val Glu Ile Lys
            100                 105                 110

<210> SEQ ID NO 11
<211> LENGTH: 33
<212> TYPE: DNA
<213> ORGANISM: Artificial Sequence
<220> FEATURE:
<223> OTHER INFORMATION: Synthetic

<400> SEQUENCE: 11
cagagcctcc tgcatagtaa aggatacaac tat                                 33

<210> SEQ ID NO 12
<211> LENGTH: 11
<212> TYPE: PRT
<213> ORGANISM: Artificial Sequence
<220> FEATURE:
<223> OTHER INFORMATION: Synthetic

<400> SEQUENCE: 12

Gln Ser Leu Leu His Ser Lys Gly Tyr Asn Tyr
1               5                   10

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 ttgggttct                                                                        9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Leu Gly Ser
 1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
atgcaaactc tacaaactcc tcggacg                                                   27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Met Gln Thr Leu Gln Thr Pro Arg Thr
 1               5

<210> SEQ ID NO 17
<211> LENGTH: 375
<212> TYPE: DNA
<213> ORGANISM: Artificial Sequence
<220> FEATURE:
<223> OTHER INFORMATION: Synthetic

<400> SEQUENCE: 17
caggtccagt tggtacagtc tggggctgac gtgaagaagc tggggcctc agtgaaggtc               60 tcctgcaagg tttccggaca tatcctcact gatttatcca tgcactgggt gcgacaggct             120
cctggaaaag ggcttgagtg gatgggaggt tttgatcctg aagaaggtga ataatctac              180 gcacagaagt tccagggcag agtcaccatg accgaggaca catctacaga cacagcctac             240
atggagctga gcagcctgag atctggggac acggccgttt attactgtgc aacaagcgat             300
attttgactg gttattatag agactactac ggtttggacg tctggggcca agggaccacg             360
ctcaccgtct cctca                                                              375

<210> SEQ ID NO 18
<211> LENGTH: 125
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Gln Ser Gly Ala Asp Val Lys Lys Pro Gly Ala
 1               5                  10                  15

Ser Val Lys Val Ser Cys Lys Val Ser Gly His Ile Leu Thr Asp Leu
             20                  25                  30

```
Ser Met His Trp Val Arg Gln Ala Pro Gly Lys Gly Leu Glu Trp Met
         35                  40                  45
Gly Gly Phe Asp Pro Glu Glu Gly Glu Ile Ile Tyr Ala Gln Lys Phe
     50                  55                  60
Gln Gly Arg Val Thr Met Thr Glu Asp Thr Ser Thr Asp Thr Ala Tyr
 65                  70                  75                  80
Met Glu Leu Ser Ser Leu Arg Ser Gly Asp Thr Ala Val Tyr Tyr Cys
                 85                  90                  95
Ala Thr Ser Asp Ile Leu Thr Gly Tyr Tyr Arg Asp Tyr Tyr Gly Leu
             100                 105                 110
Asp Val Trp Gly Gln Gly Thr Thr Leu Thr Val Ser Ser
        115                 120                 125

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggacatatcc tcactgattt atcc                                           24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly His Ile Leu Thr Asp Leu Ser
 1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
tttgatcctg aagaaggtga aata                                           24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Phe Asp Pro Glu Glu Gly Glu Ile
 1               5

<210> SEQ ID NO 23
<211> LENGTH: 54
<212> TYPE: DNA
<213> ORGANISM: Artificial Sequence
<220> FEATURE:
<223> OTHER INFORMATION: Synthetic

<400> SEQUENCE: 23
```

```
gcaacaagcg atattttgac tggttattat agagactact acggtttgga cgtc          54
```

<210> SEQ ID NO 24
<211> LENGTH: 18
<212> TYPE: PRT
<213> ORGANISM: Artificial Sequence
<220> FEATURE:
<223> OTHER INFORMATION: Synthetic

<400> SEQUENCE: 24

```
Ala Thr Ser Asp Ile Leu Thr Gly Tyr Tyr Arg Asp Tyr Tyr Gly Leu
 1               5                  10                  15

Asp Val
```

<210> SEQ ID NO 25
<211> LENGTH: 336
<212> TYPE: DNA
<213> ORGANISM: Artificial Sequence
<220> FEATURE:
<223> OTHER INFORMATION: Synthetic

<400> SEQUENCE: 25

```
gatattgtga tgactcagtc tccactcttc ctgcccgtca cccctggaga gccggcctcc    60
atctcctgca ggtctagtca gagcctcctg catagtaaag gatacaacta tttggattgg   120
tacctgcaga agccagggca gtctccacaa ctcctgatct atttgggttc taatcgggcc   180
tccggggtcc ctgacaggtt cagtggcagt ggatcaggca cagattttac actgaaaatc   240
agcagagtgg aggctgaaga tgttggggtt tattactgca tgcaaactct acaaactcct   300
cggacgttcg gccaagggac caaggtggaa atcaaa                             336
```

<210> SEQ ID NO 26
<211> LENGTH: 112
<212> TYPE: PRT
<213> ORGANISM: Artificial Sequence
<220> FEATURE:
<223> OTHER INFORMATION: Synthetic

<400> SEQUENCE: 26

```
Asp Ile Val Met Thr Gln Ser Pro Leu Phe Leu Pro Val Thr Pro Gly
 1               5                  10                  15

Glu Pro Ala Ser Ile Ser Cys Arg Ser Ser Gln Ser Leu Leu His Ser
            20                  25                  30

Lys Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Arg Thr Phe Gly Gln Gly Thr Lys Val Glu Ile Lys
            100                 105                 110
```

<210> SEQ ID NO 27
<211> LENGTH: 33
<212> TYPE: DNA
<213> ORGANISM: Artificial Sequence
<220> FEATURE:
<223> OTHER INFORMATION: Synthetic

<400> SEQUENCE: 27

```
cagagcctcc tgcatagtaa aggatacaac tat                                   33
```

<210> SEQ ID NO 28
<211> LENGTH: 11
<212> TYPE: PRT
<213> ORGANISM: Artificial Sequence
<220> FEATURE:
<223> OTHER INFORMATION: Synthetic

<400> SEQUENCE: 28

```
Gln Ser Leu Leu His Ser Lys Gly Tyr Asn Tyr
  1               5                  10
```

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29

```
ttgggttct                                                              9
```

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

```
Leu Gly Ser
  1
```

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31

```
atgcaaactc tacaaactcc tcggacg                                          27
```

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

```
Met Gln Thr Leu Gln Thr Pro Arg Thr
  1               5
```

<210> SEQ ID NO 33
<211> LENGTH: 372
<212> TYPE: DNA
<213> ORGANISM: Artificial Sequence
<220> FEATURE:
<223> OTHER INFORMATION: Synthetic

<400> SEQUENCE: 33

```
gaggagcaac tggtggagtc tgggggagac ttggtacagc ctggagggtc cctaagactc      60
tcctgtgcag cctctggatt cactctcagt agttatgaaa tgaactgggt ccgccaggct     120
```
ccagggaagg ggctggagtg ggtttcatac attagtagag gtggtagtct gatacactac    180
acagactctg tgaagggccg attcaccatc tccagagaca cgccaagaa ttcactgtat     240 ctgcaaatga acagcctgag agccgaggac acggctgttt attactgtgt gagagaccca    300
gcagctcgtt atcattatta ttatcacggt atggacgtct ggggccaagg gaccacggtc    360
accgtctcct ca                                                        372

<210> SEQ ID NO 34
<211> LENGTH: 124
<212> TYPE: PRT
<213> ORGANISM: Artificial Sequence
<220> FEATURE:
<223> OTHER INFORMATION: Synthetic

<400> SEQUENCE: 34

Glu Glu Gln Leu Val Glu Ser Gly Gly Asp Leu Val Gln Pro Gly Gly
 1               5                  10                  15

Ser Leu Arg Leu Ser Cys Ala Ala Ser Gly Phe Thr Leu Ser Ser Tyr
            20                  25                  30

Glu Met Asn Trp Val Arg Gln Ala Pro Gly Lys Gly Leu Glu Trp Val
        35                  40                  45

Ser Tyr Ile Ser Arg Gly Gly Ser Leu Ile His Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Pro Ala Ala Arg Tyr His Tyr Tyr Tyr His Gly Met Asp
            100                 105                 110

Val Trp Gly Gln Gly Thr Thr Val Thr Val Ser Ser
        115                 120

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcactc tcagtagtta tgaa                                            24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Leu Ser Ser Tyr Glu
 1               5

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37

```
attagtagag gtggtagtct gata                                           24
```

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

```
Ile Ser Arg Gly Gly Ser Leu Ile
 1               5
```

<210> SEQ ID NO 39
<211> LENGTH: 51
<212> TYPE: DNA
<213> ORGANISM: Artificial Sequence
<220> FEATURE:
<223> OTHER INFORMATION: Synthetic

<400> SEQUENCE: 39

```
gtgagagacc cagcagctcg ttatcattat tattatcacg gtatggacgt c            51
```

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

```
Val Arg Asp Pro Ala Ala Arg Tyr His Tyr Tyr Tyr His Gly Met Asp
 1               5                   10                  15
Val
```

<210> SEQ ID NO 41
<211> LENGTH: 336
<212> TYPE: DNA
<213> ORGANISM: Artificial Sequence
<220> FEATURE:
<223> OTHER INFORMATION: Synthetic

<400> SEQUENCE: 41

```
gatattgtga tgactcagtc tccactctcc ctgcccgtca cccctggaga gccggcctcc    60
atctcctgca ggtctagtca gagcctcctg cacaataatg gatataacta tttggattgg   120
tatctgcaga agccagggca gtctccacag ctcctgatct atttgggttc tagtcgggcc   180
tccggggtcc ctgacaggtt cagtggcagt ggatcaggca cagattttat actgaaaatc   240
agcagagtgg aggctgaaga tgttggggtt tattactgca tgcaagctct acaaactccg   300
tggacgttcg gccgagggac caaggtggaa atcaaa                             336
```

<210> SEQ ID NO 42
<211> LENGTH: 112
<212> TYPE: PRT
<213> ORGANISM: Artificial Sequence
<220> FEATURE:
<223> OTHER INFORMATION: Synthetic

<400> SEQUENCE: 42

```
Asp Ile Val Met Thr Gln Ser Pro Leu Ser Leu Pro Val Thr Pro Gly
 1               5                   10                  15

Glu Pro Ala Ser Ile Ser Cys Arg Ser Ser Gln Ser Leu Leu His Asn
```

```
                20                  25                  30
Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Ser Arg Ala Ser Gly Val Pro
        50                  55                  60

Asp Arg Phe Ser Gly Ser Gly Ser Gly Thr Asp Phe Ile Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Arg Gly Thr Lys Val Glu Ile Lys
            100                 105                 110
```

<210> SEQ ID NO 43
<211> LENGTH: 33
<212> TYPE: DNA
<213> ORGANISM: Artificial Sequence
<220> FEATURE:
<223> OTHER INFORMATION: Synthetic

<400> SEQUENCE: 43
cagagcctcc tgcacaataa tggatataac tat                                33

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

```
Gln Ser Leu Leu His Asn Asn Gly Tyr Asn Tyr
1               5                   10
```

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 ttgggttct                                                            9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

```
Leu Gly Ser
 1
```

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
atgcaagctc tacaaactcc gtggacg                                       27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Met Gln Ala Leu Gln Thr Pro Trp Thr
 1               5

<210> SEQ ID NO 49
<211> LENGTH: 384
<212> TYPE: DNA
<213> ORGANISM: Artificial Sequence
<220> FEATURE:
<223> OTHER INFORMATION: Synthetic

<400> SEQUENCE: 49
gaggtgcagc tggtggagtc tgggggaggc gtggtccagc ctggagggtc cctgagactc      60
tcctgtgcag cctctggatt caccttcagt agttatgaca tgcactgggt ccgccaggct     120
ccaggcaagg ggctggagtg ggtggcagtt atatcatctg atggacgtga taaatactat     180
gtagactccg tgaagggccg attcaccatc tccagagaca actccaagaa cacgctttat     240
ctgcaaatga acagcctgag agctgaggac acggctgttt attactgtgc gaaagagatg     300
gtgtattacg atattttgac tggttatcat aactactacg gtatggacgt ctggggccaa     360
gggaccacgg tcaccgtctc ctca                                            384

<210> SEQ ID NO 50
<211> LENGTH: 128
<212> TYPE: PRT
<213> ORGANISM: Artificial Sequence
<220> FEATURE:
<223> OTHER INFORMATION: Synthetic

<400> SEQUENCE: 50

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Asp Met His Trp Val Arg Gln Ala Pro Gly Lys Gly Leu Glu Trp Val
            35                  40                  45

Ala Val Ile Ser Ser Asp Gly Arg Asp Lys Tyr Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Met Val Tyr Tyr Asp Ile Leu Thr Gly Tyr His Asn Tyr
            100                 105                 110

Tyr Gly Met Asp Val Trp Gly Gln Gly Thr Thr Val Thr Val Ser Ser
        115                 120                 125

<210> SEQ ID NO 51
<211> LENGTH: 24
<212> TYPE: DNA
<213> ORGANISM: Artificial Sequence
<220> FEATURE:
<223> OTHER INFORMATION: Synthetic

```
<400> SEQUENCE: 51
ggattcacct tcagtagtta tgac                                          24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Ser Tyr Asp
 1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
atatcatctg atggacgtga taaa                                          24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Ser Asp Gly Arg Asp Lys
 1               5

<210> SEQ ID NO 55
<211> LENGTH: 63
<212> TYPE: DNA
<213> ORGANISM: Artificial Sequence
<220> FEATURE:
<223> OTHER INFORMATION: Synthetic

<400> SEQUENCE: 55
gcgaaagaga tggtgtatta cgatattttg actggttatc ataactacta cggtatggac   60
gtc                                                                 63

<210> SEQ ID NO 56
<211> LENGTH: 21
<212> TYPE: PRT
<213> ORGANISM: Artificial Sequence
<220> FEATURE:
<223> OTHER INFORMATION: Synthetic

<400> SEQUENCE: 56

Ala Lys Glu Met Val Tyr Tyr Asp Ile Leu Thr Gly Tyr His Asn Tyr
 1               5                  10                  15

Tyr Gly Met Asp Val
            20

<210> SEQ ID NO 57
<211> LENGTH: 324
<212> TYPE: DNA
<213> ORGANISM: Artificial Sequence
<220> FEATURE:
<223> OTHER INFORMATION: Synthetic
```

<400> SEQUENCE: 57

```
gacatcgtga tgacccagtc tccatcctca ctgtctgcat ctgtaggaga cagagtcacc    60
atcacttgtc gggcgagtca gggcattaac aattatttag cctggtttca gcagaaacca   120
gggaaagccc ctaagtccct gatccatact gcatccagtt tgcaaagtgg ggtcccatca   180
aagttcagcg gcagtggatc tgggacagat ttcactctca ccatcagcag cctgcagcct   240
gaagattttg caacttatta ctgccaacag tataatactt accctctcac tttcggcgga   300
gggaccaaag tggagatcaa acga                                          324
```

<210> SEQ ID NO 58
<211> LENGTH: 108
<212> TYPE: PRT
<213> ORGANISM: Artificial Sequence
<220> FEATURE:
<223> OTHER INFORMATION: Synthetic

<400> SEQUENCE: 58

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Phe Gln Gln Lys Pro Gly Lys Ala Pro Lys Ser Leu Ile
        35                  40                  45

His Thr Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Leu
                85                  90                  95

Thr Phe Gly Gly Gly Thr Lys Val Glu Ile Lys Arg
            100                 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59

```
cagggcatta acaattat                                                  18
```

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Gly Ile Asn Asn Tyr
1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

```
<400> SEQUENCE: 61 actgcatcc                                                            9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Thr Ala Ser
  1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caacagtata atacttaccc tctcact                                       27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Tyr Asn Thr Tyr Pro Leu Thr
  1               5

<210> SEQ ID NO 65
<211> LENGTH: 381
<212> TYPE: DNA
<213> ORGANISM: Artificial Sequence
<220> FEATURE:
<223> OTHER INFORMATION: Synthetic

<400> SEQUENCE: 65
caggtgcagc tggtggagtc tgggggaggc gtggtccagc ctgggaggtc cctgagactc    60
tcctgtgcag cctctggatt caccttcagt agttatgaca tgcactgggt ccgccaggct   120
ccaggcaagg ggctggagtg ggtggcagtt atatcatctg atggacgtga taaatactat   180
gtagactccg tgaagggccg attcaccatc tccagagaca actccaagaa cacgctttat   240
ctgcaaatga acagcctgag agctgaggac acggctgttt attactgtgc gaaagagatg   300
gtgtattacg atattttgac tggttatcat aactactacg gtatggacgt ctggggccaa   360
gggaccacgg tcaccgtctc c                                            381

<210> SEQ ID NO 66
<211> LENGTH: 127
<212> TYPE: PRT
<213> ORGANISM: Artificial Sequence
<220> FEATURE:
<223> OTHER INFORMATION: Synthetic

<400> SEQUENCE: 66

Gln Val Gln Leu Val Glu Ser Gly Gly Gly Val Val Gln Pro Gly Arg
  1               5                  10                  15
```

```
Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Ser Ser Asp Gly Arg Asp Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Met Val Tyr Tyr Asp Ile Leu Thr Gly Tyr His Asn Tyr
            100                 105                 110

Tyr Gly Met Asp Val Trp Gly Gln Gly Thr Thr Val Thr Val Ser
        115                 120                 125

<210> SEQ ID NO 67
<211> LENGTH: 321
<212> TYPE: DNA
<213> ORGANISM: Artificial Sequence
<220> FEATURE:
<223> OTHER INFORMATION: Synthetic

<400> SEQUENCE: 67
gacatccaga tgacccagtc tccatcctca ctgtctgcat ctgtaggaga cagagtcacc      60
atcacttgtc gggcgagtca gggcattaac aattatttag cctggtttca gcagaaacca    120
gggaaagccc ctaagtccct gatccatact gcatccagtt tgcaaagtgg ggtcccatca    180
aagttcagcg gcagtggatc tgggacagat ttcactctca ccatcagcag cctgcagcct    240
gaagattttg caacttatta ctgccaacag tataatactt accctctcac tttcggcgga    300
gggaccaagg tggagatcaa a                                              321

<210> SEQ ID NO 68
<211> LENGTH: 107
<212> TYPE: PRT
<213> ORGANISM: Artificial Sequence
<220> FEATURE:
<223> OTHER INFORMATION: Synthetic

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Phe Gln Gln Lys Pro Gly Lys Ala Pro Lys Ser Leu Ile
        35                  40                  45

His Thr Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Leu
                85                  90                  95

Thr Phe Gly Gly Gly Thr Lys Val Glu Ile Lys
            100                 105

<210> SEQ ID NO 69
<211> LENGTH: 384
<212> TYPE: DNA
<213> ORGANISM: Artificial Sequence
```

-continued

<220> FEATURE:
<223> OTHER INFORMATION: Synthetic

<400> SEQUENCE: 69
caggtgcagc tggtgcagtc tgggggaggc ttggtccagc ctgggggtc cctgagactc      60 tcctgtgcag cctccggatt cacctttagt aactatttga tgaactgggt ccgccaggct    120
ccagggaagg gctggagtg gctggccaac atacaggaag atggaattga gaaatactat    180
gtggactctg tgaagggccg attcaccatc tccagagaca acgccaagaa ctcactgtat    240
ctgcaaatga acagcctgag agccgaggac acggctgtgt attactgtgc gagagagccc    300
tcccattacg atattttgac tggttatgac tactattacg gtatggacgt ctggggccaa    360
gggaccacgg tcaccgtctc ctca                                            384

<210> SEQ ID NO 70
<211> LENGTH: 128
<212> TYPE: PRT
<213> ORGANISM: Artificial Sequence
<220> FEATURE:
<223> OTHER INFORMATION: Synthetic

<400> SEQUENCE: 70

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Leu Met Asn Trp Val Arg Gln Ala Pro Gly Lys Gly Leu Glu Trp Leu
        35                  40                  45

Ala Asn Ile Gln Glu Asp Gly Ile Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Ser His Tyr Asp Ile Leu Thr Gly Tyr Asp Tyr Tyr
            100                 105                 110

Tyr Gly Met Asp Val Trp Gly Gln Gly Thr Thr Val Thr Val Ser Ser
        115                 120                 125

<210> SEQ ID NO 71
<211> LENGTH: 24
<212> TYPE: DNA
<213> ORGANISM: Artificial Sequence
<220> FEATURE:
<223> OTHER INFORMATION: Synthetic

<400> SEQUENCE: 71
ggattcacct ttagtaacta tttg                                            24

<210> SEQ ID NO 72
<211> LENGTH: 8
<212> TYPE: PRT
<213> ORGANISM: Artificial Sequence
<220> FEATURE:
<223> OTHER INFORMATION: Synthetic

<400> SEQUENCE: 72

Gly Phe Thr Phe Ser Asn Tyr Leu
1               5

```
<210> SEQ ID NO 73
<211> LENGTH: 24
<212> TYPE: DNA
<213> ORGANISM: Artificial Sequence
<220> FEATURE:
<223> OTHER INFORMATION: Synthetic

<400> SEQUENCE: 73
atacaggaag atggaattga gaaa                                           24

<210> SEQ ID NO 74
<211> LENGTH: 8
<212> TYPE: PRT
<213> ORGANISM: Artificial Sequence
<220> FEATURE:
<223> OTHER INFORMATION: Synthetic

<400> SEQUENCE: 74

Ile Gln Glu Asp Gly Ile Glu Lys
 1               5

<210> SEQ ID NO 75
<211> LENGTH: 63
<212> TYPE: DNA
<213> ORGANISM: Artificial Sequence
<220> FEATURE:
<223> OTHER INFORMATION: Synthetic

<400> SEQUENCE: 75
gcgagagagc cctcccatta cgatattttg actggttatg actactatta cggtatggac    60
gtc                                                                  63

<210> SEQ ID NO 76
<211> LENGTH: 21
<212> TYPE: PRT
<213> ORGANISM: Artificial Sequence
<220> FEATURE:
<223> OTHER INFORMATION: Synthetic

<400> SEQUENCE: 76

Ala Arg Glu Pro Ser His Tyr Asp Ile Leu Thr Gly Tyr Tyr Tyr Tyr
 1               5                  10                  15

Tyr Gly Met Asp Val
            20

<210> SEQ ID NO 77
<211> LENGTH: 324
<212> TYPE: DNA
<213> ORGANISM: Artificial Sequence
<220> FEATURE:
<223> OTHER INFORMATION: Synthetic

<400> SEQUENCE: 77
gacatccagt tgacccagtc tccatcctcc ctgtctgcat ctgtaggaga cagagtcacc    60
atcacttgcc gggcaagtca gggcattaga aatgatttag ctggtatca gcagaaacca   120 gggaaagccc ctaagcgcct gatctatgct gcatccagtt tgcaaagtgg ggtcccatca   180
aggttcagcg gcagtggatc tgggacagaa ttcattctca cagtcagcag cctgcagcct   240
gaagactttg caacttatta ctgtctacag tataatagta acccattcac tttcggccct   300
gggaccaagg tggagatcaa acga                                         324

<210> SEQ ID NO 78
<211> LENGTH: 108
```

```
<212> TYPE: PRT
<213> ORGANISM: Artificial Sequence
<220> FEATURE:
<223> OTHER INFORMATION: Synthetic

<400> SEQUENCE: 78

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Ile Leu Thr Val Ser Ser Leu Gln Pro
65                  70                  75                  80

Glu Asp Phe Ala Thr Tyr Tyr Cys Leu Gln Tyr Asn Ser Asn Pro Phe
                85                  90                  95

Thr Phe Gly Pro Gly Thr Lys Val Glu Ile Lys Arg
            100                 105

<210> SEQ ID NO 79
<211> LENGTH: 18
<212> TYPE: DNA
<213> ORGANISM: Artificial Sequence
<220> FEATURE:
<223> OTHER INFORMATION: Synthetic

<400> SEQUENCE: 79
cagggcatta gaaatgat                                                  18

<210> SEQ ID NO 80
<211> LENGTH: 6
<212> TYPE: PRT
<213> ORGANISM: Artificial Sequence
<220> FEATURE:
<223> OTHER INFORMATION: Synthetic

<400> SEQUENCE: 80

Gln Gly Ile Arg Asn Asp
1               5

<210> SEQ ID NO 81
<211> LENGTH: 9
<212> TYPE: DNA
<213> ORGANISM: Artificial Sequence
<220> FEATURE:
<223> OTHER INFORMATION: Synthetic

<400> SEQUENCE: 81 gctgcatcc                                                             9

<210> SEQ ID NO 82
<211> LENGTH: 3
<212> TYPE: PRT
<213> ORGANISM: Artificial Sequence
<220> FEATURE:
<223> OTHER INFORMATION: Synthetic

<400> SEQUENCE: 82

Ala Ala Ser
1
```

<210> SEQ ID NO 83
<211> LENGTH: 27
<212> TYPE: DNA
<213> ORGANISM: Artificial Sequence
<220> FEATURE:
<223> OTHER INFORMATION: Synthetic

<400> SEQUENCE: 83
ctacagtata atagtaaccc attcact                                27

<210> SEQ ID NO 84
<211> LENGTH: 9
<212> TYPE: PRT
<213> ORGANISM: Artificial Sequence
<220> FEATURE:
<223> OTHER INFORMATION: Synthetic

<400> SEQUENCE: 84

Leu Gln Tyr Asn Ser Asn Pro Phe Thr
 1               5

<210> SEQ ID NO 85
<211> LENGTH: 381
<212> TYPE: DNA
<213> ORGANISM: Artificial Sequence
<220> FEATURE:
<223> OTHER INFORMATION: Synthetic

<400> SEQUENCE: 85
gaggtgcagc tggtggagtc tgggggaggc ttggtccagc ctggggggtc cctgagactc      60
tcctgtgcag cctccggatt cacctttagt aactatttga tgaactgggt ccgccaggct     120
ccagggaagg ggctggagtg gctggccaac atacaggaag atggaattga aaatactat     180 gtggactctg tgaagggccg attcaccatc tccagagaca acgccaagaa ctcactgtat     240
ctgcaaatga acagcctgag agccgaggac acggctgtgt attactgtgc gagagagccc     300
tcccattacg atatttgac tggttatgac tactattacg gtatggacgt ctggggccaa     360
gggaccacgg tcaccgtctc c                                              381

<210> SEQ ID NO 86
<211> LENGTH: 127
<212> TYPE: PRT
<213> ORGANISM: Artificial Sequence
<220> FEATURE:
<223> OTHER INFORMATION: Synthetic

<400> SEQUENCE: 86

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Leu Met Asn Trp Val Arg Gln Ala Pro Gly Lys Gly Leu Glu Trp Leu
        35                  40                  45

Ala Asn Ile Gln Glu Asp Gly Ile Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Ser His Tyr Asp Ile Leu Thr Gly Tyr Asp Tyr Tyr
            100                 105                 110

Tyr Gly Met Asp Val Trp Gly Gln Gly Thr Thr Val Thr Val Ser
    115                 120                 125

<210> SEQ ID NO 87
<211> LENGTH: 321
<212> TYPE: DNA
<213> ORGANISM: Artificial Sequence
<220> FEATURE:
<223> OTHER INFORMATION: Synthetic

<400> SEQUENCE: 87
gacatccaga tgacccagtc tccatcctcc ctgtctgcat ctgtaggaga cagagtcacc    60
atcacttgcc gggcaagtca gggcattaga aatgatttag ctggtatca gcagaaacca   120
gggaaagccc ctaagcgcct gatctatgct gcatccagtt tgcaaagtgg ggtcccatca   180
aggttcagcg gcagtggatc tgggacagaa ttcattctca cagtcagcag cctgcagcct   240
gaagactttg caacttatta ctgtctacag tataatagta acccattcac tttcggccct   300
gggaccaaag tggatatcaa a                                             321

<210> SEQ ID NO 88
<211> LENGTH: 107
<212> TYPE: PRT
<213> ORGANISM: Artificial Sequence
<220> FEATURE:
<223> OTHER INFORMATION: Synthetic

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Ile Leu Thr Val Ser Ser Leu Gln Pro
65                  70                  75                  80

Glu Asp Phe Ala Thr Tyr Tyr Cys Leu Gln Tyr Asn Ser Asn Pro Phe
                85                  90                  95

Thr Phe Gly Pro Gly Thr Lys Val Asp Ile Lys
            100                 105

<210> SEQ ID NO 89
<211> LENGTH: 381
<212> TYPE: DNA
<213> ORGANISM: Artificial Sequence
<220> FEATURE:
<223> OTHER INFORMATION: Synthetic

<400> SEQUENCE: 89
gaggtgcagc tggtgcagtc tgggggagcc ttggtacagc ctgggggtc cctgagactc    60
tcctgtacag cctctggttt caccttcagt aactacgaca tgcactgggt ccgccaaact   120
acaggaaaag gtctggagtg gatctcagct attgatactg ctggtgacac atactatcca   180
ggctccgtga agggccgatt caccgtctcc agagaaaatg ccaagaactc ctttatctt   240
caaatgaaca gcctgagagc cggggacacg gctgtgtatt actgtgcaag ggaggggaag   300
tattacgata ttttgactgg tgactaccac tactacggta tggacgtctg ggccaaggg   360
accacggtca ccgtctcctc a                                             381

<210> SEQ ID NO 90
<211> LENGTH: 127
<212> TYPE: PRT
<213> ORGANISM: Artificial Sequence
<220> FEATURE:
<223> OTHER INFORMATION: Synthetic

<400> SEQUENCE: 90

Glu Val Gln Leu Val Gln Ser Gly Gly Ala Leu Val Gln Pro Gly Gly
1               5                   10                  15

Ser Leu Arg Leu Ser Cys Thr Ala Ser Gly Phe Thr Phe Ser Asn Tyr
            20                  25                  30

Asp Met His Trp Val Arg Gln Thr Thr Gly Lys Gly Leu Glu Trp Ile
        35                  40                  45

Ser Ala Ile Asp Thr Ala Gly Asp Thr Tyr Tyr Pro Gly Ser Val Lys
    50                  55                  60

Gly Arg Phe Thr Val Ser Arg Glu Asn Ala Lys Asn Ser Phe Tyr Leu
65                  70                  75                  80

Gln Met Asn Ser Leu Arg Ala Gly Asp Thr Ala Val Tyr Tyr Cys Ala
                85                  90                  95

Arg Glu Gly Lys Tyr Tyr Asp Ile Leu Thr Gly Asp Tyr His Tyr Tyr
            100                 105                 110

Gly Met Asp Val Trp Gly Gln Gly Thr Thr Val Thr Val Ser Ser
        115                 120                 125

<210> SEQ ID NO 91
<211> LENGTH: 24
<212> TYPE: DNA
<213> ORGANISM: Artificial Sequence
<220> FEATURE:
<223> OTHER INFORMATION: Synthetic

<400> SEQUENCE: 91
ggtttcacct tcagtaacta cgac                                          24

<210> SEQ ID NO 92
<211> LENGTH: 8
<212> TYPE: PRT
<213> ORGANISM: Artificial Sequence
<220> FEATURE:
<223> OTHER INFORMATION: Synthetic

<400> SEQUENCE: 92

Gly Phe Thr Phe Ser Asn Tyr Asp
1               5

<210> SEQ ID NO 93
<211> LENGTH: 21
<212> TYPE: DNA
<213> ORGANISM: Artificial Sequence
<220> FEATURE:
<223> OTHER INFORMATION: Synthetic

<400> SEQUENCE: 93
attgatactg ctggtgacac a                                             21

<210> SEQ ID NO 94
<211> LENGTH: 7
<212> TYPE: PRT
<213> ORGANISM: Artificial Sequence
<220> FEATURE:
<223> OTHER INFORMATION: Synthetic

<400> SEQUENCE: 94

Ile Asp Thr Ala Gly Asp Thr
1               5

<210> SEQ ID NO 95
<211> LENGTH: 63
<212> TYPE: DNA
<213> ORGANISM: Artificial Sequence
<220> FEATURE:
<223> OTHER INFORMATION: Synthetic

<400> SEQUENCE: 95
gcaagggagg ggaagtatta cgatattttg actggtgact accactacta cggtatggac    60
gtc                                                                 63

<210> SEQ ID NO 96
<211> LENGTH: 21
<212> TYPE: PRT
<213> ORGANISM: Artificial Sequence
<220> FEATURE:
<223> OTHER INFORMATION: Synthetic

<400> SEQUENCE: 96

Ala Arg Glu Gly Lys Tyr Tyr Asp Ile Leu Thr Gly Asp Tyr His Tyr
1               5                   10                  15

Tyr Gly Met Asp Val
            20

<210> SEQ ID NO 97
<211> LENGTH: 324
<212> TYPE: DNA
<213> ORGANISM: Artificial Sequence
<220> FEATURE:
<223> OTHER INFORMATION: Synthetic

<400> SEQUENCE: 97
gccatccgga tgacccagtc tccatcctcc ctgtctgcat ctgtaggaga cagagtcacc    60
atcacttgtc gggcaagtca gggcattaga aatgatttag ctggtatca gcagaaacca   120 gggaaagccc ctaagcgact gatctatgct acatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgctcac tttcggcgga   300
gggaccaagg tggaaatcaa acga                                          324

<210> SEQ ID NO 98
<211> LENGTH: 108
<212> TYPE: PRT
<213> ORGANISM: Artificial Sequence
<220> FEATURE:
<223> OTHER INFORMATION: Synthetic

<400> SEQUENCE: 98

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys Arg
            100                 105

<210> SEQ ID NO 99
<211> LENGTH: 18
<212> TYPE: DNA
<213> ORGANISM: Artificial Sequence
<220> FEATURE:
<223> OTHER INFORMATION: Synthetic

<400> SEQUENCE: 99
cagggcatta gaaatgat                                                 18

<210> SEQ ID NO 100
<211> LENGTH: 6
<212> TYPE: PRT
<213> ORGANISM: Artificial Sequence
<220> FEATURE:
<223> OTHER INFORMATION: Synthetic

<400> SEQUENCE: 100

Gln Gly Ile Arg Asn Asp
1               5

<210> SEQ ID NO 101
<211> LENGTH: 9
<212> TYPE: DNA
<213> ORGANISM: Artificial Sequence
<220> FEATURE:
<223> OTHER INFORMATION: Synthetic

<400> SEQUENCE: 101 gctacatcc                                                            9

<210> SEQ ID NO 102
<211> LENGTH: 3
<212> TYPE: PRT
<213> ORGANISM: Artificial Sequence
<220> FEATURE:
<223> OTHER INFORMATION: Synthetic

<400> SEQUENCE: 102

Ala Thr Ser
1

<210> SEQ ID NO 103
<211> LENGTH: 27
<212> TYPE: DNA
<213> ORGANISM: Artificial Sequence
<220> FEATURE:
<223> OTHER INFORMATION: Synthetic

<400> SEQUENCE: 103
ctacagcata atagttaccc gctcact                                       27

<210> SEQ ID NO 104
<211> LENGTH: 9
<212> TYPE: PRT
<213> ORGANISM: Artificial Sequence
<220> FEATURE:
<223> OTHER INFORMATION: Synthetic -continued

<400> SEQUENCE: 104

Leu Gln His Asn Ser Tyr Pro Leu Thr
 1               5

<210> SEQ ID NO 105
<211> LENGTH: 378
<212> TYPE: DNA
<213> ORGANISM: Artificial Sequence
<220> FEATURE:
<223> OTHER INFORMATION: Synthetic

<400> SEQUENCE: 105
gaggtgcagc tggtggagtc tgggggagcc ttggtacagc ctggggggtc cctgagactc     60
tcctgtacag cctctggttt caccttcagt aactacgaca tgcactgggt ccgccaaact    120
acaggaaaag gtctggagtg gatctcagct attgatactg ctggtgacac atactatcca    180
ggctccgtga agggccgatt caccgtctcc agagaaaatg ccaagaactc ctttttatctt    240 caaatgaaca gcctgagagc cggggacacg gctgtgtatt actgtgcaag ggaggggaag    300
tattacgata ttttgactgg tgactaccac tactacggta tggacgtctg ggggccaaggg    360 accacggtca ccgtctcc                                                  378

<210> SEQ ID NO 106
<211> LENGTH: 126
<212> TYPE: PRT
<213> ORGANISM: Artificial Sequence
<220> FEATURE:
<223> OTHER INFORMATION: Synthetic

<400> SEQUENCE: 106

Glu Val Gln Leu Val Glu Ser Gly Gly Ala Leu Val Gln Pro Gly Gly
 1               5                  10                  15

Ser Leu Arg Leu Ser Cys Thr Ala Ser Gly Phe Thr Phe Ser Asn Tyr
             20                  25                  30

Asp Met His Trp Val Arg Gln Thr Thr Gly Lys Gly Leu Glu Trp Ile
         35                  40                  45

Ser Ala Ile Asp Thr Ala Gly Asp Thr Tyr Tyr Pro Gly Ser Val Lys
     50                  55                  60

Gly Arg Phe Thr Val Ser Arg Glu Asn Ala Lys Asn Ser Phe Tyr Leu
 65                  70                  75                  80

Gln Met Asn Ser Leu Arg Ala Gly Asp Thr Ala Val Tyr Tyr Cys Ala
                 85                  90                  95

Arg Glu Gly Lys Tyr Tyr Asp Ile Leu Thr Gly Asp Tyr His Tyr Tyr
            100                 105                 110

Gly Met Asp Val Trp Gly Gln Gly Thr Thr Val Thr Val Ser
        115                 120                 125

<210> SEQ ID NO 107
<211> LENGTH: 321
<212> TYPE: DNA
<213> ORGANISM: Artificial Sequence
<220> FEATURE:
<223> OTHER INFORMATION: Synthetic

<400> SEQUENCE: 107
gacatccaga tgacccagtc tccatcctcc ctgtctgcat ctgtaggaga cagagtcacc     60
atcacttgtc gggcaagtca gggcattaga aatgatttag ctggtatca gcagaaacca    120 gggaaagccc ctaagcgact gatctatgct acatccagtt tgcaaagtgg ggtcccatca    180

```
aggttcagcg gcagtggatc tgggacagaa ttcactctca caatcagcag cctgcagcct    240
gaagattttg caacttatta ctgtctacag cataatagtt acccgctcac tttcggcgga    300
gggaccaagc tggagatcaa a                                              321
```

<210> SEQ ID NO 108
<211> LENGTH: 107
<212> TYPE: PRT
<213> ORGANISM: Artificial Sequence
<220> FEATURE:
<223> OTHER INFORMATION: Synthetic

<400> SEQUENCE: 108

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Thr Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Leu Glu Ile Lys
            100                 105
```

<210> SEQ ID NO 109
<211> LENGTH: 372
<212> TYPE: DNA
<213> ORGANISM: Artificial Sequence
<220> FEATURE:
<223> OTHER INFORMATION: Synthetic

<400> SEQUENCE: 109

```
caggtgcagc tggtgcagtc tgggggaggc gtggtccagc ctgggaggtc cctgagactc    60
tcctgtgcag cgtctggggtt cacctttagt aactttggca tgcactgggt ccgccaggct   120
ccaggcaagg ggctggagtg ggtggcagtt atatggtttg atgaaattga taaatactat   180
gcagactccg tgaagggccg attcaccatc tccagagaca attccaagaa cacgctgtat   240
ccgcaaatga acagcctgag agccgaagac acggctgtgt attactgtgc gcgagaagat   300
tacgatattt tgactggtta ctattacgct atggacgtct ggggccaagg gaccacggtc   360
accgtctcct ca                                                        372
```

<210> SEQ ID NO 110
<211> LENGTH: 124
<212> TYPE: PRT
<213> ORGANISM: Artificial Sequence
<220> FEATURE:
<223> OTHER INFORMATION: Synthetic

<400> SEQUENCE: 110

```
Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
```

```
                35                  40                  45
Ala Val Ile Trp Phe Asp Glu Ile Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Pro Gln Met Asn Ser Leu Arg Ala Glu Asp Thr Ala Val Tyr Tyr Cys
                85                  90                  95

Ala Arg Glu Asp Tyr Asp Ile Leu Thr Gly Tyr Tyr Ala Met Asp
            100                 105                 110

Val Trp Gly Gln Gly Thr Thr Val Thr Val Ser Ser
        115                 120
```

<210> SEQ ID NO 111
<211> LENGTH: 24
<212> TYPE: DNA
<213> ORGANISM: Artificial Sequence
<220> FEATURE:
<223> OTHER INFORMATION: Synthetic

<400> SEQUENCE: 111
gggttcacct ttagtaactt tggc                                          24

<210> SEQ ID NO 112
<211> LENGTH: 8
<212> TYPE: PRT
<213> ORGANISM: Artificial Sequence
<220> FEATURE:
<223> OTHER INFORMATION: Synthetic

<400> SEQUENCE: 112

```
Gly Phe Thr Phe Ser Asn Phe Gly
 1               5
```

<210> SEQ ID NO 113
<211> LENGTH: 24
<212> TYPE: DNA
<213> ORGANISM: Artificial Sequence
<220> FEATURE:
<223> OTHER INFORMATION: Synthetic

<400> SEQUENCE: 113
atatggtttg atgaaattga taaa                                          24

<210> SEQ ID NO 114
<211> LENGTH: 8
<212> TYPE: PRT
<213> ORGANISM: Artificial Sequence
<220> FEATURE:
<223> OTHER INFORMATION: Synthetic

<400> SEQUENCE: 114

```
Ile Trp Phe Asp Glu Ile Asp Lys
 1               5
```

<210> SEQ ID NO 115
<211> LENGTH: 51
<212> TYPE: DNA
<213> ORGANISM: Artificial Sequence
<220> FEATURE:
<223> OTHER INFORMATION: Synthetic

<400> SEQUENCE: 115
gcgcgagaag attacgatat tttgactggt tactattacg ctatggacgt c            51

<210> SEQ ID NO 116
<211> LENGTH: 17
<212> TYPE: PRT
<213> ORGANISM: Artificial Sequence
<220> FEATURE:
<223> OTHER INFORMATION: Synthetic

<400> SEQUENCE: 116

Ala Arg Glu Asp Tyr Asp Ile Leu Thr Gly Tyr Tyr Ala Met Asp
1               5                   10                  15

Val

<210> SEQ ID NO 117
<211> LENGTH: 321
<212> TYPE: DNA
<213> ORGANISM: Artificial Sequence
<220> FEATURE:
<223> OTHER INFORMATION: Synthetic

<400> SEQUENCE: 117
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct aatctatgct gcatcccgtt tgcaaagtgg ggtcccatcg    180
aggttcagcg gcagtggatc tgggacagaa ttcactctca caatcagcag cctgcagcct    240
gaagattttg gaacttatta ctgtctacag cataatagtc accccacctt cggccaaggg    300
accaaggtgg agatcaaacg a                                              321

<210> SEQ ID NO 118
<211> LENGTH: 107
<212> TYPE: PRT
<213> ORGANISM: Artificial Sequence
<220> FEATURE:
<223> OTHER INFORMATION: Synthetic

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Lys Pro Gly Lys Ala Pro Lys Arg Leu Ile
            35                  40                  45

Tyr Ala Ala Ser Arg Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Gly Thr Tyr Tyr Cys Leu Gln His Asn Ser His Pro Thr
                85                  90                  95

Phe Gly Gln Gly Thr Lys Val Glu Ile Lys Arg
            100                 105

<210> SEQ ID NO 119
<211> LENGTH: 18
<212> TYPE: DNA
<213> ORGANISM: Artificial Sequence
<220> FEATURE:
<223> OTHER INFORMATION: Synthetic

<400> SEQUENCE: 119
cagggcatta gaaatgat                                                   18

<210> SEQ ID NO 120
<211> LENGTH: 6
<212> TYPE: PRT
<213> ORGANISM: Artificial Sequence
<220> FEATURE:
<223> OTHER INFORMATION: Synthetic

<400> SEQUENCE: 120

Gln Gly Ile Arg Asn Asp
 1               5

<210> SEQ ID NO 121
<211> LENGTH: 9
<212> TYPE: DNA
<213> ORGANISM: Artificial Sequence
<220> FEATURE:
<223> OTHER INFORMATION: Synthetic

<400> SEQUENCE: 121 gctgcatcc                                                                  9

<210> SEQ ID NO 122
<211> LENGTH: 3
<212> TYPE: PRT
<213> ORGANISM: Artificial Sequence
<220> FEATURE:
<223> OTHER INFORMATION: Synthetic

<400> SEQUENCE: 122

Ala Ala Ser
 1

<210> SEQ ID NO 123
<211> LENGTH: 24
<212> TYPE: DNA
<213> ORGANISM: Artificial Sequence
<220> FEATURE:
<223> OTHER INFORMATION: Synthetic

<400> SEQUENCE: 123
ctacagcata atagtcaccc cacc                                                 24

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

Leu Gln His Asn Ser His Pro Thr
 1               5

<210> SEQ ID NO 125
<211> LENGTH: 369
<212> TYPE: DNA
<213> ORGANISM: Artificial Sequence
<220> FEATURE:
<223> OTHER INFORMATION: Synthetic

<400> SEQUENCE: 125
caggtgcagc tggtggagtc tgggggaggc gtggtccagc ctgggaggtc cctgagactc        60
tcctgtgcag cgtctgggtt cacctttagt aactttggca tgcactgggt ccgccaggct       120
ccaggcaagg ggctggagtg ggtggcagtt atatggtttg atgaaattga taatactat        180

```
gcagactccg tgaagggccg attcaccatc tccagagaca attccaagaa cacgctgtat      240
ccgcaaatga acagcctgag agccgaagac acggctgtgt attactgtgc gcagaagat       300 tacgatattt tgactggtta ctattacgct atggacgtct ggggccaagg gaccacggtc      360
accgtctcc                                                              369
```

```
<210> SEQ ID NO 126
<211> LENGTH: 123
<212> TYPE: PRT
<213> ORGANISM: Artificial Sequence
<220> FEATURE:
<223> OTHER INFORMATION: Synthetic

<400> SEQUENCE: 126
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Val Ile Trp Phe Asp Glu Ile Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Pro Gln Met Asn Ser Leu Arg Ala Glu Asp Thr Ala Val Tyr Tyr Cys
                85                  90                  95

Ala Arg Glu Asp Tyr Asp Ile Leu Thr Gly Tyr Tyr Tyr Ala Met Asp
            100                 105                 110

Val Trp Gly Gln Gly Thr Thr Val Thr Val Ser
        115                 120

```
<210> SEQ ID NO 127
<211> LENGTH: 318
<212> TYPE: DNA
<213> ORGANISM: Artificial Sequence
<220> FEATURE:
<223> OTHER INFORMATION: Synthetic

<400> SEQUENCE: 127
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct aatctatgct gcatcccgtt tgcaaagtgg ggtcccatcg    180
aggttcagcg gcagtggatc tgggacagaa ttcactctca caatcagcag cctgcagcct    240
gaagattttg aacttatta ctgtctacag cataatagtc accccacctt cggccaaggg     300
accaaggtgg agatcaaa                                                   318
```

```
<210> SEQ ID NO 128
<211> LENGTH: 106
<212> TYPE: PRT
<213> ORGANISM: Artificial Sequence
<220> FEATURE:
<223> OTHER INFORMATION: Synthetic

<400> SEQUENCE: 128
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Lys Asn Asp

```
                    20                  25                  30
Leu Gly Trp Tyr Gln Gln Lys Pro Gly Lys Ala Pro Lys Arg Leu Ile
            35                  40                  45

Tyr Ala Ala Ser Arg Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Gly Thr Tyr Tyr Cys Leu Gln His Asn Ser His Pro Thr
                85                  90                  95

Phe Gly Gln Gly Thr Lys Val Glu Ile Lys
            100                 105

<210> SEQ ID NO 129
<211> LENGTH: 381
<212> TYPE: DNA
<213> ORGANISM: Artificial Sequence
<220> FEATURE:
<223> OTHER INFORMATION: Synthetic

<400> SEQUENCE: 129
gaggtgcagc tggtggagtc ggggggaggc atggtacagc ctggggggtc cctgagactc      60
tcctgtgcag cctctggatt cacctccagt aactacgaca tgcactgggt ccgccaagct    120
acaggaaaag gtctggagtg ggtctcaagt attgatactg ctggggacac ttactatcca    180
gactccgtga agggccgctt tatcatctcc agagaaaatg ccaaaaactc cctgtatctt    240
caaatgaata gcctgagagc cggggacacg gctgtgtatt actgtacaag ggagccccga    300
aattacgaaa tttttgactgg tcactaccac taccacggta tggacatctg gggccaaggg    360
accacggtca ccgtctcctc a                                               381

<210> SEQ ID NO 130
<211> LENGTH: 127
<212> TYPE: PRT
<213> ORGANISM: Artificial Sequence
<220> FEATURE:
<223> OTHER INFORMATION: Synthetic

<400> SEQUENCE: 130

Glu Val Gln Leu Val Glu Ser Gly Gly Gly Met Val Gln Pro Gly Gly
1               5                   10                  15

Ser Leu Arg Leu Ser Cys Ala Ala Ser Gly Phe Thr Ser Ser Asn Tyr
            20                  25                  30

Asp Met His Trp Val Arg Gln Ala Thr Gly Lys Gly Leu Glu Trp Val
        35                  40                  45

Ser Ser Ile Asp Thr Ala Gly Asp Thr Tyr Tyr Pro Asp Ser Val Lys
    50                  55                  60

Gly Arg Phe Ile Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Thr
                85                  90                  95

Arg Glu Pro Arg Asn Tyr Glu Ile Leu Thr Gly His Tyr His Tyr His
            100                 105                 110

Gly Met Asp Ile Trp Gly Gln Gly Thr Thr Val Thr Val Ser Ser
        115                 120                 125

<210> SEQ ID NO 131
<211> LENGTH: 24
<212> TYPE: DNA
```

```
<213> ORGANISM: Artificial Sequence
<220> FEATURE:
<223> OTHER INFORMATION: Synthetic

<400> SEQUENCE: 131
ggattcacct ccagtaacta cgac                                          24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Phe Thr Ser Ser Asn Tyr Asp
 1               5

<210> SEQ ID NO 133
<211> LENGTH: 21
<212> TYPE: DNA
<213> ORGANISM: Artificial Sequence
<220> FEATURE:
<223> OTHER INFORMATION: Synthetic

<400> SEQUENCE: 133
attgatactg ctggggacac t                                             21

<210> SEQ ID NO 134
<211> LENGTH: 7
<212> TYPE: PRT
<213> ORGANISM: Artificial Sequence
<220> FEATURE:
<223> OTHER INFORMATION: Synthetic

<400> SEQUENCE: 134

Ile Asp Thr Ala Gly Asp Thr
 1               5

<210> SEQ ID NO 135
<211> LENGTH: 63
<212> TYPE: DNA
<213> ORGANISM: Artificial Sequence
<220> FEATURE:
<223> OTHER INFORMATION: Synthetic

<400> SEQUENCE: 135
acaagggagc cccgaaatta cgaaattttg actggtcact accactacca cggtatggac    60
atc                                                                 63

<210> SEQ ID NO 136
<211> LENGTH: 21
<212> TYPE: PRT
<213> ORGANISM: Artificial Sequence
<220> FEATURE:
<223> OTHER INFORMATION: Synthetic

<400> SEQUENCE: 136

Thr Arg Glu Pro Arg Asn Tyr Glu Ile Leu Thr Gly His Tyr His Tyr
 1               5                  10                  15

His Gly Met Asp Ile
            20

<210> SEQ ID NO 137
<211> LENGTH: 324
```

<212> TYPE: DNA
<213> ORGANISM: Artificial Sequence
<220> FEATURE:
<223> OTHER INFORMATION: Synthetic

<400> SEQUENCE: 137

```
gacatccaga tgacccagtc gccatcctcc ctgtctgcat ctgtaggaga cagagtcacc    60
atcacttgcc gggcaagtca ggccattaga aatgatttag ctggtatca gcagaaacca   120
gggaaagccc ctaaactcct gatctatact gcattcagtt tacagagtgg ggtcccatca   180
aggttcagcg gcagtaaatc tggcacagac ttcactctca ccatcagcag cctgcagcct   240
gaagattttg cgacttatta ctgtctgcag gattacacta tcctcggac gttcggccaa   300
gggaccaagg tggagatcaa acga                                          324
```

<210> SEQ ID NO 138
<211> LENGTH: 108
<212> TYPE: PRT
<213> ORGANISM: Artificial Sequence
<220> FEATURE:
<223> OTHER INFORMATION: Synthetic

<400> SEQUENCE: 138

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Ala Ile Arg Asn Asp
            20                  25                  30
Leu Gly Trp Tyr Gln Gln Lys Pro Gly Lys Ala Pro Lys Leu Leu Ile
        35                  40                  45
Tyr Thr Ala Phe Ser Leu Gln Ser Gly Val Pro Ser Arg Phe Ser Gly
    50                  55                  60
Ser Lys Ser Gly Thr Asp Phe Thr Leu Thr Ile Ser Ser Leu Gln Pro
65                  70                  75                  80
Glu Asp Phe Ala Thr Tyr Tyr Cys Leu Gln Asp Tyr Thr Asn Pro Arg
                85                  90                  95
Thr Phe Gly Gln Gly Thr Lys Val Glu Ile Lys Arg
            100                 105
```

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139

```
caggccatta gaaatgat                                                  18
```

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

```
Gln Ala Ile Arg Asn Asp
 1               5
```

<210> SEQ ID NO 141
<211> LENGTH: 9
<212> TYPE: DNA

```
<213> ORGANISM: Artificial Sequence
<220> FEATURE:
<223> OTHER INFORMATION: Synthetic

<400> SEQUENCE: 141 actgcattc                                                                   9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Thr Ala Phe
 1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
ctgcaggatt acactaatcc tcggacg                                              27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Leu Gln Asp Tyr Thr Asn Pro Arg Thr
  1               5

<210> SEQ ID NO 145
<211> LENGTH: 378
<212> TYPE: DNA
<213> ORGANISM: Artificial Sequence
<220> FEATURE:
<223> OTHER INFORMATION: Synthetic

<400> SEQUENCE: 145
gaggtgcagc tggtggagtc ggggggaggc atggtacagc ctgggggtc cctgagactc           60 tcctgtgcag cctctggatt cacctccagt aactacgaca tgcactgggt ccgccaagct         120
acaggaaaag gtctggagtg ggtctcaagt attgatactg ctggggacac ttactatcca         180
gactccgtga agggccgctt tatcatctcc agagaaaatg ccaaaaactc cctgtatctt         240
caaatgaata gcctgagagc cggggacacg gctgtgtatt actgtacaag ggagccccga         300
aattacgaaa tttttgactgg tcactaccac taccacggta tggacatctg gggccaaggg       360
accacggtca ccgtctcc                                                       378

<210> SEQ ID NO 146
<211> LENGTH: 126
<212> TYPE: PRT
<213> ORGANISM: Artificial Sequence
<220> FEATURE:
<223> OTHER INFORMATION: Synthetic

<400> SEQUENCE: 146
```

```
Glu Val Gln Leu Val Glu Ser Gly Gly Gly Met Val Gln Pro Gly Gly
  1               5                  10                  15

Ser Leu Arg Leu Ser Cys Ala Ala Ser Gly Phe Thr Ser Ser Asn Tyr
             20                  25                  30

Asp Met His Trp Val Arg Gln Ala Thr Gly Lys Gly Leu Glu Trp Val
         35                  40                  45

Ser Ser Ile Asp Thr Ala Gly Asp Thr Tyr Tyr Pro Asp Ser Val Lys
 50                  55                  60

Gly Arg Phe Ile Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Thr
             85                  90                  95

Arg Glu Pro Arg Asn Tyr Glu Ile Leu Thr Gly His Tyr His Tyr His
            100                 105                 110

Gly Met Asp Ile Trp Gly Gln Gly Thr Thr Val Thr Val Ser
            115                 120                 125

<210> SEQ ID NO 147
<211> LENGTH: 321
<212> TYPE: DNA
<213> ORGANISM: Artificial Sequence
<220> FEATURE:
<223> OTHER INFORMATION: Synthetic

<400> SEQUENCE: 147
gccatccaga tgacccagtc gccatcctcc ctgtctgcat ctgtaggaga cagagtcacc      60
atcacttgcc gggcaagtca ggccattaga aatgatttag gctggtatca gcagaaacca    120
gggaaagccc ctaaactcct gatctatact gcattcagtt tacagagtgg ggtcccatca    180
aggttcagcg gcagtaaatc tggcacagac ttcactctca ccatcagcag cctgcagcct    240
gaagattttg cgacttatta ctgtctgcag gattacacta atcctcggac gttcggccaa    300
gggaccaagg tggaaatcaa a                                               321

<210> SEQ ID NO 148
<211> LENGTH: 107
<212> TYPE: PRT
<213> ORGANISM: Artificial Sequence
<220> FEATURE:
<223> OTHER INFORMATION: Synthetic

<400> SEQUENCE: 148

Ala Ile Gln Met Thr Gln Ser Pro Ser Ser Leu Ser Ala Ser Val Gly
  1               5                  10                  15

Asp Arg Val Thr Ile Thr Cys Arg Ala Ser Gln Ala Ile Arg Asn Asp
             20                  25                  30

Leu Gly Trp Tyr Gln Gln Lys Pro Gly Lys Ala Pro Lys Leu Leu Ile
         35                  40                  45

Tyr Thr Ala Phe Ser Leu Gln Ser Gly Val Pro Ser Arg Phe Ser Gly
 50                  55                  60

Ser Lys Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Thr Asn Pro Arg
             85                  90                  95

Thr Phe Gly Gln Gly Thr Lys Val Glu Ile Lys
            100                 105
```

<210> SEQ ID NO 149
<211> LENGTH: 345
<212> TYPE: PRT
<213> ORGANISM: Artificial Sequence
<220> FEATURE:
<223> OTHER INFORMATION: Synthetic

<400> SEQUENCE: 149

```
Gln Val Met Asp Phe Leu Phe Glu Lys Trp Lys Leu Tyr Gly Asp Gln
 1               5                  10                  15

Cys His His Asn Leu Ser Leu Leu Pro Pro Thr Glu Leu Val Cys
            20                  25                  30

Asn Arg Thr Phe Asp Lys Tyr Ser Cys Trp Pro Asp Thr Pro Ala Asn
            35                  40                  45

Thr Thr Ala Asn Ile Ser Cys Pro Trp Tyr Leu Pro Trp His His Lys
 50                  55                  60

Val Gln His Arg Phe Val Phe Lys Arg Cys Gly Pro Asp Gly Gln Trp
 65                  70                  75                  80

Val Arg Gly Pro Arg Gly Gln Pro Trp Arg Asp Ala Ser Gln Cys Gln
                 85                  90                  95

Met Asp Gly Glu Glu Ile Glu Val Gln Lys Glu Val Ala Lys Met Tyr
            100                 105                 110

Ser Ser Phe Gln Val Met Asp Lys Thr His Thr Cys Pro Pro Cys Pro
            115                 120                 125

Ala Pro Glu Leu Leu Gly Gly Pro Ser Val Phe Leu Phe Pro Pro Lys
130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
            195                 200                 205

Gln Asp Trp Leu Asn Gly Lys Glu Tyr Lys Cys Lys Val Ser Asn Lys
210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Asp Glu Leu
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
            275                 280                 285

Tyr Lys Thr Thr Pro Pro Val Leu Asp Ser Asp Gly Ser Phe Phe Leu
290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345
```

<210> SEQ ID NO 150
<211> LENGTH: 348
<212> TYPE: PRT

<213> ORGANISM: Artificial Sequence
<220> FEATURE:
<223> OTHER INFORMATION: Synthetic

<400> SEQUENCE: 150

```
Gln Val Met Asp Phe Leu Phe Glu Lys Trp Lys Leu Tyr Gly Asp Gln
1               5                   10                  15

Cys His His Asn Leu Ser Leu Leu Pro Pro Thr Glu Leu Val Cys
            20                  25                  30

Asn Arg Thr Phe Asp Lys Tyr Ser Cys Trp Pro Asp Thr Pro Ala Asn
            35                  40                  45

Thr Thr Ala Asn Ile Ser Cys Pro Trp Tyr Leu Pro Trp His His Lys
        50                  55                  60

Val Gln His Arg Phe Val Phe Lys Arg Cys Gly Pro Asp Gly Gln Trp
65                  70                  75                  80

Val Arg Gly Pro Arg Gly Gln Pro Trp Arg Asp Ala Ser Gln Cys Gln
                85                  90                  95

Met Asp Gly Glu Glu Ile Glu Val Gln Lys Glu Val Ala Lys Met Tyr
            100                 105                 110

Ser Ser Phe Gln Val Met Gly Pro Gly Asp Lys Thr His Thr Cys Pro
        115                 120                 125

Pro Cys Pro Ala Pro Glu Leu Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345
```

<210> SEQ ID NO 151
<211> LENGTH: 146
<212> TYPE: PRT
<213> ORGANISM: Artificial Sequence
<220> FEATURE:
<223> OTHER INFORMATION: Synthetic

<400> SEQUENCE: 151

```
Gln Val Met Asp Phe Leu Phe Glu Lys Trp Lys Leu Tyr Gly Asp Gln
 1               5                   10                  15

Cys His His Asn Leu Ser Leu Leu Pro Pro Thr Glu Leu Val Cys
            20                  25                  30

Asn Arg Thr Phe Asp Lys Tyr Ser Cys Trp Pro Asp Thr Pro Ala Asn
            35                  40                  45

Thr Thr Ala Asn Ile Ser Cys Pro Trp Tyr Leu Pro Trp His His Lys
        50                  55                  60

Val Gln His Arg Phe Val Phe Lys Arg Cys Gly Pro Asp Gly Gln Trp
65                  70                  75                  80

Val Arg Gly Pro Arg Gly Gln Pro Trp Arg Asp Ala Ser Gln Cys Gln
                85                  90                  95

Met Asp Gly Glu Glu Ile Glu Val Gln Lys Glu Val Ala Lys Met Tyr
            100                 105                 110

Ser Ser Phe Gln Val Met Glu Gln Lys Leu Ile Ser Glu Glu Asp Leu
        115                 120                 125

Gly Gly Glu Gln Lys Leu Ile Ser Glu Glu Asp Leu His His His His
    130                 135                 140

His His
145
```

<210> SEQ ID NO 152
<211> LENGTH: 351
<212> TYPE: PRT
<213> ORGANISM: Artificial Sequence
<220> FEATURE:
<223> OTHER INFORMATION: Synthetic

<400> SEQUENCE: 152

```
Gly Ala Pro Gln Val Met Asp Phe Leu Phe Glu Lys Trp Lys Leu Tyr
 1               5                   10                  15

Gly Asp Gln Cys His His Asn Leu Ser Leu Leu Pro Pro Thr Glu
            20                  25                  30

Leu Val Cys Asn Arg Thr Phe Asp Lys Tyr Ser Cys Trp Pro Asp Thr
        35                  40                  45

Pro Ala Asn Thr Thr Ala Asn Ile Ser Cys Pro Trp Tyr Leu Pro Trp
    50                  55                  60

His His Lys Val Gln His Arg Phe Val Phe Lys Arg Cys Gly Pro Asp
65                  70                  75                  80

Gly Gln Trp Val Arg Gly Pro Arg Gly Gln Pro Trp Arg Asp Ala Ser
                85                  90                  95

Gln Cys Gln Met Asp Gly Glu Glu Leu Glu Val Gln Lys Glu Val Ala
            100                 105                 110

Lys Met Tyr Ser Ser Phe Gln Val Met Gly Pro Gly Asp Lys Thr His
        115                 120                 125

Thr Cys Pro Pro Cys Pro Ala Pro Glu Leu Leu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
            180                 185                 190
```

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
            245                 250                 255

Pro Ser Arg Asp Glu Leu Thr Lys Asn Gln Val Ser Leu Thr Cys Leu
                260                 265                 270

Val Lys Gly Phe Tyr Pro Ser Asp Ile Ala Val Glu Trp Glu Ser Asn
            275                 280                 285

Gly Gln Pro Glu Asn Asn Tyr Lys Thr Thr Pro Pro Val Leu Asp Ser
        290                 295                 300

Asp Gly Ser Phe Phe Leu Tyr Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu Ser Pro Gly Lys
            340                 345                 350

<210> SEQ ID NO 153
<211> LENGTH: 477
<212> TYPE: PRT
<213> ORGANISM: Homo sapiens

<400> SEQUENCE: 153

Met Pro Pro Cys Gln Pro Gln Arg Pro Leu Leu Leu Leu Leu Leu Leu
  1                 5                  10                  15

Leu Ala Cys Gln Pro Gln Val Pro Ser Ala Gln Val Met Asp Phe Leu
                20                  25                  30

Phe Glu Lys Trp Lys Leu Tyr Gly Asp Gln Cys His His Asn Leu Ser
            35                  40                  45

Leu Leu Pro Pro Pro Thr Glu Leu Val Cys Asn Arg Thr Phe Asp Lys
        50                  55                  60

Tyr Ser Cys Trp Pro Asp Thr Pro Ala Asn Thr Thr Ala Asn Ile Ser
65                  70                  75                  80

Cys Pro Trp Tyr Leu Pro Trp His His Lys Val Gln His Arg Phe Val
                85                  90                  95

Phe Lys Arg Cys Gly Pro Asp Gly Gln Trp Val Arg Gly Pro Arg Gly
            100                 105                 110

Gln Pro Trp Arg Asp Ala Ser Gln Cys Gln Met Asp Gly Glu Glu Ile
        115                 120                 125

Glu Val Gln Lys Glu Val Ala Lys Met Tyr Ser Ser Phe Gln Val Met
    130                 135                 140

Tyr Thr Val Gly Tyr Ser Leu Ser Leu Gly Ala Leu Leu Leu Ala Leu
145                 150                 155                 160

Ala Ile Leu Gly Gly Leu Ser Lys Leu His Cys Thr Arg Asn Ala Ile
                165                 170                 175

His Ala Asn Leu Phe Ala Ser Phe Val Leu Lys Ala Ser Ser Val Leu
            180                 185                 190

Val Ile Asp Gly Leu Leu Arg Thr Arg Tyr Ser Gln Lys Ile Gly Asp
        195                 200                 205

Asp Leu Ser Val Ser Thr Trp Leu Ser Asp Gly Ala Val Ala Gly Cys
    210                 215                 220

```
Arg Val Ala Val Phe Met Gln Tyr Gly Ile Val Ala Asn Tyr Cys
225                 230                 235                 240

Trp Leu Leu Val Glu Gly Leu Tyr Leu His Asn Leu Leu Gly Leu Ala
            245                 250                 255

Thr Leu Pro Glu Arg Ser Phe Phe Ser Leu Tyr Leu Gly Ile Gly Trp
                260                 265                 270

Gly Ala Pro Met Leu Phe Val Val Pro Trp Ala Val Val Lys Cys Leu
            275                 280                 285

Phe Glu Asn Val Gln Cys Trp Thr Ser Asn Asp Asn Met Gly Phe Trp
            290                 295                 300

Trp Ile Leu Arg Phe Pro Val Phe Leu Ala Ile Leu Asn Phe Phe
305                 310                 315                 320

Ile Phe Val Arg Ile Val Gln Leu Leu Val Ala Lys Leu Arg Ala Arg
                325                 330                 335

Gln Met His His Thr Asp Tyr Lys Phe Arg Leu Ala Lys Ser Thr Leu
                340                 345                 350

Thr Leu Ile Pro Leu Leu Gly Val His Glu Val Val Phe Ala Phe Val
            355                 360                 365

Thr Asp Glu His Ala Gln Gly Thr Leu Arg Ser Ala Lys Leu Phe Phe
370                 375                 380

Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg Arg Trp His
                405                 410                 415

Arg Trp Arg Leu Gly Lys Val Leu Trp Glu Glu Arg Asn Thr Ser Asn
                420                 425                 430

His Arg Ala Ser Ser Ser Pro Gly His Gly Pro Pro Ser Lys Glu Leu
                435                 440                 445

Gln Phe Gly Arg Gly Gly Ser Gln Asp Ser Ser Ala Glu Thr Pro
450                 455                 460

Leu Ala Gly Gly Leu Pro Arg Leu Ala Glu Ser Pro Phe
465                 470                 475

<210> SEQ ID NO 154
<211> LENGTH: 485
<212> TYPE: PRT
<213> ORGANISM: Mus musculus

<400> SEQUENCE: 154

Met Ala Leu Thr Gln Leu His Cys Pro His Leu Leu Leu Leu Leu
1               5                   10                  15

Val Leu Ser Cys Leu Pro Glu Ala Pro Ser Ala Gln Val Met Asp Phe
            20                  25                  30

Leu Phe Glu Lys Trp Lys Leu Tyr Ser Asp Gln Cys His His Asn Leu
        35                  40                  45

Ser Leu Leu Pro Pro Thr Glu Leu Val Cys Asn Arg Thr Phe Asp
    50                  55                  60

Lys Tyr Ser Cys Trp Pro Asp Thr Pro Asn Thr Thr Ala Asn Ile
65                  70                  75                  80

Ser Cys Pro Trp Tyr Leu Pro Trp Tyr His Lys Val Gln His Arg Leu
                85                  90                  95

Val Phe Lys Arg Cys Gly Pro Asp Gly Gln Trp Val Arg Gly Pro Arg
            100                 105                 110

Gly Gln Pro Trp Arg Asn Ala Ser Gln Cys Gln Leu Asp Asp Glu Glu
```

```
            115                 120                 125
Ile Glu Val Gln Lys Gly Val Ala Lys Met Tyr Ser Ser Gln Gln Val
130                 135                 140

Met Tyr Thr Val Gly Tyr Ser Leu Ser Leu Gly Ala Leu Leu Leu Ala
145                 150                 155                 160

Leu Val Ile Leu Leu Gly Leu Arg Lys Leu His Cys Thr Arg Asn Tyr
                165                 170                 175

Ile His Gly Asn Leu Phe Ala Ser Phe Val Leu Lys Ala Gly Ser Val
            180                 185                 190

Leu Val Ile Asp Trp Leu Leu Lys Thr Arg Tyr Ser Gln Lys Ile Gly
        195                 200                 205

Asp Asp Leu Ser Val Ser Val Trp Leu Ser Asp Gly Ala Met Ala Gly
    210                 215                 220

Cys Arg Val Ala Thr Val Ile Met Gln Tyr Gly Ile Ile Ala Asn Tyr
225                 230                 235                 240

Cys Trp Leu Leu Val Glu Gly Val Tyr Leu Tyr Ser Leu Leu Ser Leu
                245                 250                 255

Ala Thr Phe Ser Glu Arg Ser Phe Phe Ser Leu Tyr Leu Gly Ile Gly
            260                 265                 270

Trp Gly Ala Pro Leu Leu Phe Val Ile Pro Trp Val Val Val Lys Cys
        275                 280                 285

Leu Phe Glu Asn Val Gln Cys Trp Thr Ser Asn Asp Asn Met Gly Phe
    290                 295                 300

Trp Trp Ile Leu Arg Ile Pro Val Phe Leu Ala Leu Leu Ile Asn Phe
305                 310                 315                 320

Phe Ile Phe Val His Ile Ile His Leu Leu Val Ala Lys Leu Arg Ala
                325                 330                 335

His Gln Met His Tyr Ala Asp Tyr Lys Phe Arg Leu Ala Arg Ser Thr
            340                 345                 350

Leu Thr Leu Ile Pro Leu Leu Gly Val His Glu Val Val Phe Ala Phe
        355                 360                 365

Val Thr Asp Glu His Ala Gln Gly Thr Leu Arg Ser Thr Lys Leu Phe
    370                 375                 380

Phe Asp Leu Phe Leu Ser Ser Phe Gln Gly Leu Leu Val Ala Val Leu
385                 390                 395                 400

Tyr Cys Phe Leu Asn Lys Glu Val Gln Ala Glu Leu Met Arg Arg Trp
                405                 410                 415

Arg Gln Trp Gln Glu Gly Lys Ala Leu Gln Glu Glu Arg Leu Ala Ser
            420                 425                 430

Ser His Gly Ser His Met Ala Pro Ala Gly Pro Cys His Gly Asp Pro
        435                 440                 445

Cys Glu Lys Leu Gln Leu Met Ser Ala Gly Ser Ser Ser Gly Thr Gly
    450                 455                 460

Cys Val Pro Ser Met Glu Thr Ser Leu Ala Ser Ser Leu Pro Arg Leu
465                 470                 475                 480

Ala Asp Ser Pro Thr
                485

<210> SEQ ID NO 155
<211> LENGTH: 491
<212> TYPE: PRT
<213> ORGANISM: Macaca fascicularis

<400> SEQUENCE: 155
```

-continued

```
Met Ala Pro Cys Gln Pro Arg Arg Pro Leu Leu Leu Leu Leu Leu
  1               5                  10                  15
Leu Ala Cys Gln Pro Gln Ala Pro Ser Ala Gln Val Met Asp Phe Leu
             20                  25                  30
Phe Glu Lys Trp Lys Leu Tyr Gly Asp Gln Cys His His Asn Leu Ser
             35                  40                  45
Leu Leu Pro Pro Pro Thr Glu Leu Val Cys Asn Arg Thr Phe Asp Lys
 50                  55                  60
Tyr Ser Cys Trp Pro Asp Thr Pro Ala Asn Thr Thr Ala Asn Ile Ser
 65                  70                  75                  80
Cys Pro Trp Tyr Leu Pro Trp His His Lys Val Gln His Arg Phe Val
                 85                  90                  95
Phe Lys Arg Cys Gly Pro Asp Gly Gln Trp Val Arg Gly Pro Arg Gly
            100                 105                 110
Gln Pro Trp Arg Asp Ala Ser Gln Cys Gln Met Asp Gly Glu Glu Leu
            115                 120                 125
Glu Val Gln Lys Glu Val Ala Lys Met Tyr Ser Ser Phe Gln Val Met
            130                 135                 140
Tyr Thr Val Gly Tyr Ser Leu Ser Leu Gly Ala Leu Leu Leu Ala Leu
145                 150                 155                 160
Ala Ile Leu Gly Gly Ile Ser Lys Leu His Cys Thr Arg Asn Ala Ile
                165                 170                 175
His Ala Asn Leu Phe Val Ser Phe Val Leu Lys Ala Ser Ser Val Leu
                180                 185                 190
Val Ile Asp Gly Leu Leu Arg Thr Arg Tyr Ser Gln Lys Ile Gly Asp
            195                 200                 205
Asp Leu Ser Val Ser Ile Trp Leu Ser Asp Gly Ala Val Ala Gly Cys
            210                 215                 220
Arg Val Ala Ala Val Phe Met Gln Tyr Gly Val Val Ala Asn Tyr Cys
225                 230                 235                 240
Trp Leu Leu Val Glu Gly Leu Tyr Leu His Asn Leu Leu Gly Leu Ala
                245                 250                 255
Thr Leu Pro Glu Arg Ser Phe Phe Ser Leu Tyr Leu Gly Ile Gly Trp
            260                 265                 270
Gly Ala Pro Met Leu Phe Ile Ile Pro Trp Val Val Arg Cys Leu
            275                 280                 285
Phe Glu Asn Ile Gln Cys Trp Thr Ser Asn Asp Asn Met Gly Phe Trp
            290                 295                 300
Trp Ile Leu Arg Phe Pro Val Phe Leu Ala Ile Leu Ile Asn Phe Phe
305                 310                 315                 320
Ile Phe Ile Arg Ile Val His Leu Leu Val Ala Lys Leu Arg Ala Arg
                325                 330                 335
Glu Met His His Thr Asp Tyr Lys Phe Arg Leu Ala Lys Ser Thr Leu
            340                 345                 350
Thr Leu Ile Pro Leu Leu Gly Val His Glu Val Phe Ala Phe Val
            355                 360                 365
Thr Asp Glu His Ala Gln Gly Thr Leu Arg Phe Ala Lys Leu Phe Phe
            370                 375                 380
Asp Leu Phe Leu Ser Ser Phe Gln Gly Leu Leu Val Ala Val Leu Tyr
385                 390                 395                 400
Cys Phe Leu Asn Lys Glu Val Gln Ser Glu Leu Arg Arg His Trp His
                405                 410                 415
Arg Trp Arg Leu Gly Lys Val Leu Gln Glu Glu Arg Gly Thr Ser Asn
```

```
                420             425             430
His Lys Ala Pro Ser Ala Pro Gly Gln Gly Leu Pro Gly Lys Lys Leu
                435             440             445

Gln Ser Gly Arg Asp Gly Gly Ser Gln Asp Ser Ser Ala Glu Ile Pro
            450             455             460

Leu Ala Gly Gly Leu Pro Arg Leu Ala Glu Ser Pro Phe Ser Thr Leu
465             470             475             480

Leu Gly Pro Gln Leu Gly Leu Asp Ser Gly Thr
                485             490

<210> SEQ ID NO 156
<211> LENGTH: 485
<212> TYPE: PRT
<213> ORGANISM: Rattus norvegicus

<400> SEQUENCE: 156

Met Val Leu Thr Gln Leu His Cys Pro Tyr Leu Leu Leu Leu Leu Val
1               5                   10                  15

Val Leu Ser Cys Leu Pro Lys Ala Pro Ser Ala Gln Val Met Asp Phe
            20                  25                  30

Leu Phe Glu Lys Trp Lys Leu Tyr Ser Asp Gln Cys His His Asn Leu
        35                  40                  45

Ser Leu Leu Pro Pro Pro Thr Glu Leu Val Cys Asn Arg Thr Phe Asp
    50                  55                  60

Lys Tyr Ser Cys Trp Pro Asp Thr Pro Pro Asn Thr Thr Ala Asn Ile
65                  70                  75                  80

Ser Cys Pro Trp Tyr Leu Pro Trp Tyr His Lys Val Gln His Arg Leu
                85                  90                  95

Val Phe Lys Arg Cys Gly Pro Asp Gly Gln Trp Val Arg Gly Pro Arg
            100                 105                 110

Gly Gln Ser Trp Arg Asp Ala Ser Gln Cys Gln Met Asp Asp Asp Glu
        115                 120                 125

Ile Glu Val Gln Lys Gly Val Ala Lys Met Tyr Ser Ser Tyr Gln Val
    130                 135                 140

Met Tyr Thr Val Gly Tyr Ser Leu Ser Leu Gly Ala Leu Leu Leu Ala
145                 150                 155                 160

Leu Val Ile Leu Leu Gly Leu Arg Lys Leu His Cys Thr Arg Asn Tyr
                165                 170                 175

Ile His Gly Asn Leu Phe Ala Ser Phe Val Leu Lys Ala Gly Ser Val
            180                 185                 190

Leu Val Ile Asp Trp Leu Leu Lys Thr Arg Tyr Ser Gln Lys Ile Gly
        195                 200                 205

Asp Asp Leu Ser Val Ser Val Trp Leu Ser Asp Gly Ala Val Ala Gly
    210                 215                 220

Cys Arg Val Ala Thr Val Ile Met Gln Tyr Gly Ile Ile Ala Asn Tyr
225                 230                 235                 240

Cys Trp Leu Leu Val Glu Gly Val Tyr Leu Tyr Ser Leu Leu Ser Ile
                245                 250                 255

Thr Thr Phe Ser Glu Lys Ser Phe Phe Ser Leu Tyr Leu Cys Ile Gly
            260                 265                 270

Trp Gly Ser Pro Leu Leu Phe Val Ile Pro Trp Val Val Lys Cys
        275                 280                 285

Leu Phe Glu Asn Val Gln Cys Trp Thr Ser Asn Asp Asn Met Gly Phe
    290                 295                 300
```

```
Trp Trp Ile Leu Arg Ile Pro Val Leu Leu Ala Ile Leu Ile Asn Phe
305                 310                 315                 320

Phe Ile Phe Val Arg Ile Ile His Leu Leu Val Ala Lys Leu Arg Ala
                325                 330                 335

His Gln Met His Tyr Ala Asp Tyr Lys Phe Arg Leu Ala Arg Ser Thr
                340                 345                 350

Leu Thr Leu Ile Pro Leu Leu Gly Val His Glu Val Phe Ala Phe
                355                 360                 365

Val Thr Asp Glu His Ala Gln Gly Thr Leu Arg Ser Thr Lys Leu Phe
                370                 375                 380

Phe Asp Leu Phe Phe Ser Ser Phe Gln Gly Leu Leu Val Ala Val Leu
385                 390                 395                 400

Tyr Cys Phe Leu Asn Lys Glu Val Gln Ala Glu Leu Leu Arg Arg Trp
                405                 410                 415

Arg Arg Trp Gln Glu Gly Lys Ala Leu Gln Glu Arg Met Ala Ser
                420                 425                 430

Ser His Gly Ser His Met Ala Pro Ala Gly Thr Cys His Gly Asp Pro
                435                 440                 445

Cys Glu Lys Leu Gln Leu Met Ser Ala Gly Ser Ser Gly Thr Gly
                450                 455                 460

Cys Glu Pro Ser Ala Lys Thr Ser Leu Ala Ser Ser Leu Pro Arg Leu
465                 470                 475                 480

Ala Asp Ser Pro Thr
                485

<210> SEQ ID NO 157
<211> LENGTH: 1434
<212> TYPE: DNA
<213> ORGANISM: Homo sapiens

<400> SEQUENCE: 157 atgccccct gccagccaca gcgacccctg ctgctgttgc tgctgctgct ggcctgccag      60
ccacaggtcc cctccgctca ggtgatggac ttcctgtttg agaagtggaa gctctacggt     120
gaccagtgtc accacaacct gagcctgctg ccccctccca cggagctggt gtgcaacaga     180
accttcgaca gtattcctg ctggccggac accccgcca ataccacggc caacatctcc       240 tgccctggt acctgccttg caccacaaa gtgcaacacc gcttcgtgtt caagagatgc       300
gggcccgacg tcagtgggt gcgtggaccc cggggggcagc cttggcgtga tgcctcccag    360
tgccagatgg atggcgagga gattgaggtc cagaaggagg tggccaagat gtacagcagc   420
ttccaggtga tgtacacagt gggctacagc ctgtccctgg ggccctgct cctcgccttg     480 gccatcctgg ggggcctcag caagctgcac tgcacccgca atgccatcca gcgaatctg    540 tttgcgtcct tcgtgctgaa agccagctcc gtgctggtca ttgatgggct gctcaggacc   600
cgctacagcc agaaaattgg cgacgacctc agtgtcagca cctggctcag tgatggagcg   660
gtggctggct gccgtgtggc cgcggtgttc atgcaatatg gcatcgtggc caactactgc   720
tggctgctgg tggagggcct gtacctgcac aacctgctgg gcctggccac cctccccgag   780
aggagcttct tcagcctcta cctgggcatc ggctggggtg ccccatgct gttcgtcgtc   840 ccctgggcag tggtcaagtg tctgttcgag aacgtccagt gctggaccag caatgacaac   900
atgggcttct ggtggatcct gcggttcccc gtcttcctgg ccatcctgat caacttcttc   960
atcttcgtcc gcatcgttca gctgctcgtg gccaagctgc gggcacggca gatgcaccac  1020
acagactaca agttccggct ggccaagtcc acgctgaccc tcatccctct gctgggcgtc  1080
```

```
cacgaagtgg tctttgcctt cgtgacggac gagcacgccc agggcaccct gcgctccgcc    1140
aagctcttct cgacctctt cctcagctcc ttccagggcc tgctggtggc tgtcctctac    1200
tgcttcctca acaaggaggt gcagtcggag ctgcggcggc gttggcaccg ctggcgcctg    1260
ggcaaagtgc tatgggagga gcggaacacc agcaaccaca gggcctcatc ttcgcccggc    1320
cacggccctc ccagcaagga gctgcagttt gggaggggtg gtggcagcca ggattcatct    1380
gcggagaccc ccttggctgg tggcctccct agattggctg agagcccctt ctga          1434

<210> SEQ ID NO 158
<211> LENGTH: 354
<212> TYPE: DNA
<213> ORGANISM: Homo sapiens

<400> SEQUENCE: 158
caggtgatgg acttcctgtt tgagaagtgg aagctctacg gtgaccagtg tcaccacaac     60
ctgagcctgc tgccccctcc cacggagctg gtgtgcaaca gaaccttcga caagtattcc    120
tgctggccgg acacccccgc caataccacg gccaacatct cctgcccctg gtacctgcct    180
tggcaccaca agtgcaaaca ccgcttcgtg ttcaagagat gcgggcccga cggtcagtgg    240
gtgcgtggac cccgggggca gccttggcgt gatgcctccc agtgccagat ggatggcgag    300
gagattgagg tccagaagga ggtggccaag atgtacagca gcttccaggt gatg          354

<210> SEQ ID NO 159
<211> LENGTH: 118
<212> TYPE: PRT
<213> ORGANISM: Homo sapiens

<400> SEQUENCE: 159

Gln Val Met Asp Phe Leu Phe Glu Lys Trp Lys Leu Tyr Gly Asp Gln
  1               5                  10                  15

Cys His His Asn Leu Ser Leu Leu Pro Pro Pro Thr Glu Leu Val Cys
             20                  25                  30

Asn Arg Thr Phe Asp Lys Tyr Ser Cys Trp Pro Asp Thr Pro Ala Asn
         35                  40                  45

Thr Thr Ala Asn Ile Ser Cys Pro Trp Tyr Leu Pro Trp His His Lys
     50                  55                  60

Val Gln His Arg Phe Val Phe Lys Arg Cys Gly Pro Asp Gly Gln Trp
 65                  70                  75                  80

Val Arg Gly Pro Arg Gly Gln Pro Trp Arg Asp Ala Ser Gln Cys Gln
                 85                  90                  95

Met Asp Gly Glu Glu Ile Glu Val Gln Lys Glu Val Ala Lys Met Tyr
            100                 105                 110

Ser Ser Phe Gln Val Met
        115

<210> SEQ ID NO 160
<211> LENGTH: 24
<212> TYPE: DNA
<213> ORGANISM: Artificial Sequence
<220> FEATURE:
<223> OTHER INFORMATION: Synthetic

<400> SEQUENCE: 160
ggattcacct ttaacaacta tgcc                                            24

<210> SEQ ID NO 161
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 161

Gly Phe Thr Phe Asn Asn Tyr Ala
 1               5

<210> SEQ ID NO 162
<211> LENGTH: 24
<212> TYPE: DNA
<213> ORGANISM: Artificial Sequence
<220> FEATURE:
<223> OTHER INFORMATION: Synthetic

<400> SEQUENCE: 162
attagtggta gcggtggtac taca                                              24

<210> SEQ ID NO 163
<211> LENGTH: 8
<212> TYPE: PRT
<213> ORGANISM: Artificial Sequence
<220> FEATURE:
<223> OTHER INFORMATION: Synthetic

<400> SEQUENCE: 163

Ile Ser Gly Ser Gly Gly Thr Thr
 1               5

<210> SEQ ID NO 164
<211> LENGTH: 33
<212> TYPE: DNA
<213> ORGANISM: Artificial Sequence
<220> FEATURE:
<223> OTHER INFORMATION: Synthetic

<400> SEQUENCE: 164
gcgaaagatt ctaactgggg aaatttcgat ctc                                    33

<210> SEQ ID NO 165
<211> LENGTH: 11
<212> TYPE: PRT
<213> ORGANISM: Artificial Sequence
<220> FEATURE:
<223> OTHER INFORMATION: Synthetic

<400> SEQUENCE: 165

Ala Lys Asp Ser Asn Trp Gly Asn Phe Asp Leu
 1               5                  10

<210> SEQ ID NO 166
<211> LENGTH: 36
<212> TYPE: DNA
<213> ORGANISM: Artificial Sequence
<220> FEATURE:
<223> OTHER INFORMATION: Synthetic

<400> SEQUENCE: 166
cagagtgttt tatacaggtc caacaatagg aacttc                                 36

<210> SEQ ID NO 167
<211> LENGTH: 12
<212> TYPE: PRT
<213> ORGANISM: Artificial Sequence
<220> FEATURE:
```

<223> OTHER INFORMATION: Synthetic

<400> SEQUENCE: 167

Gln Ser Val Leu Tyr Arg Ser Asn Asn Arg Asn Phe
 1               5                  10

<210> SEQ ID NO 168
<211> LENGTH: 9
<212> TYPE: DNA
<213> ORGANISM: Artificial Sequence
<220> FEATURE:
<223> OTHER INFORMATION: Synthetic

<400> SEQUENCE: 168 tgggcatct                                                                    9

<210> SEQ ID NO 169
<211> LENGTH: 3
<212> TYPE: PRT
<213> ORGANISM: Artificial Sequence
<220> FEATURE:
<223> OTHER INFORMATION: Synthetic

<400> SEQUENCE: 169

Trp Ala Ser
 1

<210> SEQ ID NO 170
<211> LENGTH: 27
<212> TYPE: DNA
<213> ORGANISM: Artificial Sequence
<220> FEATURE:
<223> OTHER INFORMATION: Synthetic

<400> SEQUENCE: 170
caacaatatt atactactcc gtacact                                               27

<210> SEQ ID NO 171
<211> LENGTH: 9
<212> TYPE: PRT
<213> ORGANISM: Artificial Sequence
<220> FEATURE:
<223> OTHER INFORMATION: Synthetic

<400> SEQUENCE: 171

Gln Gln Tyr Tyr Thr Thr Pro Tyr Thr
 1               5

<210> SEQ ID NO 172
<211> LENGTH: 354
<212> TYPE: DNA
<213> ORGANISM: Artificial Sequence
<220> FEATURE:
<223> OTHER INFORMATION: Synthetic

<400> SEQUENCE: 172
gaggtgcagc tggtggagtc tgggggaggc ttggtacagc ctggggggtc cctgagactc            60
tcctgtgcag cctctggatt cacctttaac aactatgcca tgaactgggt ccgccaggct           120
ccaggaaagg gactggactg ggtctcaact attagtggta gcgtggtgta caaactactac          180 gcagactccg tgaagggccg tttcattatt tcccgagaca gttccaaaca cacgctgtat           240
ctgcaaatga acagcctgag agccgaggac acggccgtat attactgtgc gaaagattct           300
aactggggaa atttcgatct ctggggccgt ggcaccctgg tcactgtctc ctca                 354

<210> SEQ ID NO 173
<211> LENGTH: 118
<212> TYPE: PRT
<213> ORGANISM: Artificial Sequence
<220> FEATURE:
<223> OTHER INFORMATION: Synthetic

<400> SEQUENCE: 173

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Asn Asn Tyr
             20                  25                  30

Ala Met Asn Trp Val Arg Gln Ala Pro Gly Lys Gly Leu Asp Trp Val
         35                  40                  45

Ser Thr Ile Ser Gly Ser Gly Gly Thr Thr Asn Tyr Ala Asp Ser Val
     50                  55                  60

Lys Gly Arg Phe Ile Ile Ser Arg Asp Ser Ser Lys His Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Asn Trp Gly Asn Phe Asp Leu Trp Gly Arg Gly Thr
            100                 105                 110

Leu Val Thr Val Ser Ser
            115
```

<210> SEQ ID NO 174
<211> LENGTH: 339
<212> TYPE: DNA
<213> ORGANISM: Artificial Sequence
<220> FEATURE:
<223> OTHER INFORMATION: Synthetic

<400> SEQUENCE: 174

```
gacatcgtga tgacccagtc tccagactcc ctggctgtgt ctctgggcga gagggccacc    60
atcaactgca gtccagccca gagtgtttta tacaggtcca acaataggaa cttcttaggt   120
tggtaccagc agaaaccagg gcagcctcct aatctactca tttactgggc atctacccgg   180
gaatccgggg tccctgaccg attcagtggc agcgggtctg ggacagattt cactctcacc   240
atcagcagcc tgcaggctga agatgtggca gtttattact gtcaacaata ttatactact   300
ccgtacactt ttggccaggg gaccaagctg gagatcaaa                          339
```

<210> SEQ ID NO 175
<211> LENGTH: 113
<212> TYPE: PRT
<213> ORGANISM: Artificial Sequence
<220> FEATURE:
<223> OTHER INFORMATION: Synthetic

<400> SEQUENCE: 175

```
Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Arg
             20                  25                  30

Ser Asn Asn Arg Asn Phe Leu Gly Trp Tyr Gln Gln Lys Pro Gly Gln
         35                  40                  45

Pro Pro Asn Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
```

```
                65                  70                  75                  80
Ile Ser Ser Leu Gln Ala Glu Asp Val Ala Val Tyr Tyr Cys Gln Gln
                    85                  90                  95

Tyr Tyr Thr Thr Pro Tyr Thr Phe Gly Gln Gly Thr Lys Leu Glu Ile
                100                 105                 110

Lys
```

<210> SEQ ID NO 176
<211> LENGTH: 381
<212> TYPE: DNA
<213> ORGANISM: Artificial Sequence
<220> FEATURE:
<223> OTHER INFORMATION: Synthetic

<400> SEQUENCE: 176

```
gagatgcaac tggtggagtc tgggggaggc ttggtccagc ctggggggtc cctgagactc      60
tcctgtgcag cctctggatt cacctttagt agtcactgga tgaagtgggt ccgccaggct     120
ccagggaagg ggctggagtg ggtggccaac ataaaccaag atggaagtga aaatactat      180 gtggactctg tgaagggccg attcaccatc tccagagaca acgccaagaa ctcactgttt     240
ctgcaaatga acagcctgag agccgaggac acggctgtgt attactgtgc gagagatatt     300
gtactaatgg tctatgatat ggactactac tactacggta tggacgtctg gggccaaggg     360
accacggtca ccgtctcctc a                                               381
```

<210> SEQ ID NO 177
<211> LENGTH: 127
<212> TYPE: PRT
<213> ORGANISM: Artificial Sequence
<220> FEATURE:
<223> OTHER INFORMATION: Synthetic

<400> SEQUENCE: 177

```
Glu Met Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser His
                20                  25                  30

Trp Met Lys Trp Val Arg Gln Ala Pro Gly Lys Gly Leu Glu Trp Val
            35                  40                  45

Ala Asn Ile Asn Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                85                  90                  95

Ala Arg Asp Ile Val Leu Met Val Tyr Asp Met Asp Tyr Tyr Tyr Tyr
                100                 105                 110

Gly Met Asp Val Trp Gly Gln Gly Thr Thr Val Thr Val Ser Ser
            115                 120                 125
```

<210> SEQ ID NO 178
<211> LENGTH: 24
<212> TYPE: DNA
<213> ORGANISM: Artificial Sequence
<220> FEATURE:
<223> OTHER INFORMATION: Synthetic

<400> SEQUENCE: 178

```
ggattcacct ttagtagtca ctgg                                             24
```

<210> SEQ ID NO 179
<211> LENGTH: 8
<212> TYPE: PRT
<213> ORGANISM: Artificial Sequence
<220> FEATURE:
<223> OTHER INFORMATION: Synthetic

<400> SEQUENCE: 179

Gly Phe Thr Phe Ser Ser His Trp
 1               5

<210> SEQ ID NO 180
<211> LENGTH: 24
<212> TYPE: DNA
<213> ORGANISM: Artificial Sequence
<220> FEATURE:
<223> OTHER INFORMATION: Synthetic

<400> SEQUENCE: 180
ataaaccaag atggaagtga gaaa                                          24

<210> SEQ ID NO 181
<211> LENGTH: 8
<212> TYPE: PRT
<213> ORGANISM: Artificial Sequence
<220> FEATURE:
<223> OTHER INFORMATION: Synthetic

<400> SEQUENCE: 181

Ile Asn Gln Asp Gly Ser Glu Lys
 1               5

<210> SEQ ID NO 182
<211> LENGTH: 60
<212> TYPE: DNA
<213> ORGANISM: Artificial Sequence
<220> FEATURE:
<223> OTHER INFORMATION: Synthetic

<400> SEQUENCE: 182
gcgagagata ttgtactaat ggtctatgat atggactact actactacgg tatggacgtc    60

<210> SEQ ID NO 183
<211> LENGTH: 20
<212> TYPE: PRT
<213> ORGANISM: Artificial Sequence
<220> FEATURE:
<223> OTHER INFORMATION: Synthetic

<400> SEQUENCE: 183

Ala Arg Asp Ile Val Leu Met Val Tyr Asp Met Asp Tyr Tyr Tyr Tyr
 1               5                  10                  15

Gly Met Asp Val
            20

<210> SEQ ID NO 184
<211> LENGTH: 336
<212> TYPE: DNA
<213> ORGANISM: Artificial Sequence
<220> FEATURE:
<223> OTHER INFORMATION: Synthetic

<400> SEQUENCE: 184
gatattgtga tgactcagtc tccactctcc ctgcccgtca cccctggaga gccggcctcc    60

```
atctcctgca ggtctagtca gagcctcctg catagtaatg gaaacaacta tttggattgg      120
tacctgcaga agccagggca gtctccacag ctcctgatct atttgggttc taatcgggcc      180
tccggggtcc ctgacaggtt cagtggcagt ggatcaggca cagattttac actgaaaatc      240
agcagagtgg aggctgagga tgttggggtt tattactgca tgcaaactct acaaactccg      300
ctcactttcg gcggagggac caaggtggag atcaaa                                336
```

<210> SEQ ID NO 185
<211> LENGTH: 112
<212> TYPE: PRT
<213> ORGANISM: Artificial Sequence
<220> FEATURE:
<223> OTHER INFORMATION: Synthetic

<400> SEQUENCE: 185

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100                 105                 110

<210> SEQ ID NO 186
<211> LENGTH: 33
<212> TYPE: DNA
<213> ORGANISM: Artificial Sequence
<220> FEATURE:
<223> OTHER INFORMATION: Synthetic

<400> SEQUENCE: 186
cagagcctcc tgcatagtaa tggaaacaac tat                                    33

<210> SEQ ID NO 187
<211> LENGTH: 11
<212> TYPE: PRT
<213> ORGANISM: Artificial Sequence
<220> FEATURE:
<223> OTHER INFORMATION: Synthetic

<400> SEQUENCE: 187

Gln Ser Leu Leu His Ser Asn Gly Asn Asn Tyr
1               5                   10

<210> SEQ ID NO 188
<211> LENGTH: 9
<212> TYPE: DNA
<213> ORGANISM: Artificial Sequence
<220> FEATURE:
<223> OTHER INFORMATION: Synthetic

<400> SEQUENCE: 188 ttgggttct                                                                9

<210> SEQ ID NO 189
<211> LENGTH: 3
<212> TYPE: PRT
<213> ORGANISM: Artificial Sequence
<220> FEATURE:
<223> OTHER INFORMATION: Synthetic

<400> SEQUENCE: 189

Leu Gly Ser
 1

<210> SEQ ID NO 190
<211> LENGTH: 27
<212> TYPE: DNA
<213> ORGANISM: Artificial Sequence
<220> FEATURE:
<223> OTHER INFORMATION: Synthetic

<400> SEQUENCE: 190
atgcaaactc tacaaactcc gctcact                                          27

<210> SEQ ID NO 191
<211> LENGTH: 9
<212> TYPE: PRT
<213> ORGANISM: Artificial Sequence
<220> FEATURE:
<223> OTHER INFORMATION: Synthetic

<400> SEQUENCE: 191

Met Gln Thr Leu Gln Thr Pro Leu Thr
 1               5

<210> SEQ ID NO 192
<211> LENGTH: 2076
<212> TYPE: DNA
<213> ORGANISM: Homo sapiens

<400> SEQUENCE: 192
atgggcaccg tcagctccag gcggtcctgg tggccgctgc cactgctgct gctgctgctg      60
ctgctcctgg gtcccgcggg cgcccgtgcg caggaggacg aggacggcga ctacgaggag     120
ctggtgctag ccttgcgttc cgaggaggac ggcctggccg aagcacccga gcacggaacc     180
acagccacct tccaccgctg cgccaaggat ccgtggaggt tgcctggcac ctacgtggtg     240
gtgctgaagg aggagccca cctctcgcag tcagagcgca ctgcccgccg cctgcaggcc     300
caggctgccc gccggggata cctcaccaag atcctgcatg tcttccatgg ccttcttcct     360
ggcttcctgg tgaagatgag tggcgacctg ctggagctgg ccttgaagtt gccccatgtc     420
gactacatcg aggaggactc ctctgtcttt gcccagagca tcccgtggaa cctggagcgg     480 attcccctc acggtaccg gcgcgatgaa taccagcccc ccgacggagg cagcctggtg     540
gaggtgtatc tcctagacac cagcatacag agtgaccacc gggaaatcga gggcagggtc     600
atggtcaccg acttcgagaa tgtgcccgag gaggacggga cccgcttcca cagacaggcc     660
agcaagtgtg acagtcatgg cacccacctg gcagggtgg tcagcggccg ggatgccggc     720
gtggccaagg gtgccagcat gcgcagcctg cgcgtgctca actgccaagg gaagggcacg     780
gttagcggca ccctcatagg cctggagttt attcggaaaa gccagctggt ccagcctgtg     840
gggccactgg tggtgctgct gcccctggcg ggtgggtaca gccgcgtcct caacgccgcc     900
tgccagcgcc tggcgagggc tggggtcgtg ctggtcaccg ctgccggcaa cttccgggac     960
gatgcctgcc tctactcccc agcctcagct cccgaggtca tcacagttgg ggccaccaat    1020

```
gcccaggacc agccggtgac cctggggact tggggaccca actttggccg ctgtgtggac    1080
ctctttgccc caggggagga catcattggt gcctccagcg actgcagcac ctgctttgtg    1140
tcacagagtg ggacatcaca ggctgctgcc cacgtggctg gcattgcagc catgatgctg    1200
tctgccgagc cggagctcac cctggccgag ttgaggcaga gactgatcca cttctctgcc    1260
aaagatgtca tcaatgaggc ctggttccct gaggaccagc gggtactgac ccccaacctg    1320
gtggccgccc tgcccccag  cacccatggg gcaggttggc agctgttttg caggactgtg    1380
tggtcagcac actcggggcc tacacggatg ccacagcca  tcgcccgctg cgccccagat    1440
gaggagctgc tgagctgctc cagtttctcc aggagtggga gcggcgggg  cgagcgcatg    1500
gaggcccaag ggggcaagct ggtctgccgg gcccacaacg cttttggggg tgagggtgtc    1560
tacgccattg ccaggtgctg cctgctaccc caggccaact gcagcgtcca cacagctcca    1620
ccagctgagg ccagcatggg gacccgtgtc cactgccacc aacagggcca cgtcctcaca    1680
ggctgcagct cccactggga ggtggaggac cttggcaccc acaagccgcc tgtgctgagg    1740
ccacgaggtc agcccaacca gtgcgtgggc cacaggagg  ccagcatcca cgcttcctgc    1800
tgccatgccc caggtctgga atgcaaagtc aaggagcatg gaatcccggc ccctcaggag    1860
caggtgaccg tggcctgcga ggagggctgg accctgactg gctgcagtgc cctccctggg    1920
acctcccacg tcctgggggc ctacgccgta gacaacacgt gtgtagtcag gagccgggac    1980
gtcagcacta caggcagcac cagcgaagag gccgtgacag ccgttgccat ctgctgccgg    2040
agccggcacc tggcgcaggc ctcccaggag ctccag                             2076
```

<210> SEQ ID NO 193
<211> LENGTH: 692
<212> TYPE: PRT
<213> ORGANISM: Homo sapiens

<400> SEQUENCE: 193

Met Gly Thr Val Ser Ser Arg Arg Ser Trp Trp Pro Leu Pro Leu Leu
 1               5                  10                  15

Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

```
His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
            245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
            290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
            325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
            370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
            405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
            450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
            485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
            565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
            595                 600                 605
```

```
Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
            645                 650                 655

Arg Ser Arg Asp Val Ser Thr Thr Gly Ser Thr Ser Glu Glu Ala Val
        660                 665                 670

Thr Ala Val Ala Ile Cys Cys Arg Ser Arg His Leu Ala Gln Ala Ser
    675                 680                 685

Gln Glu Leu Gln
    690

<210> SEQ ID NO 194
<211> LENGTH: 115
<212> TYPE: PRT
<213> ORGANISM: Artificial Sequence
<220> FEATURE:
<223> OTHER INFORMATION: Synthetic

<400> SEQUENCE: 194

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
    115

<210> SEQ ID NO 195
<211> LENGTH: 8
<212> TYPE: PRT
<213> ORGANISM: Artificial Sequence
<220> FEATURE:
<223> OTHER INFORMATION: Synthetic

<400> SEQUENCE: 195

Gly Phe Thr Phe Ser Arg Asn Ala
1               5

<210> SEQ ID NO 196
<211> LENGTH: 7
<212> TYPE: PRT
<213> ORGANISM: Artificial Sequence
<220> FEATURE:
<223> OTHER INFORMATION: Synthetic

<400> SEQUENCE: 196

Ile Gly Thr Gly Gly Ala Thr
1               5
```

<210> SEQ ID NO 197
<211> LENGTH: 9
<212> TYPE: PRT
<213> ORGANISM: Artificial Sequence
<220> FEATURE:
<223> OTHER INFORMATION: Synthetic

<400> SEQUENCE: 197

Ala Arg Gly Arg Tyr Tyr Phe Asp Tyr
1               5

<210> SEQ ID NO 198
<211> LENGTH: 109
<212> TYPE: PRT
<213> ORGANISM: Artificial Sequence
<220> FEATURE:
<223> OTHER INFORMATION: Synthetic

<400> SEQUENCE: 198

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Phe Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Thr Phe Gly Gln Gly Thr Lys Val Glu Ile Lys
            100                 105

<210> SEQ ID NO 199
<211> LENGTH: 7
<212> TYPE: PRT
<213> ORGANISM: Artificial Sequence
<220> FEATURE:
<223> OTHER INFORMATION: Synthetic

<400> SEQUENCE: 199

Gln Ser Val Ser Ser Ser Tyr
1               5

<210> SEQ ID NO 200
<211> LENGTH: 3
<212> TYPE: PRT
<213> ORGANISM: Artificial Sequence
<220> FEATURE:
<223> OTHER INFORMATION: Synthetic

<400> SEQUENCE: 200

Gly Ala Ser
1

<210> SEQ ID NO 201
<211> LENGTH: 10
<212> TYPE: PRT
<213> ORGANISM: Artificial Sequence
<220> FEATURE:
<223> OTHER INFORMATION: Synthetic

<400> SEQUENCE: 201

Gln Gln Tyr Gly Ser Ser Pro Pro Trp Thr
1               5                   10

<210> SEQ ID NO 202
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly
<220> FEATURE:
<221> NAME/KEY: VARIANT
<222> LOCATION: (2)...(2)
<223> OTHER INFORMATION: Xaa = Phe
<220> FEATURE:
<221> NAME/KEY: VARIANT
<222> LOCATION: (3)...(3)
<223> OTHER INFORMATION: Xaa = Thr
<220> FEATURE:
<221> NAME/KEY: VARIANT
<222> LOCATION: (4)...(4)
<223> OTHER INFORMATION: Xaa = Phe or Ser
<220> FEATURE:
<221> NAME/KEY: VARIANT
<222> LOCATION: (5)...(5)
<223> OTHER INFORMATION: Xaa = Ser
<220> FEATURE:
<221> NAME/KEY: VARIANT
<222> LOCATION: (6)...(6)
<223> OTHER INFORMATION: Xaa = Ser or Asn
<220> FEATURE:
<221> NAME/KEY: VARIANT
<222> LOCATION: (7)...(7)
<223> OTHER INFORMATION: Xaa = Tyr or Phe
<220> FEATURE:
<221> NAME/KEY: VARIANT
<222> LOCATION: (8)...(8)
<223> OTHER INFORMATION: Xaa = Asp, Leu, or Gly

<400> SEQUENCE: 202

Xaa Xaa Xaa Xaa Xaa Xaa Xaa Xaa
1               5

<210> SEQ ID NO 203
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ile
<220> FEATURE:
<221> NAME/KEY: VARIANT
<222> LOCATION: (2)...(2)
<223> OTHER INFORMATION: Xaa = Ser, Gln, Asp, or Trp
<220> FEATURE:
<221> NAME/KEY: VARIANT
<222> LOCATION: (3)...(3)
<223> OTHER INFORMATION: Xaa = Ser, Glu, Thr, or Phe
<220> FEATURE:
<221> NAME/KEY: VARIANT
<222> LOCATION: (4)...(4)
<223> OTHER INFORMATION: Xaa = Asp or Ala
<220> FEATURE:
<221> NAME/KEY: VARIANT
<222> LOCATION: (5)...(5)
<223> OTHER INFORMATION: Xaa = Gly or Glu
<220> FEATURE:
<221> NAME/KEY: VARIANT
<222> LOCATION: (6)...(6)
<223> OTHER INFORMATION: Xaa = Arg, Ile, or absent

```
<220> FEATURE:
<221> NAME/KEY: VARIANT
<222> LOCATION: (7)...(7)
<223> OTHER INFORMATION: Xaa = Asp or Glu
<220> FEATURE:
<221> NAME/KEY: VARIANT
<222> LOCATION: (8)...(8)
<223> OTHER INFORMATION: Xaa = Lys or Thr

<400> SEQUENCE: 203

Xaa Xaa Xaa Xaa Xaa Xaa Xaa Xaa
 1               5

<210> SEQ ID NO 204
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ala or Thr
<220> FEATURE:
<221> NAME/KEY: VARIANT
<222> LOCATION: (2)...(2)
<223> OTHER INFORMATION: Xaa = Lys or Arg
<220> FEATURE:
<221> NAME/KEY: VARIANT
<222> LOCATION: (3)...(3)
<223> OTHER INFORMATION: Xaa = Glu
<220> FEATURE:
<221> NAME/KEY: VARIANT
<222> LOCATION: (4)...(4)
<223> OTHER INFORMATION: Xaa = Met, Pro, Gly, or Asp
<220> FEATURE:
<221> NAME/KEY: VARIANT
<222> LOCATION: (5)...(5)
<223> OTHER INFORMATION: Xaa = Val, Ser, Lys, Arg, or absent
<220> FEATURE:
<221> NAME/KEY: VARIANT
<222> LOCATION: (6)...(6)
<223> OTHER INFORMATION: Xaa = Tyr, His, Asn, or absent
<220> FEATURE:
<221> NAME/KEY: VARIANT
<222> LOCATION: (7)...(7)
<223> OTHER INFORMATION: Xaa = Tyr
<220> FEATURE:
<221> NAME/KEY: VARIANT
<222> LOCATION: (8)...(8)
<223> OTHER INFORMATION: Xaa = Asp or Glu
<220> FEATURE:
<221> NAME/KEY: VARIANT
<222> LOCATION: (9)...(9)
<223> OTHER INFORMATION: Xaa = Ile
<220> FEATURE:
<221> NAME/KEY: VARIANT
<222> LOCATION: (10)...(10)
<223> OTHER INFORMATION: Xaa = Leu
<220> FEATURE:
<221> NAME/KEY: VARIANT
<222> LOCATION: (11)...(11)
<223> OTHER INFORMATION: Xaa = Thr
<220> FEATURE:
<221> NAME/KEY: VARIANT
<222> LOCATION: (12)...(12)
<223> OTHER INFORMATION: Xaa = Gly
<220> FEATURE:
<221> NAME/KEY: VARIANT
<222> LOCATION: (13)...(13)
<223> OTHER INFORMATION: Xaa = Tyr, Asp, or His
<220> FEATURE:
<221> NAME/KEY: VARIANT
<222> LOCATION: (14)...(14)
<223> OTHER INFORMATION: Xaa = His, Asp, Tyr, or absent
<220> FEATURE:
<221> NAME/KEY: VARIANT
```

```
<222> LOCATION: (15)...(15)
<223> OTHER INFORMATION: Xaa = Asn, Tyr, His, or absent
<220> FEATURE:
<221> NAME/KEY: VARIANT
<222> LOCATION: (16)...(16)
<223> OTHER INFORMATION: Xaa = Tyr
<220> FEATURE:
<221> NAME/KEY: VARIANT
<222> LOCATION: (17)...(17)
<223> OTHER INFORMATION: Xaa = Tyr or His
<220> FEATURE:
<221> NAME/KEY: VARIANT
<222> LOCATION: (18)...(18)
<223> OTHER INFORMATION: Xaa = Gly or Ala
<220> FEATURE:
<221> NAME/KEY: VARIANT
<222> LOCATION: (19)...(19)
<223> OTHER INFORMATION: Xaa = Met
<220> FEATURE:
<221> NAME/KEY: VARIANT
<222> LOCATION: (20)...(20)
<223> OTHER INFORMATION: Xaa = Asp
<220> FEATURE:
<221> NAME/KEY: VARIANT
<222> LOCATION: (21)...(21)
<223> OTHER INFORMATION: Xaa = Val or Ile

<400> SEQUENCE: 204

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa
            20

<210> SEQ ID NO 205
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Gly or Ala
<220> FEATURE:
<221> NAME/KEY: VARIANT
<222> LOCATION: (3)...(3)
<223> OTHER INFORMATION: Xaa = Ile
<220> FEATURE:
<221> NAME/KEY: VARIANT
<222> LOCATION: (4)...(4)
<223> OTHER INFORMATION: Xaa = Asn or Arg
<220> FEATURE:
<221> NAME/KEY: VARIANT
<222> LOCATION: (5)...(5)
<223> OTHER INFORMATION: Xaa = Asn
<220> FEATURE:
<221> NAME/KEY: VARIANT
<222> LOCATION: (6)...(6)
<223> OTHER INFORMATION: Xaa = Tyr or Asp

<400> SEQUENCE: 205

Xaa Xaa Xaa Xaa Xaa Xaa
 1               5

<210> SEQ ID NO 206
<211> LENGTH: 3
<212> TYPE: PRT
<213> ORGANISM: Artificial Sequence
<220> FEATURE:
<223> OTHER INFORMATION: Synthetic
```

```
<220> FEATURE:
<221> NAME/KEY: VARIANT
<222> LOCATION: (1)...(1)
<223> OTHER INFORMATION: Xaa = Thr or Ala
<220> FEATURE:
<221> NAME/KEY: VARIANT
<222> LOCATION: (2)...(2)
<223> OTHER INFORMATION: Xaa = Ala or Thr
<220> FEATURE:
<221> NAME/KEY: VARIANT
<222> LOCATION: (3)...(3)
<223> OTHER INFORMATION: Xaa = Ser or Phe

<400> SEQUENCE: 206

Xaa Xaa Xaa
 1

<210> SEQ ID NO 207
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln or Leu
<220> FEATURE:
<221> NAME/KEY: VARIANT
<222> LOCATION: (2)...(2)
<223> OTHER INFORMATION: Xaa = Gln
<220> FEATURE:
<221> NAME/KEY: VARIANT
<222> LOCATION: (3)...(3)
<223> OTHER INFORMATION: Xaa = Tyr, His, or Asp
<220> FEATURE:
<221> NAME/KEY: VARIANT
<222> LOCATION: (4)...(4)
<223> OTHER INFORMATION: Xaa = Asn or Tyr
<220> FEATURE:
<221> NAME/KEY: VARIANT
<222> LOCATION: (5)...(5)
<223> OTHER INFORMATION: Xaa = Thr or Ser
<220> FEATURE:
<221> NAME/KEY: VARIANT
<222> LOCATION: (6)...(6)
<223> OTHER INFORMATION: Xaa = Tyr, Asn, or His
<220> FEATURE:
<221> NAME/KEY: VARIANT
<222> LOCATION: (7)...(7)
<223> OTHER INFORMATION: Xaa = Pro
<220> FEATURE:
<221> NAME/KEY: VARIANT
<222> LOCATION: (8)...(8)
<223> OTHER INFORMATION: Xaa = Leu, Phe, Arg, or absent
<220> FEATURE:
<221> NAME/KEY: VARIANT
<222> LOCATION: (9)...(9)
<223> OTHER INFORMATION: Xaa = Thr

<400> SEQUENCE: 207

Xaa Xaa Xaa Xaa Xaa Xaa Xaa Xaa Xaa
 1               5
```

METHOD OF TREATING STRESS HYPERGLYCEMIA WITH HUMAN ANTIBODIES TO THE GLUCAGON RECEPTOR

CROSS-REFERENCE TO RELATED APPLICATIONS

This application is a divisional of U.S. patent application Ser. No. 13/900,275, filed on May 22, 2013, now U.S. Pat. No. 8,771,696; which is a continuation-in-part of U.S. patent application Ser. No. 13/301,944, filed on Nov. 22, 2011, now U.S. Pat. No. 8,545,847, issued Oct. 1, 2013; which claims the benefit under 35 U.S.C. §119(e) of U.S. provisional application Ser. No. 61/416,409, filed Nov. 23, 2010; U.S. provisional application Ser. No. 61/481,958, filed May 3, 2011; and U.S. provisional application Ser. No. 61/551,032, filed Oct. 25, 2011. U.S. patent application Ser. No. 13/900,275 claims the benefit under 35 U.S.C. §119(e) of U.S. provisional application Ser. No. 61/650,966, filed May 23, 2012; and U.S. provisional application Ser. No. 61/787,748, filed Mar. 15, 2013. The disclosures of all the foregoing are herein specifically incorporated by reference in their entireties.

FIELD OF THE INVENTION

The present invention is related to methods of using a glucagon receptor antagonist for treating stress hyperglycemia in critically ill and non-critically ill patients suffering from such condition.

STATEMENT OF RELATED ART

Glucagon is a 29 amino acid hormone produced by the alpha cells of pancreatic islets. Glucagon maintains normal levels of glucose in animals, including humans, by counterbalancing the effects of insulin. It is an imbalance of glucagon and insulin that may play an important role in several diseases, such as diabetes mellitus and diabetic ketoacidosis. In particular, studies have shown that higher basal glucagon levels and lack of suppression of postprandial glucagon secretion contribute to diabetic conditions in humans (Muller et al., N Eng J Med 283: 109-115 (1970)).

It is believed that glucagon's effects on elevating blood glucose levels are mediated in part by the activation of certain cellular pathways following the binding of glucagon (GCG) to its receptor (designated GCGR). GCGR is a member of the secretin subfamily (family B) of G-protein-coupled receptors and is predominantly expressed in the liver. The binding of glucagon to its receptor triggers a G-protein signal transduction cascade, activating intracellular cyclic AMP and leading to an increase in glucose output through de novo synthesis (gluconeogenesis) and glycogen breakdown (glycogenolysis) (Wakelam et al., Nature, (1986) 323:68-71; Unson et al., Peptides, (1989), 10:1171-1177; and Pittner and Fain, Biochem. J. (1991), 277:371-378).

The rat glucagon receptor was first isolated and purified by Jelinek et al (Jelinek, L. J. et al. (1993) *Science* 259(5101): 1614-1616). Subsequently, the rat sequence was used to identify and clone the 477 amino acid human glucagon receptor sequence (Lok, S. et al. (1994) *Gene* 140:203-209; MacNeil, D. J. et al. (1994) *Biochem. and Biophys. Res. Comm*). U.S. Pat. No. 5,776,725 discloses an isolated nucleic acid sequence encoding a human or rat glucagon receptor.

Targeting glucagon production or function with a glucagon receptor antagonist, such as an anti-GCGR antibody, may be one method of controlling and lowering blood glucose, and as such, may prove useful for treating diseases such as diabetes mellitus or diabetic ketoacidosis. Furthermore, by lowering glucose levels, it may be possible to prevent or ameliorate certain of the long-term complications associated with elevated glucose levels in diabetic patients.

Early studies demonstrated that polyclonal antibodies to the rat glucagon receptor were able to block glucagon binding (Unson, C. G. (1996) *PNAS* 93(1):310-315). Monoclonal antibodies to the human glucagon receptor were described by Buggy et al. (Buggy, J. J. et al. (1995) *J. Biol. Chem.* 270(13): 7474; Buggy, J. J. et al. (1996) *Horm Metab Res.* 28(5):215-9). The antibody described by Buggy et al. competed with glucagon for the hormone binding site of the receptor and recognized both the human and rat glucagon receptors, but not the mouse receptor. Wright et al. disclose a monoclonal antibody raised in a mouse against the human glucagon receptor and conducted detailed protein structure determination of the monoclonal antibody to the receptor (Wright, L. M. (2000) *Acta Crystallographica Section D.* 56(5): 573-580). Other antibodies to the glucagon receptor are described in U.S. Pat. Nos. 5,770,445 and 7,947,809; European patent application EP2074149A2; EP patent EP0658200B1; US patent publications 2009/0041784; 2009/0252727; and 2011/0223160; and PCT publication WO2008/036341.

Stress hyperglycemia (also referred to as stress-induced hyperglycemia), which is defined as a transient increase in blood glucose (>140 mg/dL), is a condition that is temporally linked to the stress of an acute injury or illness. This common medical condition occurs frequently in the diabetic and non-diabetic hospitalized patient and requires prompt therapeutic intervention (Kitabchi A E, Umpierrez G E, Miles J M, Fisher J N, Diabetes Care, (2009), July; 32(7):1335-43; Baker E H, Janaway C H, Philips B J, Brennan A L, Baines D L, Wood D M, et al., Thorax, (2006), April; 61(4):284-9). Serious medical and surgical conditions associated with stress hyperglycemia include myocardial infarction, burns, and cardiopulmonary bypass surgery (Rocha D M, Santeusanio F, Faloona G R, Unger R H, N Engl J. Med. (1973), April 5; 288(14): 700-3). Stress hyperglycemia also occurs in non-critically ill patients, for example, in those admitted for exacerbation of chronic obstructive pulmonary disease (Oshima C, Kaneko T, Tsuruta R, Oda Y, Miyauchi T, Fujita M, et al., Resuscitation, (2010), February 81(2):187-92). In hospitalized patients, stress hyperglycemia is associated with substantial increases in infections, dialysis, blood transfusions, polyneuropathy, and other medical complications including death (up to 18-fold).

Stress hyperglycemia has increasingly been the focus of clinical investigations that demonstrate reductions in the aforementioned medical complications with intensive insulin therapy. However, intensive insulin therapy is associated with a substantial risk of hypoglycemia, which greatly reduces the medical benefits of therapy. As a result, current practice guidelines have been revised to target higher blood glucose levels in order to lower the risk of hypoglycemia, but this approach may limit the benefit of therapy (Kitabchi A E, Umpierrez G E, Miles J M, Fisher J N, Diabetes Care, (2009), July 32(7):1335-43; Baker E H, Janaway C H, Philips B J, Brennan A L, Baines D L, Wood D M, et al., Thorax, (2006), April 61(4):284-9).

Studies in patients admitted for conditions associated with stress hyperglycemia have demonstrated sustained glucagon elevations up to 10-fold above the normal levels (Rocha D M, Santeusanio F, Faloona G R, Unger R H, N Engl J. Med. (1973), April 5; 288(14):700-3); Oshima C, Kaneko T, Tsuruta R, Oda Y, Miyauchi T, Fujita M, et al., Resuscitation, (2010), February 81(2):187-92). In these settings, elevated glucagon may contribute to elevated blood glucose levels and may hamper achieving target glycemic control.

Currently, there are no therapies specifically approved by regulatory agencies to prevent the onset of, or to treat stress hyperglycemia. Stress hyperglycemia in patients who are critically ill represents a serious unmet medical need for several reasons. In particular, these patients have a high risk for imminent death since existing therapies, i.e., intensive insulin, may paradoxically increase the risk for death by causing severe hypoglycemia. Moreover, the etiology of stress hyperglycemia is multifactorial and insulin therapy alone may be insufficient for optimal control. Furthermore, while non-critically ill patients may have a low risk for death, they may still benefit from improved metabolic control and would thus experience lower morbidity.

Therefore, there is a need for new therapies, which may be used alone, or as adjunct therapy with other glucose lowering agents for treating stress hyperglycemia in order to reduce the risk of hypoglycemic episodes and to reduce the morbidity and mortality associated with this condition.

BRIEF SUMMARY OF THE INVENTION

In a first aspect, the invention provides fully human monoclonal antibodies (mAbs) and antigen-binding fragments thereof that bind to the human glucagon receptor (hGCGR) and inhibit or block its activity, for example, block the binding of glucagon to its receptor, thereby blocking the elevation of blood glucose levels. The antibodies or antigen binding fragments thereof may be useful for lowering blood glucose levels in a subject that suffers from a disease characterized by increased blood glucose levels, such as diabetes mellitus. The antibodies may also be used to treat a wide range of conditions and disorders in which blocking the interaction of glucagon with the glucagon receptor is desired, thereby having a beneficial effect. The antibodies may ultimately be used to prevent the long-term complications associated with elevated blood glucose levels in diabetic patients, or to ameliorate at least one symptom associated with elevated blood glucose levels in diabetic patients. The antibodies of the present invention may also be used to address the unmet need for new therapies to prevent the onset of stress hyperglycemia, or to treat stress hyperglycemia, when used alone to lower blood glucose levels, or as adjunct therapy with at least one other glucose lowering agent, for example, insulin. Furthermore, the antibodies of the present invention may prove beneficial in lowering blood glucose levels without the risk of inducing hypoglycemia in patients suffering from stress hyperglycemia. In addition, the use of the antibodies of the invention may prove beneficial in lowering the risk of infections, organ failure, or morbidity and/or mortality in patients suffering from stress hyperglycemia.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

In one embodiment, the invention provides an isolated human antibody or antigen-binding fragment thereof that specifically binds human glucagon receptor (hGCGR), wherein the antibody binds an ectodomain and/or an extracellular (EC) loop of human GCGR, wherein the ectodomain is the N-terminal domain of GCGR and wherein the EC loop is one or more of EC1, EC2 and EC3.

In one embodiment, the invention provides an antibody or fragment thereof, which binds the N-terminal domain comprising amino acid residues ranging from about amino acid residue number 27 to about amino acid residue 144 of SEQ ID NO: 153, or binds an EC loop of hGCGR, wherein the EC loop is one or more of EC1, EC2, and EC3, wherein EC1 comprises amino acid residues ranging from about amino acid residue 194 to about amino acid residue 226 of SEQ ID NO: 153; EC2 comprises amino acid residues ranging from about amino acid residue 285 to about amino acid residue 305 of SEQ ID NO: 153; and EC3 comprises amino acid residues ranging from about amino acid residue 369 to about amino acid residue 384 of SEQ ID NO: 153.

In one embodiment, the human antibody or antigen-binding fragment of a human antibody that binds hGCGR, comprises a heavy chain variable region (HCVR) having an amino acid sequence selected from the group consisting of SEQ ID NO: 2, 18, 34, 50, 66, 70, 86, 90, 106, 110, 126, 130 and 146, or a substantially similar sequence thereof having at least 90%, at least 95%, at least 98% or at least 99% sequence identity. In certain embodiments, the antibody or antigen-binding fragment of an antibody that binds hGCGR comprises a HCVR having an amino acid sequence selected from the group consisting of SEQ ID NO: 34, 70, 86, 110 and 126, or a substantially similar sequence thereof having at least 90%, at least 95%, at least 98% or at least 99% sequence identity.

In one embodiment, the human antibody or antigen-binding fragment of a human antibody that binds hGCGR comprises a light chain variable region (LCVR) having an amino acid sequence selected from the group consisting of SEQ ID NO: 10, 26, 42, 58, 68, 78, 88, 98, 108, 118, 128, 138 and 148, or a substantially similar sequence thereof having at least 90%, at least 95%, at least 98% or at least 99% sequence identity. In certain embodiments, the antibody or antigen-binding fragment of an antibody that binds hGCGR comprises a LCVR having an amino acid sequence selected from the group consisting of SEQ ID NO: 42, 78, 88, 118 and 128, or a substantially similar sequence thereof having at least 90%, at least 95%, at least 98% or at least 99% sequence identity.

In certain embodiments, the human antibody or fragment thereof that binds hGCGR comprises a HCVR/LCVR amino acid sequence pair selected from the group consisting of SEQ ID NO: 2/10, 18/26, 34/42, 50/58, 66/68, 70/78, 86/88, 90/98, 106/108, 110/118, 126/128, 130/138, and 146/148. In certain embodiments, the HCVR/LCVR amino acid sequence pair is selected from the group consisting of SEQ ID NO: 34/42, 70/78, 86/88, 110/118 and 126/128.

In a related embodiment, the invention includes an antibody or antigen-binding fragment of an antibody which specifically binds hGCGR, wherein the antibody or fragment thereof comprises the heavy and light chain CDR domains contained within heavy and light chain sequence pairs selected from the group consisting of SEQ ID NO: 2/10, 18/26, 34/42, 50/58, 66/68, 70/78, 86/88, 90/98, 106/108, 110/118, 126/128, 130/138 and 146/148. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273: 927-948 (1997); and Martin et al., *Proc. Natl. Acad. Sci. USA* 86:9268-9272 (1989). Public databases are also available for identifying CDR sequences within an antibody.

In certain embodiments, the present invention provides an isolated human antibody or an antigen-binding fragment thereof that binds specifically to hGCGR, wherein the antibody comprises a HCVR comprising the three heavy chain CDRs (HCDR1, HCDR2 and HCDR3) contained within the HCVR sequence selected from the group consisting of SEQ ID NO: 2, 18, 34, 50, 66, 70, 86, 90, 106, 110, 126, 130 and 146; and a LCVR comprising the three light chain CDRs (LCDR1, LCDR2 and LCDR3) contained within the LCVR sequences selected from the group consisting of SEQ ID NO: 10, 26, 42, 58, 68, 78, 88, 98, 108, 118, 128, 138 and 148.

In one embodiment, the present invention provides an isolated human antibody or antigen-binding fragment of a human antibody that binds hGCGR, comprising a HCDR3 domain having an amino acid sequence selected from the group consisting of SEQ ID NO: 8, 24, 40, 56, 76, 96, 116 and 136, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 84, 104, 124 and 144, or a substantially similar sequence thereof having at least 90%, at least 95%, at least 98% or at least 99% sequence identity.

In one embodiment, the invention provides an antibody or fragment thereof that further comprises a HCDR1 domain having an amino acid sequence selected from the group consisting of SEQ ID NO: 4, 20, 36, 52, 72, 92, 112 and 132, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 74, 94, 114 and 134, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 80, 100, 120 and 140, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 82, 102, 122 and 142, or a substantially similar sequence thereof having at least 90%, at least 95%, at least 98% or at least 99% sequence identity.

In one embodiment, the antibody or antigen-binding fragment of an antibody comprises:

(a) a HCDR3 domain having an amino acid sequence selected from the group consisting of SEQ ID NO: 8, 24, 40, 56, 76, 96, 116 and 136; and (b) a LCDR3 domain having an amino acid sequence selected from the group consisting of SEQ ID NO: 16, 32, 48, 64, 84, 104, 124 and 144.

In one embodiment, the antibody or antigen-binding fragment of the antibody further comprises:

(c) a HCDR1 domain having an amino acid sequence selected from the group consisting of SEQ ID NO: 4, 20, 36, 52, 72, 92, 112 and 132;

(d) a HCDR2 domain having an amino acid sequence selected from the group consisting of SEQ ID NO: 6, 22, 38, 54, 74, 94, 114 and 134;

(e) a LCDR1 domain having an amino acid sequence selected from the group consisting of SEQ ID NO: 12, 28, 44, 60, 80, 100, 120 and 140; and (f) a LCDR2 domain having an amino acid sequence selected from the group consisting of SEQ ID NO: 14, 30, 46, 62, 82, 102, 122 and 142.

In one embodiment, the antibody or antigen-binding fragment thereof comprises a HCVR comprising a HCDR1 domain having an amino acid sequence selected from one of SEQ ID NO: 4, 20, 36, 52, 72, 92, 112 and 132; a HCDR2 domain having an amino acid sequence selected from one of SEQ ID NO: 6, 22, 38, 54, 74, 94, 114 and 134; a HCDR3 domain having an amino acid sequence selected from one of SEQ ID NOs: 8, 24, 40, 56, 76, 96, 116 and 136; and a LCVR comprising a LCDR1 domain having an amino acid sequence selected from one of SEQ ID NO: 12, 28, 44, 60, 80, 100, 120 and 140; a LCDR2 domain having an amino acid sequence selected from one of SEQ ID NO: 14, 30, 46, 62, 82, 102, 122 and 142; and a LCDR3 domain having an amino acid sequence selected from one of SEQ ID NO: 16, 32, 48, 64, 84, 104, 124 and 144.

In certain embodiments, the human antibody or antigen-binding fragment of a human antibody that binds to human GCGR comprises a HCDR3/LCDR3 amino acid sequence pair selected from the group consisting of SEQ ID NO: 8/16, 24/32, 40/48, 56/64, 76/84, 96/104, 116/124 and 136/144. Non-limiting examples of anti-GCGR antibodies having these HCDR3/LCDR3 pairs are the antibodies designated H4H1345N, H4H1617N, H4H1765N, H4H1321B and H4H1321P, H4H1327B and H4H1327P, H4H1328B and H4H1328P, H4H1331B and H4H1331P, H4H1339B and H4H1339P, respectively.

In one embodiment, the human antibody or antigen binding fragment thereof comprises the HCDR1, HCDR2 and HCDR3 amino acid sequences of SEQ ID NO: 4, 6 and 8, respectively and LCDR1, LCDR2 and LCDR3 amino acid sequences of SEQ ID NO: 12, 14 and 16, respectively.

In one embodiment, the human antibody or antigen binding fragment thereof comprises the HCDR1, HCDR2 and HCDR3 amino acid sequences of SEQ ID NO: 20, 22 and 24, respectively and LCDR1, LCDR2 and LCDR3 amino acid sequences of SEQ ID NO: 28, 30 and 32, respectively.

In one embodiment, the human antibody or antigen binding fragment thereof comprises the HCDR1, HCDR2 and HCDR3 amino acid sequences of SEQ ID NO: 36, 38 and 40, respectively and LCDR1, LCDR2 and LCDR3 amino acid sequences of SEQ ID NO: 44, 46 and 48, respectively.

In one embodiment, the human antibody or antigen binding fragment thereof comprises the HCDR1, HCDR2 and HCDR3 amino acid sequences of SEQ ID NO: 52, 54 and 56, respectively and LCDR1, LCDR2 and LCDR3 amino acid sequences of SEQ ID NO: 60, 62 and 64, respectively.

In one embodiment, the human antibody or antigen binding fragment thereof comprises the HCDR1, HCDR2 and HCDR3 amino acid sequences of SEQ ID NO: 72, 74 and 76, respectively and LCDR1, LCDR2 and LCDR3 amino acid sequences of SEQ ID NO: 80, 82 and 84, respectively.

In one embodiment, the human antibody or antigen binding fragment thereof comprises the HCDR1, HCDR2 and HCDR3 amino acid sequences of SEQ ID NO: 92, 94 and 96, respectively and LCDR1, LCDR2 and LCDR3 amino acid sequences of SEQ ID NO: 100, 102 and 104, respectively.

In one embodiment, the human antibody or antigen binding fragment thereof comprises the HCDR1, HCDR2 and HCDR3 amino acid sequences of SEQ ID NO: 112, 114 and 116, respectively and LCDR1, LCDR2 and LCDR3 amino acid sequences of SEQ ID NO: 120, 122 and 124, respectively.

In one embodiment, the human antibody or antigen binding fragment thereof comprises the HCDR1, HCDR2 and HCDR3 amino acid sequences of SEQ ID NO: 132, 134 and 136, respectively and LCDR1, LCDR2 and LCDR3 amino acid sequences of SEQ ID NO: 140, 142 and 144, respectively.

In one embodiment, the anti-hGCGR antibody or antigen binding fragment thereof comprises a HCDR1 sequence comprising the formula $X^1$—$X^2$—$X^3$—$X^4$—$X^5$—$X^6$—$X^7$—$X^8$ (SEQ ID NO: 202), wherein $X^1$ is Gly, $X^2$ is Phe, $X^3$ is Thr, $X^4$ is Phe or Ser, $X^5$ is Ser, $X^6$ is Ser or Asn, $X^7$ is Tyr or Phe, and $X^8$ is Asp, Leu, or Gly; a HCDR2 sequence comprising the formula $X^1$—$X^2$-$X^3$—$X^4$—$X^5$—$X^6$—$X^7$—$X^8$ (SEQ ID NO: 203), wherein $X^1$ is Ile, $X^2$ is Ser, Gln, Asp, or Trp, $X^3$ is Ser, Glu, Thr, or Phe, $X^4$ is Asp or Ala, $X^5$ is Gly or Glu, $X^6$ is Arg, Ile, or absent, $X^7$ is Asp or Glu, and $X^8$ is Lys or Thr; a HCDR3 sequence comprising the formula $X^1$—$X^2$—$X^3$—$X^4$—$X^5$—$X^6$—$X^7$—$X^8$—$X^9$—$X^{10}$—$X^{11}$—$X^{12}$—$X^{13}$—$X^{14}$—$X^{15}$—$X^{16}$—$X^{17}$—$X^{18}$—$X^{19}$—$X^{20}$—$X^{21}$ (SEQ ID NO: 204), wherein $X^1$ is Ala or Thr, $X^2$ is Lys or Arg, $X^3$ is Glu, $X^4$ is Met, Pro, Gly, or Asp, $X^5$ is Val, Ser, Lys, Arg, or absent, $X^6$ is Tyr, His, Asn, or absent, $X^7$ is Tyr, $X^8$ is Asp or Glu, $X^9$ is Ile, $X^{10}$ is Leu, $X^{11}$ is Thr, $X^{12}$ is Gly, $X^{13}$ is Tyr, Asp, or His, $X^{14}$ is His, Asp, Tyr, or absent, $X^{15}$ is Asn, Tyr, His, or absent, $X^{16}$ is Tyr, $X^{17}$ is Tyr or His, $X^{18}$ is Gly or Ala, $X^{19}$ is Met, $X^{20}$ is Asp and $X^{21}$ is Val or Ile; a LCDR1 sequence comprising the formula $X^1$—$X^2$—$X^3$—$X^4$—$X^5$—$X^6$ (SEQ ID NO: 205), wherein $X^1$ is Gln, $X^2$ is Gly or Ala, $X^3$ is Ile, $X^4$ is Asn or Arg, $X^5$ is Asn, and $X^6$ is Tyr or Asp; a LCDR2 sequence comprising the formula $X^1$—$X^2$—$X^3$ (SEQ ID NO: 206), wherein $X^1$ is Thr or Ala, $X^2$ is Ala or Thr, and $X^3$ is Ser or Phe; and a LCDR3 sequence comprising the formula $X^1$—$X^2$—$X^3$—$X^4$—$X^5$—$X^6$—$X^7$—$X^8$—$X^9$ (SEQ ID NO: 207), wherein $X^1$ is Gln or Leu, $X^2$ is Gln, $X^3$ is Tyr, His, or Asp, $X^4$ is Asn or Tyr, $X^5$ is Thr or Ser, $X^6$ is Tyr, Asn, or His, $X^7$ is Pro, $X^8$ is Leu, Phe, Arg, or absent and $X^9$ is Thr.

In one embodiment, the antibody or antigen-binding fragment binds human, monkey, mouse and rat GCGR.

In one embodiment, the antibody or antigen-binding fragment binds human, monkey and mouse GCGR, but does not bind rat GCGR.

In one embodiment, the antibody or antigen-binding fragment binds human, monkey and rat GCGR, but does not bind mouse GCGR.

In one embodiment, the antibody or antigen-binding fragment binds human and monkey GCGR, but does not bind rat or mouse GCGR.

In one embodiment, the antibody or antigen-binding fragment binds human GCGR, but does not bind monkey, mouse or rat GCGR.

In one embodiment, the invention provides a fully human monoclonal antibody or antigen-binding fragment thereof that neutralizes hGCGR activity, wherein the antibody or fragment thereof exhibits one or more of the following characteristics: (i) comprises a HCVR having an amino acid sequence selected from the group consisting of SEQ ID NO: 2, 18, 34, 50, 66, 70, 86, 90, 106, 110, 126, 130 and 146; (ii) comprises a LCVR having an amino acid sequence selected from the group consisting of SEQ ID NO: 10, 26, 42, 58, 68, 78, 88, 98, 108, 118, 128, 138 and 148; (iii) comprises a HCDR3 domain having an amino acid sequence selected from the group consisting of SEQ ID NO: 8, 24, 40, 56, 76, 96, 116 and 136, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 84, 104, 124 and 144, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 72, 92, 112 and 132, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 74, 94, 114 and 134, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 80, 100, 120 and 140, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 82, 102, 122 and 142, or a substantially similar sequence thereof having at least 90%, at least 95%, at least 98% or at least 99% sequence identity; (v) binds any one or more of human, monkey, mouse or rat GCGR; (vi) may or may not block GCGR activity in at least one species other than human; (v) demonstrates a $K_D$ ranging from about $10^{-8}$ to about $10^{-12}$; (vi) lowers blood glucose levels by at least about 25% to about 75% in a mammal experiencing elevated blood glucose levels; (vii) may or may not lower triglyceride levels to levels observed in a normal mammal; or (viii) demonstrates no adverse effect on blood levels of LDL, HDL, or total cholesterol in a mammal.

In another related embodiment, the invention provides an antibody or antigen-binding fragment thereof that competes for specific binding to hGCGR with an antibody or antigen-binding fragment comprising the complementarity determining regions (CDRs) of a heavy chain variable region (HCVR), wherein the HCVR has an amino acid sequence selected from the group consisting of SEQ ID NOs: 2, 18, 34, 50, 66, 70, 86, 90, 106, 110, 126, 130 and 146; and the CDRs of a light chain variable region (LCVR), wherein the LCVR has an amino acid sequence selected from the group consisting of SEQ ID NOs: 10, 26, 42, 58, 68, 78, 88, 98, 108, 118, 128, 138 and 148.

In one embodiment, the invention provides an antibody or antigen-binding fragment thereof that competes for specific binding to hGCGR with an antibody or antigen-binding fragment comprising heavy and light chain CDR domains contained within heavy and light chain sequence pairs selected from the group consisting of SEQ ID NO: 2/10, 18/26, 34/42, 50/58, 66/68, 70/78, 86/88, 90/98, 106/108, 110/118, 126/128, 130/138 and 146/148.

In another related embodiment the invention provides an antibody or antigen-binding fragment thereof that binds the same epitope on hGCGR as an antibody or antigen-binding fragment comprising the complementarity determining regions (CDRs) of a heavy chain variable region (HCVR), wherein the HCVR has an amino acid sequence selected from the group consisting of SEQ ID NOs: 2, 18, 34, 50, 66, 70, 86, 90, 106, 110, 126, 130 and 146; and the CDRs of a light chain variable region (LCVR), wherein the LCVR has an amino acid sequence selected from the group consisting of SEQ ID NOs: 10, 26, 42, 58, 68, 78, 88, 98, 108, 118, 128, 138 and 148.

In one embodiment, the invention provides an antibody or antigen-binding fragment thereof that binds the same epitope on hGCGR that is recognized by an antibody comprising heavy and light chain sequence pairs selected from the group consisting of SEQ ID NO: 2/10, 18/26, 34/42, 50/58, 66/68, 70/78, 86/88, 90/98, 106/108, 110/118, 126/128, 130/138 and 146/148.

In one embodiment, the invention provides for an anti-hGCGR antibody having one or more of the following characteristics:
a) capable of reducing blood glucose levels by about 25% to about 75% for a period of at least 7 days, when administered at a dose ranging from about 1 mg/kg to about 30 mg/kg;
b) capable of resulting in at least a 10% reduction in body weight when administered to a mammal in need of such therapy;
c) capable of reducing blood ketone levels by about 25% to 75% when administered at a dose ranging from about 1 mg/kg to about 30 mg/kg; or
d) capable of reducing blood glucose levels by about 20% to about 40% without causing a significant elevation in blood lipids or cholesterol when administered with an antibody specific for proprotein convertase subtilisin/kexin type (PCSK)-9, and sustaining lowered blood glucose levels for at least 7 days post treatment.

In a second aspect, the invention provides nucleic acid molecules encoding anti-hGCGR antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 69, 85, 89, 105, 109, 125, 129 and 145, or a substantially identical sequence having at least 90%, at least 95%, at least 98%, or at least 99% homology thereof. In one embodiment, the HCVR is encoded by a nucleic acid sequence selected from the group consisting of SEQ ID NO: 33, 69, 85, 109 and 125.

In one embodiment, the antibody or fragment thereof further comprises a LCVR encoded by a nucleic acid sequence selected from the group consisting of SEQ ID NO: 9, 25, 41, 57, 67, 77, 87, 97, 107, 117, 127, 137 and 147, or a substantially identical sequence having at least 90%, at least 95%, at least 98%, or at least 99% homology thereof. In one embodiment, the LCVR is encoded by a nucleic acid sequence selected from the group consisting of SEQ ID NO: 41, 77, 87, 117 and 127.

In one embodiment, the invention also provides an antibody or antigen-binding fragment of an antibody comprising a HCDR3 domain encoded by a nucleotide sequence selected from the group consisting of SEQ ID NO: 7, 23, 39, 55, 75, 95, 115 and 135, or a substantially similar sequence thereof having at least 90%, at least 95%, at least 98% or at least 99% sequence identity; and a LCDR3 domain encoded by a nucleotide sequence selected from the group consisting of SEQ ID NO: 15, 31, 47, 63, 83, 103, 123 and 143, or a substantially similar sequence thereof having at least 90%, at least 95%, at least 98% or at least 99% sequence identity.

In one embodiment, the invention provides an antibody or fragment thereof further comprising a HCDR1 domain encoded by a nucleotide sequence selected from the group consisting of SEQ ID NO: 3, 19, 35, 51, 71, 91, 111 and 131, or a substantially similar sequence thereof having at least 90%, at least 95%, at least 98% or at least 99% sequence identity; a HCDR2 domain encoded by a nucleotide sequence selected from the group consisting of SEQ ID NO: 5, 21, 37, 53, 73, 93, 113 and 133, or a substantially similar sequence thereof having at least 90%, at least 95%, at least 98% or at least 99% sequence identity; a LCDR1 domain encoded by a nucleotide sequence selected from the group consisting of SEQ ID NO: 11, 27, 43, 59, 79, 99, 119 and 139, or a substantially similar sequence thereof having at least 90%, at least 95%, at least 98% or at least 99% sequence identity; and a LCDR2 domain encoded by a nucleotide sequence selected from the group consisting of SEQ ID NO: 13, 29, 45, 61, 81, 101, 121 and 141, or a substantially similar sequence thereof having at least 90%, at least 95%, at least 98% or at least 99% sequence identity.

In a third aspect, the invention features a human anti-hGCGR antibody or antigen-binding fragment of an antibody comprising a HCVR encoded by nucleotide sequence segments derived from $V_H$, $D_H$ and $J_H$ germline sequences, and a LCVR encoded by nucleotide sequence segments derived from $V_K$ and $J_K$ germline sequences, with combinations as shown in Table 2.

The invention encompasses anti-hGCGR antibodies having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277: 26733). In other applications, modification of galactosylation can be made in order to modify complement dependent cytotoxicity (CDC).

In a fourth aspect, the invention features a pharmaceutical composition comprising a recombinant human antibody or fragment thereof, which specifically binds hGCGR, and a pharmaceutically acceptable carrier or diluent.

In one embodiment, the invention features a composition, which is a combination of an antibody or antigen-binding fragment of an antibody of the invention, and a second therapeutic agent. The second therapeutic agent may be any agent that is advantageously combined with the antibody or fragment thereof of the invention.

In one embodiment, the second therapeutic agent may be an agent capable of lowering blood glucose or reducing at least one symptom in a patient suffering from a disease or condition characterized by high blood glucose levels, such as diabetes mellitus.

In certain embodiments, the second therapeutic agent may be an agent that helps to counteract or reduce any possible side effect(s) associated with the antibody or antigen-binding fragment of an antibody of the invention, if such side effect(s) should occur. For example, in the event that any of the anti-hGCGR antibodies increases lipid or cholesterol levels, it may be beneficial to administer a second agent that is effective to lower lipid or cholesterol levels.

The second therapeutic agent may be a small molecule drug, a protein/polypeptide, an antibody, a nucleic acid molecule, such as an anti-sense molecule, or a siRNA. The second therapeutic agent may be synthetic or naturally derived.

In one embodiment, the second therapeutic agent may be a glucagon antagonist, or a second glucagon receptor antagonist, such as another antibody to the glucagon receptor, which is different than the antibodies described herein. It will also be appreciated that the antibodies and pharmaceutically acceptable compositions of the present invention can be employed in combination therapies, that is, the antibodies and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an antibody may be administered concurrently with another agent used to treat the same disorder), or they may achieve different effects (e.g., control of any adverse effects). As used herein, additional therapeutic agents that are normally administered to treat or prevent a particular disease, or condition, are appropriate for the disease, or condition, being treated.

In one embodiment, the anti-hGCGR antibodies of the invention may be used in combination with one or more of the following type 2 diabetes treatments currently available. These include biguanide (metformin), sulfonylureas (such as glyburide, glipizide), peroxisome proliferator-activated receptor (PPAR) gamma agonists (pioglitazone, rosiglitazone); and alpha glucosidase inhibitors (acarbose, voglibose). Additional treatments include injectable treatments such as EXENATIDE® (glucagon-like peptide 1), and SYMLIN® (pramlintide).

In certain embodiments, the composition may include a second agent selected from the group consisting of non-sulfonylurea secretagogues, insulin, insulin analogs, exendin-4 polypeptides, beta 3 adrenoceptor agonists, PPAR agonists, dipeptidyl peptidase IV inhibitors, statins and statin-containing combinations, inhibitors of cholesterol uptake and/or bile acid re-absorption, LDL-cholesterol antagonists, cholesteryl ester transfer protein antagonists, endothelin receptor antagonists, growth hormone antagonists, insulin sensitizers, amylin mimetics or agonists, cannabinoid receptor antagonists, glucagon-like peptide-1 agonists, melanocortins, melanin-concentrating hormone receptor agonists, SNRIs, a fibroblast growth factor 21 (FGF21) mimetic (See, for example, US20110002845 and US20080261236), a fibroblast growth factor receptor 1c (FGFR1c) agonist (See, for example, US20110150901), an inhibitor of advanced glycation end-product formation, such as, but not limited to, aminoguanidine, and protein tyrosine phosphatase inhibitors.

In certain embodiments, the composition may include a second agent to help lower lipid or cholesterol levels and may include an agent such as a 3-hydroxy-3-methylglutaryl-coenzyme A (HMG-CoA) reductase inhibitor (for example, a statin such as atorvastatin, (LIPITOR®), fluvastatin (LESCOL®), lovastatin (MEVACOR®), pitavastatin (LIVALO®), pravastatin (PRAVACHOL®), rosuvastatin (CRESTOR®) and simvastatin (ZOCOR®) and the like.

In certain embodiments, it may be beneficial to administer the antibodies of the invention in combination with any one or more of the following: (1) niacin, which increases lipoprotein catabolism; (2) fibrates or amphipathic carboxylic acids, which reduce low-density lipoprotein (LDL) level, improve high-density lipoprotein (HDL) and triglycerides (TG) levels, and reduce the number of non-fatal heart attacks; and (3) activators of the LXR transcription factor that plays a role in cholesterol elimination such as 22-hydroxycholesterol, or fixed combinations such as VYTORIN®) (ezetimibe plus simvastatin); a statin with a bile resin (e.g., cholestyramine, colestipol, colesevelam), a fixed combination of niacin plus a statin (e.g., niacin with lovastatin); or with other lipid lowering agents such as omega-3-fatty acid ethyl esters (for example, omacor). Furthermore, the second therapeutic agent can be one or more other inhibitors of glucagon or hGCGR, as well as inhibitors of other molecules, such as angiopoietin-like protein 3 (ANGPTL3), angiopoietin-like protein 4 (ANGPTL4), angiopoietin-like protein 5 (ANGPTL5), angiopoietin-like protein 6 (ANGPTL6), which are involved in lipid metabolism, in particular, cholesterol and/or triglyceride homeostasis. Inhibitors of these molecules include small molecules and antibodies that specifically bind to these molecules and block their activity.

In certain embodiments, it may be beneficial to administer the anti-GCGR antibodies of the invention in combination with a nucleic acid that inhibits the activity of hPCSK9, such as an antisense molecule, a double stranded RNA, or a siRNA molecule. Exemplary nucleic acid molecules that inhibit the activity of PCSK9 are described in US2011/0065644, US2011/0039914, US2008/0015162 and US2007/0173473.

In certain embodiments, it may be beneficial to administer the anti-hGCGR antibodies of the invention in combination with an antibody that specifically binds to and inhibits the activity of hPCSK9, wherein such antibody acts to lower lipid or cholesterol levels. Exemplary anti-hPCSK9 antibodies are described in US2010/0166768. The isolated antibody that specifically binds to human PCSK9, or an antigen-binding fragment thereof, may be administered at a dose ranging from about 0.01 mg/kg to about 30 mg/kg. It may be administered as a single dose or as multiple doses. The anti-hPCSK9 antibody may be administered concurrently with the anti-GCGR antibody, or it may be administered prior to, or after the anti-GCGR antibody.

In one embodiment, the second therapeutic agent to be used in combination with an antibody of the invention comprises an isolated antibody that specifically binds to human PCSK9, or an antigen-binding fragment thereof, wherein the anti-hPCSK9 antibody comprises the three heavy chain CDRs (HCDR1, HCDR2 and HCDR3) contained within any one of the HCVR sequences selected from the group consisting of SEQ ID NOs: 173 and 177; and the three light chain CDRs (LCDR1, LCDR2 and LCDR3) contained within any one of the LCVR sequences selected from the group consisting of SEQ ID NOs: 175 and 185.

In one embodiment, the isolated antibody that specifically binds to human PCSK9, or antigen-binding fragment thereof, comprises a heavy chain variable region (HCVR) selected from the group consisting of SEQ ID NO: 173 and 177.

In one embodiment, the isolated antibody that specifically binds to human PCSK9, or antigen-binding fragment thereof, comprises a light chain variable region (LCVR) selected from the group consisting of SEQ ID NO: 175 and 185.

In one embodiment, the isolated antibody that specifically binds to human PCSK9, or antigen-binding fragment thereof, comprises a HCVR having an amino acid sequence selected from the group consisting of SEQ ID NO: 173 and 177 and a LCVR having an amino acid sequence selected from the group consisting of SEQ ID NO: 175 and 185.

In one embodiment, the isolated antibody that specifically binds to human PCSK9, or antigen-binding fragment thereof, comprises a heavy chain variable region (HCVR) and a light chain variable region (LCVR), wherein the HCVR/LCVR sequence pairs are selected from the group consisting of SEQ ID NO: 173/175; and SEQ ID NO: 177/185.

In one embodiment, the isolated antibody that specifically binds to human PCSK9, or antigen-binding fragment thereof, comprises: a HCDR1 comprising an amino acid sequence selected from the group consisting of SEQ ID NO: 161 and 179; a HCDR2 comprising an amino acid sequence selected from the group consisting of SEQ ID NO: 163 and 181; a HCDR3 comprising an amino acid sequence selected from the group consisting of SEQ ID NO: 165 and 183; a LCDR1 comprising an amino acid sequence selected from the group consisting of SEQ ID NO: 167 and 187; a LCDR2 comprising an amino acid sequence selected from the group consisting of SEQ ID NO: 169 and 189 and a LCDR3 comprising an amino acid sequence selected from the group consisting of SEQ ID NO: 171 and 191.

In certain embodiments, the hPCSK9 antibodies to be used in combination with the anti-GCGR antibodies of the invention are encoded by nucleic acid molecules as described herein. For example, in one embodiment, the invention provides an anti-hPCSK9 antibody or fragment thereof comprising a HCVR encoded by a nucleic acid sequence selected from the group consisting of SEQ ID NO: 172 and 176, or a substantially identical sequence having at least 90%, at least 95%, at least 98%, or at least 99% homology thereof, and a LCVR encoded by a nucleic acid sequence selected from the group consisting of SEQ ID NO: 174 and 184, or a substantially identical sequence having at least 90%, at least 95%, at least 98%, or at least 99% homology thereof.

In one embodiment, the invention provides an anti-hPCSK9 antibody to be used in combination with the anti-GCGR antibodies of the invention, wherein the anti-PCSK9 antibody or fragment thereof comprises a HCDR1 domain encoded by a nucleotide sequence selected from the group consisting of SEQ ID NO: 160 and 178, or a substantially similar sequence thereof having at least 90%, at least 95%, at least 98% or at least 99% sequence identity; a HCDR2 domain encoded by a nucleotide sequence selected from the group consisting of SEQ ID NO: 162 and 180, or a substantially similar sequence thereof having at least 90%, at least 95%, at least 98% or at least 99% sequence identity; a HCDR3 domain encoded by a nucleotide sequence selected from the group consisting of SEQ ID NO: 164 and 182, or a substantially similar sequence thereof having at least 90%, at least 95%, at least 98% or at least 99% sequence identity; a LCDR1 domain encoded by a nucleotide sequence selected from the group consisting of SEQ ID NO: 166 and 186, or a substantially similar sequence thereof having at least 90%, at least 95%, at least 98% or at least 99% sequence identity; a LCDR2 domain encoded by a nucleotide sequence selected from the group consisting of SEQ ID NO: 168 and 188, or a substantially similar sequence thereof having at least 90%, at least 95%, at least 98% or at least 99% sequence identity; and a LCDR3 domain encoded by a nucleotide sequence selected from the group consisting of SEQ ID NO: 170 and 190, or a substantially similar sequence thereof having at least 90%, at least 95%, at least 98% or at least 99% sequence identity.

When multiple therapeutics are co-administered, dosages may be adjusted accordingly, as is recognized in the pertinent art.

In a fifth aspect, the invention features methods for inhibiting hGCGR activity using the anti-hGCGR antibody or antigen-binding portion of the antibody of the invention, wherein the therapeutic methods comprise administering a therapeutically effective amount of a pharmaceutical composition comprising the antibody or antigen-binding fragment thereof. The antibodies of the invention may be used to treat any condition or disorder, which is improved, ameliorated, inhibited or prevented by removal, inhibition or reduction of hGCGR activity. It is envisioned that the antibodies of the invention may be used alone, or as adjunct therapy with other agents or methods known to be standard care for treating patients suffering from diseases or conditions characterized in part by elevated blood glucose or ketone levels, such as, but not limited to, diabetes. Such standard therapy may include fluid administration, or administration of any other pharmaceutical agents useful for lowering blood glucose, ketones, or lipids, or for weight reduction.

The anti-hGCGR antibodies of the invention, or antigen-binding fragments thereof, may function to block the interaction between glucagon and its receptor, thereby inhibiting the glucose elevating effects of glucagon. The use of glucagon receptor antagonists, such as the antibodies described herein, may be an effective means of achieving normal levels of glucose, thereby ameliorating, or preventing one or more symptoms of, or long term complications associated with, for example, diabetes. The use of glucagon receptor antagonists, such as the antibodies described herein, may also be an effective means of achieving normal levels of glucose in non-diabetic patients, who experience hyperglycemia as a result of conditions or disorders not related to diabetes, such as perioperative hyperglycemia (hyperglycemia observed in patients just prior to surgery, or after surgery, discussed in greater detail below). In certain embodiments, methods of lowering blood glucose levels or ketone levels in diabetic ketoacidosis are envisioned using the antibodies of the invention. In certain embodiments, methods of treating patients to achieve a reduction in body weight, or to prevent weight gain, or to maintain a normal body weight, are also envisioned using the antibodies of the invention.

The antibodies of the present invention, or antigen-binding fragments thereof, may be useful for ameliorating conditions such as, for example, impaired glucose tolerance, obesity, or for preventing weight gain, or for treating diabetic conditions, or for preventing or reducing the severity of any one or more of the long-term complications associated with diabetes, such as nephropathy, neuropathy, retinopathy, cataracts, stroke, atherosclerosis, impaired wound healing and other complications associated with diabetes, known to those skilled in the art.

In a sixth aspect, the invention features a method for preventing the onset of stress hyperglycemia in a patient, or for treating a patient suffering from stress hyperglycemia (also referred to as "stress-induced hyperglycemia"), the method comprising administering to a patient a therapeutically effective amount of a composition comprising a glucagon receptor antagonist, wherein the patient exhibits elevated levels of blood glucose caused, or exacerbated by, one or more stress-inducing stimulus or one or more glucose elevating stimulus.

In one embodiment, the patient is identified on the basis of having a blood glucose level greater than about 140 mg/dL.

In one embodiment, the stress-inducing stimulus or the glucose elevating stimulus is selected from the group consisting of: pre-existing type 1 or type 2 diabetes; hypertonic dehydration; infusion of catecholamine pressors; glucocorticoid therapy; obesity; aging; excessive dextrose administration; parenteral nutrition, enteral nutrition, pancreatitis; sepsis; stroke; traumatic head injury; hypothermia; hypoxemia; uremia; cirrhosis; anesthesia; pre-operative or post-operative hospital stays (peri-operative hyperglycemia); admission to an emergency room, a trauma center, or an intensive care unit; prolonged hospital stays; surgical procedures; an infection; or a chronic illness.

In one embodiment, the glucagon receptor antagonist used to treat the stress hyperglycemia is an isolated human antibody, or an antigen binding fragment thereof, specific for the human glucagon receptor, wherein the isolated human antibody or the antigen-binding fragment thereof is capable of blocking the binding of glucagon to the glucagon receptor.

In one embodiment, the isolated human antibody or antigen-binding fragment thereof useful for treating stress hyperglycemia comprises the complementarity determining regions (CDRs) of a heavy chain variable region (HCVR), wherein the HCVR has an amino acid sequence selected from the group consisting of SEQ ID NOs: 2, 18, 34, 50, 66, 70, 86, 90, 106, 110, 126, 130 and 146; and the CDRs of a light chain variable region (LCVR), wherein the LCVR has an amino acid sequence selected from the group consisting of SEQ ID NOs: 10, 26, 42, 58, 68, 78, 88, 98, 108, 118, 128, 138 and 148.

In a related embodiment, the isolated human antibody or antigen-binding fragment thereof useful for treating stress hyperglycemia comprises a heavy chain variable region (HCVR) having an amino acid sequence selected from the group consisting of SEQ ID NO: 2, 18, 34, 50, 66, 70, 86, 90, 106, 110, 126, 130 and 146.

In another related embodiment, the isolated human antibody or antigen-binding fragment thereof useful for treating stress hyperglycemia comprises a light chain variable region (LCVR) having an amino acid sequence selected from the group consisting of SEQ ID NO: 10, 26, 42, 58, 68, 78, 88, 98, 108, 118, 128, 138 and 148.

In another related embodiment, the isolated human antibody or antigen-binding fragment thereof useful for treating stress hyperglycemia comprises: (a) a HCVR having an amino acid sequence selected from the group consisting of SEQ ID NO: 2, 18, 34, 50, 66, 70, 86, 90, 106, 110, 126, 130 and 146; and (b) a LCVR having an amino acid sequence selected from the group consisting of SEQ ID NO: 10, 26, 42, 58, 68, 78, 88, 98, 108, 118, 128, 138 and 148.

In another related embodiment, the isolated human antibody or antigen-binding fragment thereof useful for treating stress hyperglycemia comprises:
(a) a HCDR1 domain having an amino acid sequence selected from the group consisting of SEQ ID NO: 4, 20, 36, 52, 72, 92, 112 and 132;
(b) a HCDR2 domain having an amino acid sequence selected from the group consisting of SEQ ID NO: 6, 22, 38, 54, 74, 94, 114 and 134;
(c) a HCDR3 domain having an amino acid sequence selected from the group consisting of SEQ ID NOs: 8, 24, 40, 56, 76, 96, 116 and 136;
(d) a LCDR1 domain having an amino acid sequence selected from the group consisting of SEQ ID NO: 12, 28, 44, 60, 80, 100, 120 and 140;
(f) a LCDR2 domain having an amino acid sequence selected from the group consisting of SEQ ID NO: 14, 30, 46, 62, 82, 102, 122 and 142; and
(g) a LCDR3 domain having an amino acid sequence selected from the group consisting of SEQ ID NO: 16, 32, 48, 64, 84, 104, 124 and 144.

In one embodiment, the isolated human antibody or antigen-binding fragment thereof useful for treating stress hyperglycemia comprises a HCVR/LCVR sequence pair selected from the group consisting of SEQ ID NO: 2/10, 18/26, 34/42, 50/58, 66/68, 70/78, 86/88, 90/98, 106/108, 110/118, 126/128, 130/138, and 146/148.

In one embodiment, the patients who suffer from stress hyperglycemia who may benefit by treatment with an antibody of the invention, as described herein, may be diabetic patients or non-diabetic patients. In certain embodiments, these patients may be critically ill (requiring treatment in an intensive care unit) or non-critically ill (not requiring treatment in an intensive care unit) diabetic or non-diabetic patients.

In certain embodiments, the patients suffering from stress hyperglycemia who are diabetic and who are candidates for therapy with an antibody of the invention may also receive treatment with one or more therapeutic agents selected from the group consisting of insulin, a biguanide (metformin), a sulfonylurea (such as glyburide, glipizide), a PPAR gamma agonist (pioglitazone, rosiglitazone), an alpha glucosidase inhibitor (acarbose, voglibose), SYMLIN® (pramlintide), any GLP-1 compound, or an analogue, an agonist, a derivative, or a secretagogue thereof, and a dipeptidyl peptidase 4 inhibitor.

In certain embodiments, the patients suffering from stress hyperglycemia who are non-diabetic and who are candidates for therapy with an antibody of the invention may also receive treatment with insulin.

In certain embodiments, the anti-GCGR antibodies, or antigen-binding fragments thereof, useful for treating stress hyperglycemia, may lower blood glucose levels in this patient population to levels within the normal range. In one embodiment, the administering of an anti-GCGR antibody, or an antigen-binding fragment thereof, results in lowering the blood glucose level to between about 80 mg/dL to about 180 mg/dL. In one embodiment, the administering of an anti-GCGR antibody, or an antigen-binding fragment thereof, results in lowering the blood glucose level to between about 80 mg/dL to about 140 mg/dL. In another embodiment, the administering of an anti-GCGR antibody, or an antigen-binding fragment thereof, results in lowering the blood glucose level to between about 80 mg/dL to about 110 mg/dL. In another embodiment, the administering of an anti-GCGR antibody, or an antigen-binding fragment thereof, results in lowering the blood glucose level to between about 100 mg/dL to about 140 mg/dL.

In one embodiment, the use of an antibody of the invention alone, or when combined with a standard insulin treatment paradigm, may decrease glucose levels without hypoglycemic risk in diabetic patients.

In one embodiment, the use of an antibody of the invention alone, or when combined with a standard insulin treatment paradigm, may decrease glucose levels without hypoglycemic risk in stress hyperglycemic patients.

In one embodiment, the use of an antibody of the invention, when used alone, or when combined with a standard insulin treatment paradigm, may result in a decreased risk for infection, organ failure, or death in stress hyperglycemic patients.

In one embodiment, the use of an antibody of the invention may reduce blood glucose levels after administration to a diabetic patient.

In one embodiment, the use of an antibody of the invention may reduce blood glucose levels after administration to a patient suffering from stress hyperglycemia.

In one embodiment, the use of an antibody of the invention may result in normalization of blood glucose levels within a few days after administration in diabetic patients, or in patients suffering from stress hyperglycemia.

In certain embodiments, the use of an antibody of the invention alone, or when combined with a standard insulin treatment paradigm, may be expected to improve patient outcomes and/or decrease hospital costs in critically ill and non-critically ill stress hyperglycemic patients.

More particularly, the human anti-GCGR antibodies of the invention may lower blood glucose to levels ranging from about 80 mg/dL to about 180 mg/dL, or from about 80 mg/dL to about 140 mg/dL, but may do so without the risk of inducing hypoglycemia or wide fluctuations in glucose. In one embodiment, patients experiencing stress hyperglycemia who may benefit from treatment with the antibodies of the invention may be diabetic or non-diabetic patients. In one embodiment, patients experiencing stress hyperglycemia who may benefit from treatment with the antibodies of the invention may be critically ill patients (diabetic or non-diabetic), requiring admission to an intensive care unit for treatment. In one embodiment, patients experiencing stress hyperglycemia who may benefit from treatment with the antibodies of the invention may be non-critically ill patients (diabetic or non-diabetic), who do not require admission to an intensive care unit, but who may have an extended hospital stay (about five days or longer).

Other conditions or disorders treatable by the therapeutic methods of the invention include hyperosmolar hyperglycemia syndrome, hyperinsulinemia, the metabolic syndrome, insulin resistance syndrome, impaired fasting glucose, or hyperglycemia associated with hypercholesterolemia, hypertriglyceridemia, hyperlipidemia, and general dyslipidemias.

The antibodies may also be useful for treating patients with inoperable glucagonoma (pancreatic endocrine tumor with or without necrolytic migratory erythema and hyperglycemia).

In a seventh aspect, the invention provides a method of reducing the amount/dosage of insulin necessary to lower blood glucose levels to within a normal range in a patient at risk for developing stress hyperglycemia, or in a patient suffering from stress hyperglycemia, the method comprising administering an isolated human monoclonal antibody that binds specifically to the glucagon receptor concomitantly with insulin.

In one embodiment, the dosage of insulin may be reduced by about 10% to about 95%, preferably by about 30% to about 95%, more preferably by about 50% to about 90%, more preferably by about 75% to about 90% when administered concomitantly with an isolated human antibody that binds specifically to the glucagon receptor.

In one embodiment, the dosage of insulin may be reduced by about 90% when administered concomitantly with an isolated human monoclonal antibody that binds specifically to the glucagon receptor, wherein the isolated human monoclonal antibody that binds specifically to the glucagon receptor comprises a HCVR/LCVR amino acid sequence pair as set forth in SEQ ID NOs: 86/88.

In one embodiment, the antibody that demonstrates an insulin sparing effect (i.e. the ability to aid in lowering blood glucose when used in conjunction with suboptimal insulin doses, for example, a reduction in insulin dose that ranges from about 30% to 95% of the normal insulin dose needed to lower blood glucose to within a normal range when used as stand alone therapy), comprises the complementarity determining regions (CDRs) of a heavy chain variable region (HCVR), wherein the HCVR has an amino acid sequence selected from the group consisting of SEQ ID NOs: 2, 18, 34, 50, 66, 70, 86, 90, 106, 110, 126, 130 and 146; and the CDRs of a light chain variable region (LCVR), wherein the LCVR has an amino acid sequence selected from the group consisting of SEQ ID NOs: 10, 26, 42, 58, 68, 78, 88, 98, 108, 118, 128, 138 and 148.

In one embodiment, the isolated human monoclonal antibody or antigen-binding fragment thereof that demonstrates an insulin sparing effect comprises a heavy chain variable region (HCVR) having an amino acid sequence selected from the group consisting of SEQ ID NO: 2, 18, 34, 50, 66, 70, 86, 90, 106, 110, 126, 130 and 146.

In one embodiment, the isolated human monoclonal antibody or antigen-binding fragment thereof that demonstrates an insulin sparing effect comprises a light chain variable region (LCVR) having an amino acid sequence selected from the group consisting of SEQ ID NO: 10, 26, 42, 58, 68, 78, 88, 98, 108, 118, 128, 138 and 148.

In one embodiment, the isolated human monoclonal antibody or antigen-binding fragment thereof that demonstrates an insulin sparing effect comprises: (a) a HCVR having an amino acid sequence selected from the group consisting of SEQ ID NO: 2, 18, 34, 50, 66, 70, 86, 90, 106, 110, 126, 130 and 146; and (b) a LCVR having an amino acid sequence selected from the group consisting of SEQ ID NO: 10, 26, 42, 58, 68, 78, 88, 98, 108, 118, 128, 138 and 148.

In one embodiment, the isolated human monoclonal antibody or antigen-binding fragment thereof that demonstrates an insulin sparing effect comprises:
(a) a HCDR1 domain having an amino acid sequence selected from the group consisting of SEQ ID NO: 4, 20, 36, 52, 72, 92, 112 and 132;
(b) a HCDR2 domain having an amino acid sequence selected from the group consisting of SEQ ID NO: 6, 22, 38, 54, 74, 94, 114 and 134;
(c) a HCDR3 domain having an amino acid sequence selected from the group consisting of SEQ ID NOs: 8, 24, 40, 56, 76, 96, 116 and 136;
(d) a LCDR1 domain having an amino acid sequence selected from the group consisting of SEQ ID NO: 12, 28, 44, 60, 80, 100, 120 and 140;
(e) a LCDR2 domain having an amino acid sequence selected from the group consisting of SEQ ID NO: 14, 30, 46, 62, 82, 102, 122 and 142; and
(f) a LCDR3 domain having an amino acid sequence selected from the group consisting of SEQ ID NO: 16, 32, 48, 64, 84, 104, 124 and 144.

In one embodiment, the isolated human monoclonal antibody or antigen-binding fragment comprises a HCVR/LCVR sequence pair selected from the group consisting of SEQ ID NO: 2/10, 18/26, 34/42, 50/58, 66/68, 70/78, 86/88, 90/98, 106/108, 110/118, 126/128, 130/138, and 146/148.

In one embodiment, the isolated human monoclonal antibody comprises a HCVR/LCVR amino acid sequence pair as set forth in SEQ ID NOs: 86/88.

Other embodiments will become apparent from a review of the ensuing detailed description.

DETAILED DESCRIPTION

Figure 1:
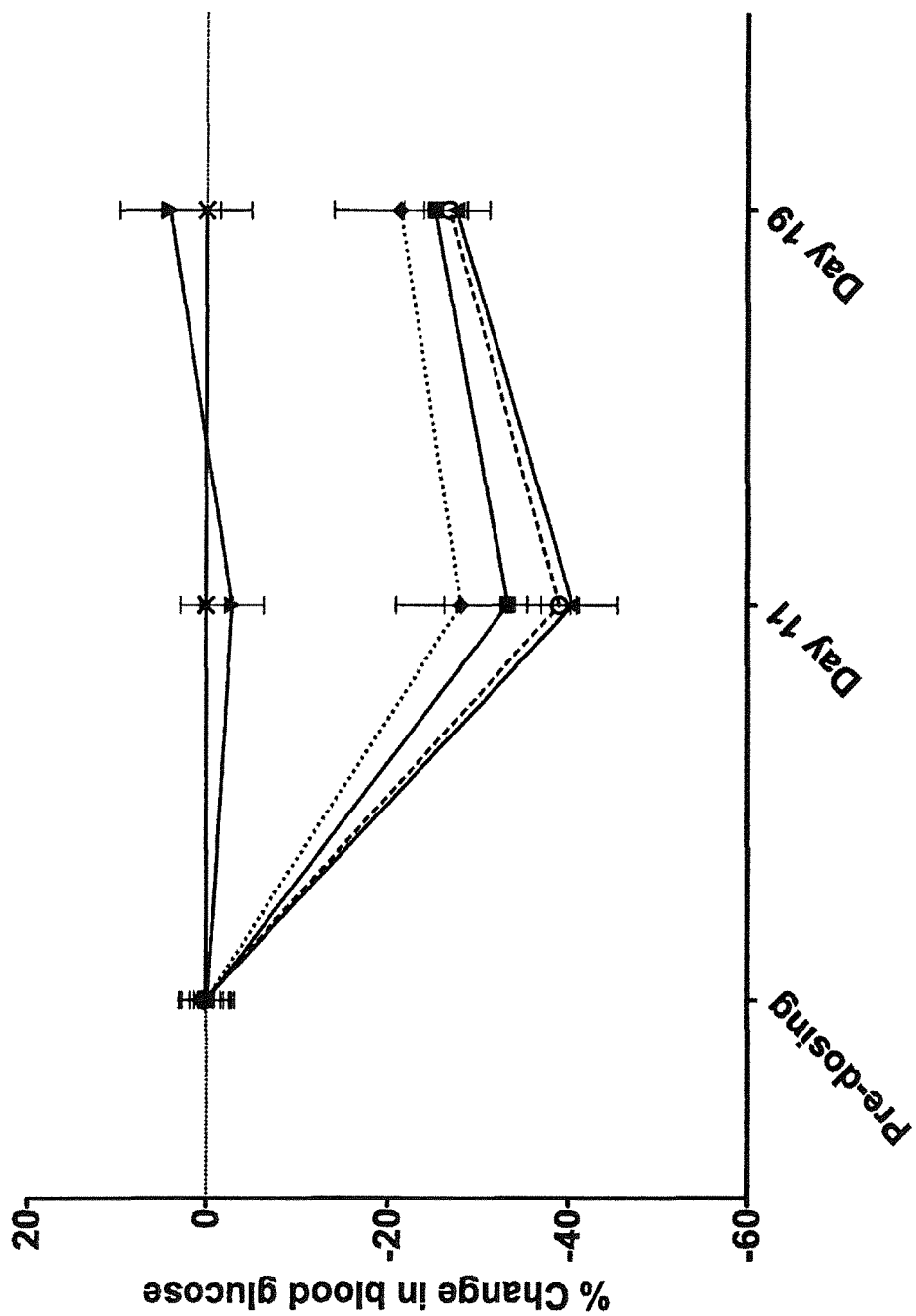
FIG. 1 shows the percent change in blood glucose levels in C57BL6 mice after administration of H4H1327P (anti-GCGR antibody), and/or H1H316P (anti-PCSK9 antibody) when given alone or in combination. Control (X with solid line); H4H1327P at 3 mg/kg (■ with solid line); H4H1327P at 10 mg/kg (▲ with solid line); H1H316P at 10 mg/kg (◉ with solid line); H4H1327P at 3 mg/kg+H1H316P at 10 mg/kg (● with dashed line); H4H1327P at 10 mg/kg+ H1H316P at 10 mg/kg (○ with dashed lines).

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, preferred methods and materials are now described. All publications mentioned herein are incorporated herein by reference in their entirety.

DEFINITIONS

The "glucagon receptor", also referred to herein as "GCGR", belongs to the G protein-coupled receptor class 2 family and consists of a long amino terminal extracellular domain (See SEQ ID NO: 158 for DNA encoding the N-terminal extracellular domain and SEQ ID NO: 159 for the amino acid sequence of the N-terminal extracellular domain), seven transmembrane segments, and an intracellular C-terminal domain (Jelinek et al., Science 259: 1614-1616 (1993), Segre et al., Trends Endocrinol. Metab 4:309-314 (1993)). Glucagon receptors are notably expressed on the surface of hepatocytes where they bind to glucagon and transduce the signal provided thereby into the cell. Accordingly, the term "glucagon receptor" also refers to one or more receptors that interact specifically with glucagon to result in a biological signal. DNA sequences encoding glucagon receptors of rat and human origin have been isolated and disclosed in the art (EP0658200B1). The murine and cynomolgus monkey homologues have also been isolated and sequenced (Burcelin, et al., Gene 164 (1995) 305-310); McNally et al., Peptides 25 (2004) 1171-1178). As used herein, "glucagon receptor" and "GCGR" are used interchangeably. The expression "GCGR", "hGCGR" or fragments thereof, as used herein, refers to the human GCGR protein or fragment thereof, unless specified as being from a non-human species, e.g. "mouse GCGR", "rat GCGR", or "monkey GCGR". Moreover, "GCGR," or "hGCGR", as used herein, refers to human GCGR having the nucleic acid sequence shown in SEQ ID NO: 157 and the amino acid sequence of SEQ ID NO: 153, or a biologically active fragment thereof. There are a variety of sequences related to the GCGR gene having the following Genbank Accession Numbers: NP_000151.1 (human), NP_742089.1 (rat), XP_001111894.1 (rhesus monkey), and NP_032127.2 (mouse). Other sequences disclosed herein include human GCGR (SEQ ID NO: 153), mouse GCGR (SEQ ID NO: 154), Cynomolgus monkey (SEQ ID NO: 155), rat GCGR (SEQ ID NO: 156). In certain embodiments, fusion proteins useful in the invention may include SEQ ID NO: 149 (hGCGR-hFc, residues 27-144 of NP_000151.1 fused to the Fc region of human IgG) SEQ ID NO:150 (hGCGR-hFc, residues 27-144 of NP_000151.1 fused to the Fc region of human IgG), SEQ ID NO:151 (hGCGR-mmH, residues 27-144 of NP_000151.1 fused to a myc-myc-his tag), and SEQ ID NO:152 (MfGCGR-hFc, containing the N-terminal sequence of Mf, cynomolgus monkey, which is identical to residues 27-144 of GCGR of the rhesus monkey, *Macaca mulatta*, having accession number XP_001111894.1, and which is fused to the Fc region of human IgG). The nucleic acid sequences, the polypeptides encoded by them, and other nucleic acid and polypeptide sequences are herein incorporated by reference in their entireties as well as for individual subsequences contained therein.

The term "human proprotein convertase subtilisin/kexin type 9" or "hPCSK9", as used herein, refers to hPCSK9 encoded by the nucleic acid sequence shown in SEQ ID NO:192 and having the amino acid sequence of SEQ ID NO:193, or a biologically active fragment thereof.

The term "antibody", as used herein, is intended to refer to immunoglobulin molecules comprised of four polypeptide chains, two heavy (H) chains and two light (L) chains interconnected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the anti-GCGR antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully-human anti-GCGR antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-hGCGR antibodies comprising variants of any of the HCVR, LCVR, and/or CDR amino acid sequences disclosed herein having one or more conservative substitutions. For example, the present invention includes anti-hGCGR antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The anti-human GCGR antibodies of the invention may be designated as "anti-hGCGR" or "anti-GCGR".

The term "specifically binds," or the like, means that an antibody or antigen-binding fragment thereof forms a complex with an antigen that is relatively stable under physiologic conditions. Specific binding can be characterized by an equilibrium dissociation constant of at least about $1 \times 10^{-6}$ M or less (e.g., a smaller $K_D$ denotes a tighter binding). Methods for determining whether two molecules specifically bind are well known in the art and include, for example, equilibrium dialysis, surface plasmon resonance, and the like. An isolated antibody that specifically binds hGCGR may, however, exhibit cross-reactivity to other antigens such as GCGR molecules from other species. Moreover, multi-specific antibodies that bind to hGCGR and one or more additional antigens or a bi-specific that binds to two different regions of hGCGR are nonetheless considered antibodies that "specifically bind" hGCGR, as used herein.

The term "high affinity" antibody refers to those mAbs having a binding affinity to hGCGR, expressed as $K_D$, of at least $10^{-9}$ M; preferably $10^{-10}$ M; more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antibody that dissociates from hGCGR with a rate constant of $1 \times 10^{-3}$ s$^{-1}$ or less, preferably $1 \times 10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to specifically bind to hGCGR.

The specific embodiments, antibody or antibody fragments of the invention may be conjugated to a therapeutic moiety ("immunoconjugate"), such as a second GCGR antagonist, or to biguanide (metformin), a sulfonylurea (such as glyburide, glipizide), a PPAR gamma agonist (such as pioglitazone, or rosiglitazone), an alpha glucosidase inhibitor (such as acarbose, or voglibose), EXENATIDE® (glucagon-like peptide 1), SYMLIN® (pramlintide), a chemotherapeutic agent, a radioisotope, or any other therapeutic moiety useful for treating a disease or condition caused in part by unwanted glucagon activity.

An "isolated antibody", as used herein, is intended to refer to an antibody that is substantially free of other antibodies (Abs) having different antigenic specificities (e.g., an isolated antibody that specifically binds hGCGR, or a fragment thereof, is substantially free of Abs that specifically bind antigens other than hGCGR).

A "blocking antibody" or a "neutralizing antibody", as used herein (or an "antibody that neutralizes GCGR activity"), is intended to refer to an antibody whose binding to hGCGR results in inhibition of at least one biological activity of GCGR. For example, an antibody of the invention may aid in preventing the increase in blood glucose levels associated with elevation of glucagon levels. Alternatively, an antibody of the invention may demonstrate the ability to block cAMP production in response to glucagon. This inhibition of the biological activity of GCGR can be assessed by measuring one or more indicators of GCGR biological activity by one or more of several standard in vitro or in vivo assays known in the art (see examples below).

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403 410 and (1997) Nucleic Acids Res. 25:3389 402, each of which is herein incorporated by reference.

In specific embodiments, the antibody or antibody fragment for use in the method of the invention may be monospecific, bi-specific, or multi-specific. Multi-specific antibodies may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise an Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 mAbs; N44S, K52N, and V82I (IMGT; N384S, K392N, and V422I by EU) in the case of IgG2 mAbs; and Q15R, N44S, K52N, V57M, R69K, E79Q, and V82I (by IMGT; Q355R, N384S, K392N, V397M, R409K, E419Q, and V422I by EU) in the case of IgG4 mAbs. Variations on the bi-specific antibody format described above are contemplated within the scope of the present invention.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

The term "blood glucose level", or "level of blood glucose" shall mean blood glucose concentration. In certain embodiments, a blood glucose level is a plasma glucose level. Plasma glucose may be determined in accordance with Etgen et al., (Metabolism 2000; 49(5): 684-688) or calculated from a conversion of whole blood glucose concentration in accordance with D'Orazio et al., (Clin. Chem. Lab. Med. 2006; 44(12): 1486-1490).

"Normal glucose levels" refers to mean plasma glucose values in humans of less than about 100 mg/dL for fasting levels, and less than about 145 mg/dL for 2-hour post-prandial levels or 125 mg/dL for a random glucose.

The term "elevated blood glucose level" or "elevated levels of blood glucose" shall mean an elevated blood glucose level such as that found in a subject demonstrating clinically inappropriate basal and postprandial hyperglycemia or such as that found in a subject in oral glucose tolerance test (oGTT), with "elevated levels of blood glucose" being greater than about 100 mg/dL when tested under fasting conditions, and greater than about 200 mg/dL when tested at 1 hour.

"Cholesterol normalization" or "normal cholesterol levels" refers to a total cholesterol level in a human of about less than 200 mg/dL, with a range of about 200-240 mg/dL considered borderline high. From the total normal cholesterol, a mean LDL value in humans of about 100 to about 129 mg/dL is considered normal and an HDL value above 45 mg/dL is considered normal. The normal triglyceride level in humans is less than 150 mg/dL. The normal total/HDL ratio is below 4.5, and the normal LDL/HDL ratio is less than 3. These values may be determined in accordance with standard laboratory practice (see also, Friedewald, W T, Clin. Chem. (1972), 18:499-502; Chen, Y. et al. Lipids Health Dis. (2010); 9:52; Keevil, J G, et al., Circulation (2007), 115:1363-1370; and Bairaktari, E. et al., Clin. Biochem. (2000), 33:549-555). In certain embodiments of the invention, the anti-GCGR antibodies may be useful to lower blood glucose levels to within the normal range. In certain embodiments of the invention, the anti-GCGR antibodies may be useful to increase the level of HDL-C. In certain embodiments of the invention, the anti-GCGR antibodies may be useful to decrease the level of triglycerides.

The term "glucagon receptor antagonist" refers to any molecule, either natural, or synthetic, including proteins, peptides, nucleic acids, antibodies, or small organic molecules. A "glucagon receptor antagonist", as described herein, may inhibit the binding of glucagon to its receptor, thereby preventing at least one biological activity associated with the binding of glucagon to its receptor, e.g. elevation of blood glucose levels. Examples of glucagon receptor antagonists are described in, for example, U.S. Pat. Nos. 7,947,809; 8,158,759; 7,989,472 and 7,494,978, as well as in the following US patent publications: US2008/036341, US2011/0223160, US2009/0041784, US2011/0312911 and in the following WO publications: WO2007/120284, WO2011/037815 and WO2011/119541.

The term "stress hyperglycemia", which is used interchangeably with "stress-induced hyperglycemia", refers to a condition whereby a patient suffers from a transient increase in blood glucose (>140 mg/dL) that is temporally linked to the stress of an acute injury or illness. Stress hyperglycemia can occur in patients with or without a history of diabetes. The cause is thought to be directly related to the stress of the underlying medical illness, anesthesia, surgery, or trauma.

Stress hyperglycemia is the result of, or may be exacerbated by, any one or more of the following risk factors, conditions or therapies: pre-existing type 1 or type 2 diabetes; hypertonic dehydration; infusion of catecholamine pressors; glucocorticoid therapy; obesity; aging; excessive dextrose administration; parenteral nutrition, enteral nutrition, pancreatitis; sepsis; stroke; traumatic head injury; hypothermia; hypoxemia; uremia; cirrhosis; anesthesia; pre-operative or post-operative hospital stays (pen-operative hyperglycemia); admission to an emergency room, a trauma center, or an intensive care unit; prolonged hospital stays; surgical procedures; an infection; or a worsening chronic illness.

The term "critically ill", as used herein, generally refers to a patient suffering from a disease, disorder, injury, surgical procedure, or other condition who requires treatment or monitoring in a critical care unit, or an intensive care unit of a hospital. In its broadest sense, the term a "critically ill" patient, as used herein refers to a patient who has sustained or is at risk of sustaining acutely life-threatening single or multiple organ system failure. A critically ill patient may be a "diabetic patient", e.g. a patient having been diagnosed as having diabetes using standard tests known to those skilled in the art; or a "non-diabetic patient", e.g. a patient who has been diagnosed as not having diabetes using standard methods known to those skilled in the art.

The term "not-critically ill", or "non-critically ill" refers to a hospitalized patient suffering from a disease, disorder, or condition that does not require treatment or monitoring in a critical care unit, or intensive care unit of a hospital. In its broadest sense, the term a "not-critically ill" patient, as used herein refers to a patient other than one who has sustained or is at risk of sustaining acutely life-threatening single or multiple organ system failure due to disease, injury, surgical procedure, or other condition.

The term "Intensive Care Unit" (herein designated ICU), as used herein refers to the part of a hospital where critically ill patients are treated. This might vary from country to country and even from hospital to hospital and this part of the hospital may not necessary, officially, bear the name "Intensive Care Unit" or a translation or derivation thereof. The term "Intensive Care Unit" also covers any health care unit that treats patients with life-threatening conditions requiring constant, close monitoring and support from equipment and medication in order to maintain normal bodily functions.

The term "treating" or "treatment", as used herein, refers to an approach for obtaining beneficial or desired clinical results. For purposes of this invention, beneficial or desired clinical results include, but are not limited to, one or more of the following: improvement in blood glucose to within about 80-180 mg/dL, or to within about 80-140 mg/dL, or an improvement in any one or more conditions, diseases, or symptoms associated with, or resulting from, elevated levels of blood glucose, including, but not limited to susceptibility to infections, organ failure, disability after stroke, polyneuropathy, arrhythmia, or mortality in patients. In addition, "treating" with a glucagon receptor antagonist of the invention may result in a beneficial or desired clinical result which may include an improvement in blood glucose level to within about 80-180 mg/dL, or to within about 80-140 mg/dL, in any condition or disease resulting from exposure to any one or more stress-inducing stimulus or glucose elevating stimulus selected from the group consisting of: pre-existing type 1 or type 2 diabetes; infusion of catecholamine pressors; parenteral nutrition; enteral nutrition; glucocorticoid therapy; obesity; aging; excessive dextrose administration; pancreatitis; sepsis; stroke; traumatic head injury; hypothermia; hypoxemia; uremia; cirrhosis; anesthesia; pre-operative or post-operative hospital stays (pen-operative hyperglycemia); admission to an emergency room, a trauma center, or an intensive care unit; prolonged hospital stays; surgical procedures; an infection; and a chronic illness. "Treating" with a glucagon receptor antagonist of the invention may also lead to prevention of the onset of stress hyperglycemia.

A "stress-inducing stimulus", which is used interchangeably with a "glucose-elevating stimulus", refers to an event that promotes the elevation of blood glucose to above-normal levels. Examples of a "stress-inducing stimulus", or a "glucose-elevating stimulus" include any one or more of the following: pre-existing type 1 or type 2 diabetes; hypertonic dehydration; infusion of catecholamine pressors; parenteral nutrition; enteral nutrition; glucocorticoid therapy; obesity; aging; excessive dextrose administration; pancreatitis; sepsis; stroke; traumatic head injury; hypothermia; hypoxemia; uremia; cirrhosis; anesthesia; pre-operative or post-operative hospital stays (pen-operative hyperglycemia); admission to an emergency room, a trauma center, or an intensive care unit; prolonged hospital stays; surgical procedures; an infection; and a chronic illness.

The term "insulin", as used herein refers to insulin from any species such as human insulin, porcine insulin, bovine insulin and salts thereof, such as zinc salts.

Glucagon-like peptide-1 (GLP-1) is an incretin hormone derived from the posttranslational modification of proglucagon and secreted by gut endocrine cells. GLP-1 mediates its actions through a specific G protein-coupled receptor (GPCR), namely GLP-1R. GLP-1 is best characterized as a hormone that regulates glucose homeostasis. GLP-1 has been shown to stimulate glucose-dependent insulin secretion and to increase pancreatic beta cell mass. GLP-1 has also been shown to reduce the rate of gastric emptying and to promote satiety. The efficacy of GLP-1 peptide agonists in controlling blood glucose in Type 2 diabetics has been demonstrated in several clinical studies [see, e.g., Nauck et al., Drug News Perspect (2003) 16:413-422], as has its efficacy in reducing body mass [Zander et al., Lancet (2002) 359:824-830].

The term "GLP-1 compound", as used herein refers to GLP-1 (1-37), exendin-4 (1-39), insulinotropic (insulin stimulating) fragments thereof, insulinotropic analogs thereof and insulinotropic derivatives thereof. Insulinotropic fragments of GLP-1 (1-37) are insulinotropic peptides for which the entire sequence can be found in the sequence of GLP-1 (1-37) and where at least one terminal amino acid has been deleted. Examples of insulinotropic fragments of GLP-1 (1-37) are GLP-1 (7-37) wherein the amino acid residues in positions 1-6 of GLP-1 (1-37) have been deleted, and GLP-1 (7-36) where the amino acid residues in position 1-6 and 37 of GLP-1 (1-37) have been deleted. Insulinotropic derivatives of GLP-1 (1-37) and analogs thereof are what the person skilled in the art may consider to be derivatives of these peptides, i.e. having at least one substituent which is not present in the parent peptide molecule with the proviso that said derivative either is insulinotropic or is a prodrug of an insulinotropic compound. Examples of substituents are amides, carbohydrates, alkyl groups and lipophilic substituents. Further examples of GLP-1 (1-37) insulinotropic fragments thereof, insulinotropic analogs thereof and insulinotropic derivatives thereof are described in WO 98/08871, WO 99/43706, U.S. Pat. No. 5,424,286 and WO 00/09666.

The term "GLP-1 agonist", as used herein refers to a molecule, preferably GLP-1 or an analogue or a derivative thereof, or exendin or an analogue or a derivative thereof, or a non-peptidyl compound, which interacts with the GLP-1 receptor and induces the physiological and pharmacological characteristics of the GLP-1 receptor. Methods for identifying GLP-1 agonists are described in WO 93/19175. The term "GLP-1 agonist" is also intended to comprise active metabolites and prodrugs thereof, such as active metabolites and prodrugs of GLP-1 or an analogue or a derivative thereof, or exendin or an analogue or a derivative thereof, or a non-peptidyl compound. A "metabolite" is an active derivative of a GLP-1 agonist produced when the GLP-1 agonist is metabolized. A "prodrug" is a compound which is either metabolized to a GLP-1 agonist or is metabolized to the same metabolite(s) as a GLP-1 agonist.

The term "GLP-1 secretagogue" shall mean an agent (e.g., a compound) that promotes GLP-1 secretion from a cell, e.g. an enteroendocrine cell.

The term "dipeptidyl-peptidase IV inhibitor" or "DPP-IV inhibitor," as used herein, refers to a compound that binds to DPP-IV and inhibits DPP-IV dipeptidyl peptidase activity. Dipeptidyl peptidase IV exhibits catalytic activity against a broad range of peptide substrates that includes peptide hormones, neuropeptides, and chemokines. The incretins glucagon-like peptide 1 (GLP-1) and glucose-dependent insulinotropic polypeptide (GIP), which stimulate glucose-dependent insulin secretion and otherwise promote blood glucose homeostasis, are rapidly cleaved by DPP-IV at the position 2 alanine leading to inactivation of their biological activity. Both pharmacological and genetic attenuation of DPP-IV activity is associated with enhanced incretin action, increased insulin, and lower blood glucose in vivo. A second-generation DPP-IV inhibitor, LAF237 (Ahren et al., J Clin Endocrinol Metab (2004) 89:2078-2084; and Villhauer et al., J Med Chem (2003) 46:2774-2789), is currently in phase 3 clinical trials for Type 2 diabetes and additional DPP-IV inhibitors are in various stages of clinical development, including MK-0431 (sitagliptin), BMS-477118 (saxagliptin), Onglyza, Linagliptin, PSN-9301, SYR-322 and SYR-619, Vildagliptin, Alogliptin, R1438, TA-6666, PHX1149, GRC 8200, TS-021, SSR 162369, and ALS 2-0426.

General Description

The therapeutic value of glycemic control is well documented. However, a substantial unmet need remains for agents that provide appropriate glycemic control with a low risk of hypoglycemia and a favorable side effect profile in both chronic and acute settings. The present invention is directed to such agents. More particularly, the present invention relates to the use of glucagon receptor antagonists, more particularly, antibodies specific for the human glucagon receptor (GCGR), which induce rapid, potent and sustained glucose and ketone lowering in preclinical models of hyperglycemia without evidence of hypoglycemia. Furthermore, in obese mouse models, the antibodies of the invention provide for robust weight loss and body fat loss. Moreover, in an animal model of stress hyperglycemia, the antibodies of the present invention demonstrate a significant effect on lowering blood glucose levels to within a normal range.

Since glucagon exerts its physiological effects by signaling through the glucagon receptor, the glucagon receptor may be a potential therapeutic target for diabetes and other glucagon related metabolic disorders. The use of glucagon receptor antagonists, such as the antibodies described herein, may be an effective means of achieving normal levels of glucose, thereby ameliorating, or preventing one or more symptoms or long term complications associated with diabetes. The antibodies of the present invention may also be useful for ameliorating conditions associated with, for example, impaired glucose tolerance, for treating obesity, for preventing weight gain, for treating metabolic syndrome, for treating hyperglycemia, or for treating diabetic conditions, including diabetic ketoacidosis, or for preventing and/or lowering the risk of developing any one or more of the complications associated with diabetes, such as nephropathy, neuropathy, retinopathy, cataracts, stroke, atherosclerosis, impaired wound healing and other complications associated with diabetes, known to those skilled in the art.

The use of the anti-hGCGR antibodies, as described herein, may also be useful for treating other conditions, including stress hyperglycemia (also known as stress-induced hyperglycemia, discussed in more detail below), hyperglycemic hyperosmolar syndrome (Stoner, G. D., American Family Physician, (2005), 71(9):1723-1730; Diabetes Spectrum, Umpierrez, G. E., (2002), 15(1):28-36; Nugent, B. W., Emergency Medicine Clinics of North America, (2005), 23:629-648), perioperative hyperglycemia (Frisch, A. et al. Diabetes Care, (2010), 33(8):1783-1788; Hanazaki, K. et al. World J Gastroenterol, (2009), 15(33): 4122-4125; Smiley, D. D. et al. Southern Medical Journal, (2006), 99(6):580-589; Hermanides, J. et al., The Netherlands J. of Med. 67(6):226-229; Maerz, L. L. et al., Current Opinion in Critical Care, (2011), 17:370-375), hyperglycemia in intensive care unit patients (Gunst, J. et al., Seminars in Dialysis, (2010), 23(2):157-162; Losser, M-R., Critical care, (2010), 14:231), hyperinsulinemia, and insulin resistance syndrome and glucagonoma (pancreatic endocrine tumor with or without necrolytic migratory erythema and hyperglycemia) (See for example, Boden, G. et al., N Engl J Med (1986); 314:1686-1689).

In certain embodiments, the antibodies of the invention were obtained from mice immunized with a primary immunogen, followed by immunization with a secondary immunogen. The immunogen may be a cell line expressing the GCGR protein, or a biologically active fragment thereof, or DNA encoding the GCGR protein or active fragment thereof, or the GCGR protein or active fragment thereof. For example, in certain embodiments, the primary immunogen may be a cell line engineered using standard procedures known in the art to over-express full-length hGCGR (e.g. the mouse MG87 cell line). Alternatively, DNA immunization may be performed using DNA encoding full-length hGCGR (e.g. hGCGR constructs derived from accession number NP_000151.1), or DNA encoding a biologically active fragment thereof, for example, DNA encoding the N-terminal domain of GCGR (see, for example, SEQ ID NO: 158, which encodes SEQ ID NO: 159), or a soluble N-terminal protein, including that of SEQ ID NO: 159, or the amino acids spanning residues 27-144 of SEQ ID NO: 153. The secondary immunogen may be a GCGR protein, or biologically active fragment thereof, or a fusion protein, such as hGCGR-mmH (REGN547, SEQ ID NO: 151) or hGCGR-hFc (REGN315, SEQ ID NO: 150; REGN316, SEQ ID NO: 149).

In certain embodiments of the present invention, the N-terminal domain, having the amino acid sequence shown in SEQ ID NO: 159 (without the signal sequence), or any one or more of the ectodomains of GCGR, e.g. any one or more of the extracellular regions (or fragments thereof) may be used to prepare antibodies that bind GCGR and inhibit its function, e.g. its ability to bind glucagon, which would result in lowering of blood glucose levels.

The full-length amino acid sequence of human GCGR is shown as SEQ ID NO: 153. The signal peptide spans amino acid residues 1-26 of SEQ ID NO: 153; the N-terminal domain spans residues 27-144 of SEQ ID NO: 153; extracellular region 1 (EC1) spans amino acid residues 194-226 of SEQ ID NO: 153; extracellular region 2 (EC2) spans amino acid residues 285-305 of SEQ ID NO: 153; and extracellular region 3 (EC3) spans amino acid residues 369-384 of SEQ ID NO:153.

In certain embodiments, antibodies that bind specifically to GCGR may be prepared using fragments of the above-noted extracellular regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of GCGR specific antibodies. In certain embodiments, any one or more of the above-noted regions of GCGR, or fragments thereof may be used for preparing monospecific, bispecific, or multispecific antibodies.

Stress Hyperglycemia

Stress hyperglycemia is defined as a transient increase in blood glucose (>140 mg/dL) that is temporally linked to the stress of an acute injury or illness. This common medical condition occurs frequently in the diabetic and non-diabetic hospitalized patient and requires prompt therapeutic intervention (Kitabchi A E, Umpierrez G E, Miles J M, Fisher J N, Diabetes Care, (2009), July; 32(7):1335-43; Baker E H, Janaway C H, Philips B J, Brennan A L, Baines D L, Wood D M, et al., Thorax, (2006), April; 61(4):284-9). Serious medical and surgical conditions associated with stress hyperglycemia include myocardial infarction, burns, and cardiopulmonary bypass surgery (Rocha D M, Santeusanio F, Faloona G R, Unger R H, N Engl J. Med. (1973), April 5; 288(14):700-3). Stress hyperglycemia also occurs in non-critically ill patients, for example, in those admitted for exacerbation of chronic obstructive pulmonary disease (Oshima C, Kaneko T, Tsuruta R, Oda Y, Miyauchi T, Fujita M, et al., Resuscitation, (2010), February; 81(2):187-92). In hospitalized patients, stress hyperglycemia is associated with substantial increases in infections, dialysis, blood transfusions, polyneuropathy, and other medical complications including death (up to 18-fold).

Stress Hyperglycemia has increasingly been the focus of clinical investigations that demonstrate reductions in the aforementioned medical complications with intensive insulin therapy. However, intensive insulin therapy is associated with a substantial risk of hypoglycemia, which greatly reduces the medical benefits of therapy. As a result, current practice guidelines have been revised to target higher blood glucose levels in order to lower the risk of hypoglycemia. This may limit the benefit of therapy (Kitabchi A E, Umpierrez G E, Miles J M, Fisher J N, Diabetes Care, (2009), July; 32(7): 1335-43; Baker E H, Janaway C H, Philips B J, Brennan A L, Baines D L, Wood D M, et al., Thorax, (2006), April; 61(4): 284-9).

Studies in patients admitted for conditions associated with stress hyperglycemia have demonstrated sustained glucagon elevations up to 10-fold above the normal levels (Rocha D M, Santeusanio F, Faloona G R, Unger R H, N Engl J. Med. (1973), April 5; 288(14):700-3; Oshima C, Kaneko T, Tsuruta R, Oda Y, Miyauchi T, Fujita M, et al, Resuscitation, (2010), February; 81(2):187-92). In these settings, elevated glucagon may contribute to elevated blood glucose levels and may hamper achieving target glycemic control. Therefore, adding a glucagon receptor antagonist, such as any one of the antibodies described herein, to the current therapeutic regimen for stress hyperglycemia may reduce the risk of hypoglycemic episodes, allow patients to be treated to more physiologic blood glucose levels, and reduce morbidity and mortality. The present invention describes the use of antibodies specific for the glucagon receptor for the short-term treatment of metabolic perturbations in patients with stress hyperglycemia.

Stress hyperglycemia is a common observation in many serious medical conditions such as myocardial infarction, burns, and cardiopulmonary bypass surgery (Kitabchi A E, Umpierrez G E, Miles J M, Fisher J N, Diabetes Care, (2009), July; 32(7):1335-43). The prevalence of stress hyperglycemia has been estimated to occur in 32-38% of hospitalized patients; 41% of the critically ill; 44% with heart failure; and 80% post-cardiac surgery. Further, 33% of non-ICU patients with stress hyperglycemia and 80% of ICU patients with stress hyperglycemia have no history of DM before hospital admission (Umpierrez G E, Isaacs S D, Bazargan N, You X, Thaler L M, Kitabchi A E, J Clin Endocrinol Metab, (2002), March 87(3):978-82). In a single center study, it was determined that a large majority of patients (75%) seen in the cardiac emergency unit with acute myocardial infarction had blood glucose levels ≥180 mg/dL (Lerario A C, Coretti F M, Oliveira S F, Betti R T, Bastos Mdo S, Ferri Lde A, et al., Arq Bras Endocrinol Metabol. (2008), April; 52(3):465-72). This association of hyperglycemia in acutely ill patients has been recognized for some time. In fact, hyperglycemia was included in the predictive APACHE III severity of illness scoring system in 1991 (Knaus W A, Wagner D P, Draper E A, Zimmerman J E, Bergner M, Bastos P G, et al. Chest, (1991) December; 100(6):1619-36). Hermanides et al. noted that immediately after induction of anesthesia, plasma glucose levels started to increase until the second day post-operatively and did not return to baseline until seven weeks (Hermanides, J. et al. Netherlands J. Med. (2009), Vol. 67(6):226-229).

Any of the fully human monoclonal antibodies described herein as glucagon receptor antagonists may be used for preventing the onset of stress hyperglycemia by administering the antibody prior to an event that is stress-inducing, for example, prior to surgery. The antibodies described herein may also be administered therapeutically for treating stress hyperglycemia, more particularly, for the treatment of metabolic perturbations in patients who are diagnosed with stress hyperglycemia during hospitalization. Accordingly, both prophylactic and therapeutic administration of the anti-GCGR antibodies of the invention is envisioned. One of the fully human monoclonal antibodies will be developed for use in critically ill intensive care unit patients who are at high risk for death. In addition, one of the fully human monoclonal antibodies will be developed for use in non-critically ill patients who are at a low risk for death, but who will benefit from improved metabolic control and thus experience lower morbidity. Currently, there are no therapies specifically approved to prevent the onset of, or to treat stress hyperglycemia. Stress hyperglycemia in patients who are critically ill represents a serious unmet medical need because: 1) these patients have a high risk for imminent death, 2) existing therapies, i.e., intensive insulin may paradoxically increase the risk for death by causing severe hypoglycemia, and 3) the etiology of stress hyperglycemia is multifactorial, and insulin therapy alone may be insufficient for optimal control. Therefore, to address this unmet medical need, the antibodies of the present invention will be tested further in patients either suffering from stress hyperglycemia, or at risk for developing stress hyperglycemia (but prior to the onset of stress hyperglycemia). Recognized surrogates for mortality, such as improved glycemic control and improvement in the Acute Physiology and Chronic Health Evaluation (APACHE) score (Knaus W A, et al., "APACHE II: A Severity of Disease Classification System", Critical Care Medicine, (1985), vol. 13, No. 10, pp. 818-829), will be used in the studies proposed herein.

Mortality in Stress Hyperglycemia

In ICU and non-ICU patients, elevated blood glucose levels are associated with increased morbidity and mortality (Umpierrez G E, Isaacs S D, Bazargan N, You X, Thaler L M, Kitabchi A E, J Clin Endocrinol Metab. (2002), March 87(3): 978-82; McAlister F A, Majumdar S R, Blitz S, Rowe B H, Romney J, Marrie T J, Diabetes Care. (2005), April 28(4): 810-5). There are a number of mechanisms by which hyperglycemia may adversely affect the outcome of the critically ill and non-critically ill patient. In particular, hyperglycemia impairs white blood cell function resulting in abnormal granulocyte adhesion, phagocytosis, respiratory burst and superoxide formation, and intracellular killing (Rubinstein R, Genaro A M, Motta A, Cremaschi G, Wald M R, Clin Exp Immunol. (2008) November 154:235-46; Stegenga M E, van der Crabben S N, Dessing M C, Pater J M, van den Pangaart P S, de Vos A F, et al., Diabet Med. (2008), February; 25(2): 157-64). The risk of developing multiple organ failure increases and survival decreases if infection occurs (McMahon M M, Bistrian BR. Infect Dis Clin North Am. (1995) March 9(1):1-9; Capuano F, Roscitano A, Simon C, Sclafani G, Benedetto U, Comito C, et al. Heart Int. (2006), 2(1):49). In addition, ICU patients develop insulin resistance, in part due to an increase in glucagon. The hepatic insulin resistance leads to an increase in serum concentrations of IGF-1 binding protein. IGF-1 binding protein has been linked to an increase risk of hospital death, possibly reflecting negative effects on IGF-1 and unwanted effects on muscle wasting in the critically ill patient (Van den Berghe G, Baxter R C, Weekers F, Wouters P, Bowers C Y, Veldhuis J D, J Clin Endocrinol Metab, (2000), January 85(1): 183-92; Van den Berghe G, Wouters P, Weekers F, Mohan S, Baxter R C, Veldhuis J D, et al., J Clin Endocrinol Metab. (1999), April; 84(4): 1311-23). Control of blood glucose has also been linked to a decrease in the risk of critical illness polyneuropathy, either directly or through decreased infection and sepsis (Van den Berghe G, Wouters P, Weekers F, Verwaest C, Bruyninckx F, Schetz M, et al. N Engl J. Med. (2001), November 8; 345(19): 1359-67).

Under stress conditions, endogenous glucagon secretion is thought to be elevated by hypovolemia, hypoglycemia and low insulin levels (Young A, Adv Pharmacol. (2005), 52:151-71). Several studies in patients admitted to the hospital for acute myocardial infarction, coronary artery bypass grafts, valve replacement, burns, or sepsis demonstrated glucagon levels elevated 2-10-fold above normal throughout the acute medical illness (Ellger B, Debaveye Y, Vanhorebeek I, Langouche L, Giulietti A, Van Etten E, et al. Diabetes. (2006), April; 55(4): 1096-105; Nygren J, Sammann M, Malm M, Efendic S, Hall K, Brismar K, et al. Clin Endocrinol (Oxf). (1995), October; 43(4): 491-500; Ascione R, Rogers C A, Rajakaruna C, Angelini G D, Circulation. (2008), July 8; 118(2): 113-23; Jakob S M, Stanga Z. Nutrition. (2010), April; 26(4): 349-53. Therefore, it would prove beneficial to prevent the onset of stress hyperglycemia by administering at least one antibody of the invention prophylactically to patients at risk for developing stress hyperglycemia. Alternatively, if the patient exhibits hyperglycemia due to exposure to a stressor, it would be beneficial to administer the antibody therapeutically after the elevation of glucose resulting from exposure to the stressor. The antibody may be administered as stand-alone therapy, or may be administered as adjunct therapy with another glucose lowering agent, for example, insulin.

Current Treatment of Stress Hyperglycemia

Treatment of stress hyperglycemia, currently limited primarily to the administration of insulin, results in improved outcome. This concept is supported by a series of randomized controlled trials that examined the effect of intensive insulin treatment in hospitalized patients and demonstrated improved short-term outcome (reviewed in Krinsley J S, Meyfroidt G, van den Berghe G, Egi M, Bellomo R. Curr Opin Clin Nutr Metab Care. (2012), March; 15(2): 151-60). In 2012, practice guidelines for treatment of stress hyperglycemia in critically ill and non-critically ill patients were established and involved a consensus process including: The Endocrine Society members, American Diabetes Association, American Heart Association, American Association of Diabetes Educators, European Society of Endocrinology, and the Society of Hospital Medicine (Korytkowski M, McDonnell M E, Umpierrez G E, Zonszein J, J Clin Endocrinol Metab. (2012), January; 97(1): 27A-8A; Umpierrez G E, Hellman R, Korytkowski M T, Kosiborod M, Maynard G A, Montori V M, et al. J Clin Endocrinol Metab. (2012) January; 97(1): 16-38).

However, while insulin therapy appears to be the only acceptable treatment for stress hyperglycemia, intensive insulin treatment to target optimal blood glucose levels may result in hypoglycemia, thus reversing the beneficial effects of insulin therapy. Such insulin therapy may actually increase the risk of mortality in this patient population. Thus, a medical need exists for new parenteral agents, such as a monoclonal antibody that blocks glucagon action, to improve the treatment and outcome of patients with stress hyperglycemia.

Accordingly, it is an object of the present invention to treat stress hyperglycemia with an anti-GCGR antibody of the invention, either alone, or in conjunction with at least one other glucose lowering agent. It is an object of the invention to use an anti-GCGR antibody in combination with insulin or potentially as monotherapy to treat stress hyperglycemia in both the critically ill and not critically ill hospitalized patient. It is an object of the invention to provide beneficial effects in this patient population through use of an anti-GCGR antibody of the invention. Such beneficial effects include the following: reduced glucagon-dependent metabolic perturbations such as hyperglycemia and increased catabolism; reduced risk of hypoglycemia; decreased morbidity and mortality (e.g., organ failure and infection); and/or decreased hospital resource utilization (length of stay, nursing care, time in ICU).

It is also an object of the invention to prevent the onset of hyperglycemia in a patient at risk for developing stress hyperglycemia by prophylactic administration of an antibody of the invention, either as stand alone therapy, or in conjunction with at least one other glucose lowering agent, for example, insulin. A patient "at risk for developing stress hyperglycemia" is defined herein as an individual who has been exposed to, or is currently being exposed to, or may be exposed to, certain stressors that may result in a rise in blood glucose levels above normal. These stressors may include, but are not limited to, anesthesia, surgery, trauma, an underlying medical illness, or any other other risk factor selected from the group consisting of type 1 or type 2 diabetes; infusion of catecholamine pressors; glucocorticoid therapy; obesity; aging; excessive dextrose administration; parenteral nutrition, enteral nutrition, pancreatitis; sepsis; stroke; traumatic head injury; hypothermia; hypoxemia; uremia; cirrhosis; anesthesia; pre-operative or post-operative hospital stays (peri-operative hyperglycemia); admission to an emergency room, a trauma center, or an intensive care unit; prolonged hospital stays; an infection; or a worsening chronic illness.

The administration of insulin has in certain instances been associated with a sudden drop in blood glucose (hypoglycemia) and puts the patient at risk for greater morbidity and mortality. Certain studies reported on herein have demonstrated an insulin sparing effect through use of certain antibodies of the invention in conjunction with insulin. Accordingly, based on these studies, it is a further object of the invention to be able to lower the amount of insulin administered to patients if the anti-GCGR antibodies of the invention are administered concurrently with insulin. Such concomitant administration of both the anti-GCGR antibody plus lower amounts of insulin can result in the desired effect without the risk of increased morbidity and/or mortality.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to specifically bind to hGCGR. An antibody fragment may include a Fab fragment, a F(ab')$_2$ fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$—$V_L$ or $V_L$—$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$—$C_H1$; (ii) $V_H$—$C_H2$; (iii) $V_H$—$C_H3$; (iv) $V_H$—$C_H1$-$C_H2$; (v) $V_H$—$C_H1$-$C_H2$-$C_H3$; (vi) $V_H$—$C_H2$-$C_H3$; (vii) $V_H$—$C_L$; (viii) $V_L$—$C_H1$; (ix) $V_L$—$C_H2$; (x) $V_L$—$C_H3$; (xi) $V_L$—$C_H1$-$C_H2$; (xii) $V_L$—$C_H1$-$C_H2$-$C_H3$; (xiii) $V_L$—$C_H2$-$C_H3$; and (xiv) $V_L$—$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to human GCGR.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to GCGR are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies of the instant invention possess very high affinities, typically possessing $K_D$ of from about $10^{-12}$ through about $10^{-9}$ M, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Bioequivalents

The anti-GCGR antibodies and antibody fragments of the present invention encompass proteins having amino acid sequences that vary from those of the described antibodies, but that retain the ability to bind human GCGR. Such variant antibodies and antibody fragments comprise one or more additions, deletions, or substitutions of amino acids when compared to parent sequence, but exhibit biological activity that is essentially equivalent to that of the described antibodies. Likewise, the anti-GCGR antibody-encoding DNA sequences of the present invention encompass sequences that comprise one or more additions, deletions, or substitutions of nucleotides when compared to the disclosed sequence, but that encode an anti-GCGR antibody or antibody fragment that is essentially bioequivalent to an anti-GCGR antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-GCGR antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-GCGR antibody variants comprising amino acid changes, which modify the glycosylation characteristics of the antibodies, e.g., mutations which eliminate or remove glycosylation.

Biological Characteristics of the Antibodies

In general, the antibodies of the present invention may function by binding to at least one of the extracellular regions of hGCGR. In certain embodiments, the antibodies of the present invention may bind to an epitope located in at least the N-terminal region, or to an epitope located in at least one of the extracellular (EC) loops of hGCGR.

In certain embodiments, the antibodies of the present invention may function by blocking or inhibiting GCGR activity by binding to the extracellular N-terminal region, the amino acid sequence of which is shown in SEQ ID NO: 159, and which is encoded by the nucleic acid sequence shown in SEQ ID NO: 158.

In certain embodiments, the antibodies of the present invention may function by blocking or inhibiting GCGR activity by binding to at least one of the EC loops or loop segments within the whole receptor. In one embodiment, the antibodies of the invention may bind to an epitope located in EC1, which is located between about amino acid residue194 to about amino acid residue 226 of SEQ ID NO: 153. Alternatively, or additionally, the antibodies of the invention may bind to an epitope found in EC2, which is located between about amino acid residue 285 to about amino acid residue 302 of SEQ ID NO: 153. Alternatively, or additionally, the antibodies of the invention may bind to an epitope found in EC3, which is located between about amino acid residue 369 to about amino acid residue 384 of SEQ ID NO: 153.

In certain embodiments, the antibodies of the present invention may be bi-specific antibodies. The bi-specific antibodies of the invention may bind one epitope in EC1 and may also bind one epitope in a region of hGCGR other than EC1. In certain embodiments, the bi-specific antibodies of the invention may bind one epitope in EC1 and may also bind one epitope in EC2 or EC3, or in the N-terminal region, or in any other region within EC1, EC2, or EC3 of hGCGR, or any combination thereof. In certain embodiments, the bi-specific antibodies of the invention may bind to two different sites within the same extracellular region.

More specifically, the anti-GCGR antibodies of the invention may exhibit one or more of the following characteristics: (1) ability to bind to a human GCGR or a fragment thereof and to a non-human (e.g., mouse, monkey, rat, rabbit, dog, pig, etc.) GCGR or fragment thereof; (2) ability to bind to a human GCGR or fragment thereof, but not to a non-human (e.g., mouse, monkey, rat, rabbit, dog, pig, etc.) GCGR or fragment thereof; (3) ability to bind to a human GCGR or fragment thereof and to a non-human primate (e.g. monkey) GCGR or fragment thereof, but not to a mouse, rat, rabbit, dog or pig GCGR or GCGR fragment; (4) ability to bind to a human GCGR or fragment thereof and to a non-human primate (e.g. monkey) GCGR or a fragment thereof, and to a mouse GCGR or a fragment thereof, but not to a rat GCGR; (5) ability to bind to a human GCGR or fragment thereof and to a non-human primate (e.g. monkey) GCGR or a fragment thereof, and to a rat GCGR or a fragment thereof, but not to a mouse GCGR; 6) blocks glucagon binding to GCGR; 7) blocks glucagon induced cAMP production; 8) demonstrates the ability to lower blood glucose levels in humans suffering from diabetes and in animal models of diabetes; 9) may or may not lower triglyceride levels to the levels observed in normal mammals; or 10) does not adversely affect plasma lipid levels.

Certain anti-GCGR antibodies of the present invention are able to inhibit or attenuate GCGR activity in an in vitro or in vivo assay. The ability of the antibodies of the invention to bind to and inhibit binding of glucagon to GCGR may be measured using any standard method known to those skilled in the art, including binding assays, reporter bioassays, such as a luciferase reporter assay.

Non-limiting, exemplary in vitro assays for measuring GCGR activity are illustrated in Examples 4 and 5, herein. In Example 4, the binding affinities and kinetic constants of human anti-hGCGR antibodies were determined by surface plasmon resonance and the measurements were conducted on a T100 Biacore instrument. In Example 5, a bioassay was developed in HEK293 cell lines expressing full length human, monkey and mouse GCGR along with a luciferase reporter in order to detect activation through Gαs, and subsequent elevation of cAMP levels and transcriptional activation. Examples 6, 7, 8, 9 and 10 demonstrate the in vivo effects of the antibodies on lowering of blood glucose levels, blood ketone levels, and on weight loss, in various animal models.

The present invention also includes anti-GCGR antibodies and antigen binding fragments thereof which bind to at least one biologically active fragment of any of the following proteins, or peptides: SEQ ID NO: 153 (full length hGCGR), residue numbers 27-144 of SEQ ID NO: 153 (N-terminal domain of hGCGR); residues 194-226 of SEQ ID NO: 153; residues 285-305 of SEQ ID NO: 153; residues 369-384 of SEQ ID NO: 153. Any of the GCGR peptides described herein, or fragments thereof, may be used to generate anti-GCGR antibodies.

The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization. The antibodies specific for GCGR may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

In one embodiment, the invention provides a fully human monoclonal antibody or antigen-binding fragment thereof that specifically binds hGCGR and neutralizes hGCGR activity, wherein the antibody or fragment thereof exhibits one or more of the following characteristics: (i) comprises a HCVR having an amino acid sequence selected from the group consisting of SEQ ID NO: 2, 18, 34, 50, 66, 70, 86, 90, 106, 110, 126, 130, and 146; (ii) comprises a LCVR having an amino acid sequence selected from the group consisting of SEQ ID NO: 10, 26, 42, 58, 68, 78, 88, 98, 108, 118, 128, 138, and 148; (iii) comprises any one or more of the heavy chain CDR1 sequences selected from the group consisting of 4, 20, 36, 52, 72, 92, 112 and 132; any one or more of the heavy chain CDR2 sequences selected from the group consisting of 6, 22, 38, 54, 74, 94, 114 and 134; any one or more of the heavy chain CDR3 sequences selected from the group consisting of 8, 24, 40, 56, 76, 96, 116 and 136; any one or more of the light chain CDR1 sequences selected from the group consisting of 12, 28, 44, 60, 80, 100, 120 and 140; any one or more of the light chain CDR2 sequences selected from the group consisting of 14, 30, 46, 62, 82, 102, 122 and 142; any one or more of the light chain CDR3 sequences selected from the group consisting of 16, 32, 48, 64, 84, 104, 124 and 144; and combinations thereof; (iv) demonstrates binding specificity for any one or more of the following: the N-terminal region of GCGR comprising amino acid residues 27-144 of SEQ ID NO: 153, or for any one or more of the extracellular loops of GCGR, including, for example, EC1, EC2, or EC3, wherein EC1 comprises amino acid residues ranging from about residue 194 to about residue 226 of SEQ ID NO: 153, and wherein EC2 comprises amino acid residues ranging from about residue 285 to about residue 305 of SEQ ID NO: 153; and wherein EC3 comprises amino acid residues ranging from about residue 369 to about residue 384 of SEQ ID NO: 153; (v) binds any one or more of human, monkey, mouse or rat GCGR; (vi) blocks binding of glucagon to GCGR; vi) blocks glucagon induced cAMP production; vii) demonstrates the ability to lower blood glucose levels or blood ketone levels in humans suffering from diabetes or in animal models of diabetes; viii) may or may not lower triglyceride levels to the levels observed in normal mammals; or ix) does not adversely affect plasma lipid levels.

Epitope Mapping and Related Technologies

The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen. An epitope typically includes at least 3, and more usually, at least 5 or 8-10 amino acids in a unique spatial conformation.

Various techniques known to persons of ordinary skill in the art can be used to determine whether an antibody "interacts with one or more amino acids" within a polypeptide or protein, or binds to a particular epitope within a polypeptide or protein. Exemplary techniques include, for example, routine cross-blocking assays, such as that described in *Antibodies*, Harlow and Lane (Cold Spring Harbor Press, Cold Spring Harb., NY). Other methods include alanine scanning mutational analysis, peptide blot analysis (Reineke (2004) Methods Mol Biol 248:443-63), peptide cleavage analysis crystallographic studies and NMR analysis. In addition, methods such as epitope excision, epitope extraction and chemical modification of antigens can be employed (Tomer (2000) Protein Science 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267(2):252-259; Engen and Smith (2001) Anal. Chem. 73:256 A-265A. X-ray crystallography of the antigen/antibody complex may also be used for epitope mapping purposes.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the anti-GCGR antibodies of the invention into groups of antibodies binding different epitopes.

In certain embodiments, the anti-GCGR antibody or antigen-binding fragment of an antibody binds an epitope within at least one of the extracellular regions of GCGR, or to a fragment thereof, wherein the extracellular region is the N-terminal domain, or one of the EC loops, including EC1, EC2, or EC3, as described previously.

In one embodiment, the antibody binds an epitope within the N-terminal region of GCGR, or a fragment thereof, comprising an amino acid sequence ranging from about amino acid residue 27-144 of SEQ ID NO: 153. In one embodiment, the antibody binds an epitope within EC1, or a fragment thereof, comprising an amino acid sequence ranging from about amino acid residue 194-226 of SEQ ID NO: 153. In one embodiment, the antibody binds an epitope within EC2, or a fragment thereof, comprising an amino acid sequence ranging from amino acid residue 285-305 of SEQ ID NO: 153. In one embodiment, the antibody binds an epitope within EC3, or a fragment thereof, comprising an amino acid sequence ranging from about amino acid residue 369-384 of SEQ ID NO: 153.

In certain embodiments, the antibody or antibody fragment binds an epitope which includes more than one of the enumerated epitopes of GCGR within the N-terminal domain, or within EC1, EC2, or EC3, and/or within two or three different extracellular regions (for example, epitopes within the N-terminal region, EC1, EC2 and EC3 loops, or within EC1, EC2, and EC3, or within the N-terminal region, EC2 and EC3 loops, or within the N-terminal region, EC1 and EC3 loops.

In certain embodiments, the antibody is a bi-specific antibody that binds one epitope within one extracellular region of GCGR and another epitope within a different extracellular region of GCGR, including the N-terminal domain, or EC1, EC2, or EC3.

In one embodiment, the antibody is a bi-specific antibody that binds one epitope in the N-terminal region of hGCGR and another epitope in EC1 of hGCGR. In one embodiment, the antibody is a bi-specific antibody that binds one epitope in the N-terminal region of hGCGR and another epitope in EC1 of hGCGR. In one embodiment, the antibody is a bi-specific antibody that binds one epitope in the N-terminal region of hGCGR and another epitope in EC2 of hGCGR. In one embodiment, the antibody is a bi-specific antibody that binds one epitope in the N-terminal region of hGCGR and another epitope in EC3 of hGCGR. In one embodiment, the antibody is a bi-specific antibody that binds one epitope in EC1 of hGCGR and another epitope in EC2 of hGCGR. In one embodiment, the antibody is a bi-specific antibody that binds one epitope in EC1 of hGCGR and another epitope in EC3 of hGCGR. In one embodiment, the antibody is a bi-specific antibody that binds one epitope in EC2 of hGCGR and another epitope in EC3 of hGCGR.

In one embodiment, the antibody is a bi-specific antibody that binds one epitope in the N terminal domain of hGCGR, wherein the one epitope ranges from about residue 27 to about residue 144 of SEQ ID NO: 153 and a second epitope in EC1 of hGCGR, wherein the second epitope ranges from about residue number 194 to about residue number 226 of SEQ ID NO: 153. In one embodiment, the antibody is a bi-specific antibody that binds one epitope in the N terminal domain of hGCGR within the residues noted above, and a second epitope in EC2 of hGCGR, wherein the second epitope ranges from about residue number 285 to about residue number 305 of SEQ ID NO:153. In one embodiment, the antibody is a bi-specific antibody that binds one epitope in the N terminal domain of hGCGR within the residues noted above, and a second epitope in EC3 of hGCGR, wherein the second epitope ranges from about residue number 369 to about residue number 384 of SEQ ID NO: 153.

In one embodiment, the antibody is a bi-specific antibody that binds one epitope in EC1 of hGCGR from about residue 194 to about residue 226 of SEQ ID NO: 153 and a second epitope in EC2 of GCGR from about residue 285 to about residue 305 of SEQ ID NO: 153. In one embodiment, the antibody is a bi-specific antibody that binds one epitope in EC1 from about residue 194 to about residue 226 of SEQ ID NO: 153 and a second epitope in EC3 of GCGR from about residue 369 to about residue 384 of SEQ ID NO:153. In one embodiment, the antibody is a bi-specific antibody that binds one epitope in EC2 from about residue 285 to about residue 305 of SEQ ID NO:153 and a second epitope in EC3 of GCGR from about residue 369 to about residue 384 of SEQ ID NO:153.

The present invention includes anti-GCGR antibodies that bind to the same epitope as any of the specific exemplary antibodies described herein (e.g., H4H1345N, H4H1617N, H4H1765N, H4H1321B and H4H1321P, H4H1327B and H4H1327P, H4H1328B and H4H1328P, H4H1331B and H4H1331P, H4H1339B and H4H1339P). Likewise, the present invention also includes anti-GCGR antibodies that compete for binding to GCGR or a GCGR fragment with any of the specific exemplary antibodies described herein.

One can easily determine whether an antibody binds to the same epitope as, or competes for binding with, a reference anti-GCGR antibody by using routine methods known in the art. For example, to determine if a test antibody binds to the same epitope as a reference anti-GCGR antibody of the invention, the reference antibody is allowed to bind to a GCGR protein or peptide under saturating conditions. Next, the ability of a test antibody to bind to the GCGR molecule is assessed. If the test antibody is able to bind to GCGR following saturation binding with the reference anti-GCGR antibody, it can be concluded that the test antibody binds to a different epitope than the reference anti-GCGR antibody. On the other hand, if the test antibody is not able to bind to the GCGR molecule following saturation binding with the reference anti-GCGR antibody, then the test antibody may bind to the same epitope as the epitope bound by the reference anti-GCGR antibody of the invention.

To determine if an antibody competes for binding with a reference anti-GCGR antibody, the above-described binding methodology is performed in two orientations: In a first orientation, the reference antibody is allowed to bind to a GCGR molecule under saturating conditions followed by assessment of binding of the test antibody to the GCGR molecule. In a second orientation, the test antibody is allowed to bind to a GCGR molecule under saturating conditions followed by assessment of binding of the reference antibody to the GCGR molecule. If, in both orientations, only the first (saturating) antibody is capable of binding to the GCGR molecule, then it is concluded that the test antibody and the reference antibody compete for binding to GCGR. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Species Selectivity and Species Cross-Reactivity

According to certain embodiments of the invention, the anti-GCGR antibodies bind to human GCGR but not to GCGR from other species. Alternatively, the anti-GCGR antibodies of the invention, in certain embodiments, bind to human GCGR and to GCGR from one or more non-human species. For example, the anti-GCGR antibodies of the invention may bind to human GCGR and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee GCGR.

Immunoconjugates

The invention encompasses a human anti-GCGR monoclonal antibody conjugated to a therapeutic moiety ("immunoconjugate"), such as an agent that is capable of reducing blood glucose levels, or a radioisotope, or a chemotherapeutic agent. The type of therapeutic moiety that may be conjugated to the anti-GCGR antibody will take into account the condition to be treated and the desired therapeutic effect to be achieved. For example, for treating diabetes, or any other condition whereby it is desirable to lower blood glucose, and/or to maintain normal blood glucose levels, an agent such as biguanide (e.g. metformin), a sulfonylurea (e.g. glyburide, glipizide), a PPAR gamma agonist (e.g. pioglitazone, rosiglitazone); an alpha glucosidase inhibitor (e.g. acarbose, voglibose), an inhibitor of advanced glycation endproduct formation (e.g. aminoguanidine), or a second GCGR inhibitor may be conjugated to the GCGR antibody. Alternatively, if the desired therapeutic effect is to treat the sequelae or symptoms associated with diabetes, or any other condition resulting from high, or uncontrolled blood glucose levels, it may be advantageous to conjugate an agent appropriate to treat the sequelae or symptoms of the condition Examples of suitable agents for forming immunoconjugates are known in the art, see for example, WO 05/103081.

Multi-Specific Antibodies

The antibodies of the present invention may be mono-specific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-GCGR antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity. For example, the present invention includes bi-specific antibodies wherein one arm of an immunoglobulin is specific for human GCGR or a fragment thereof, and the other arm of the immunoglobulin is specific for a second therapeutic target or is conjugated to a therapeutic moiety. In certain embodiments of the invention, one arm of an immunoglobulin is specific for an epitope on the N-terminal domain of hGCGR or a fragment thereof, and the other arm of the immunoglobulin is specific for an epitope on one of the EC loops of hGCGR, or a fragment thereof. In certain embodiments, one arm of an immunoglobulin is specific for one EC loop, or a fragment thereof, and the second arm is specific for a second EC loop, or a fragment thereof. In certain embodiments, one arm of an immunoglobulin is specific for one epitope on one EC loop of hGCGR and the other arm is specific for a second epitope on the same EC loop of hGCGR.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R N384S, K392N, V397M, R409K, E419Q, and V422I by EU) in the case of IgG4 antibodies. Variations on the bi-specific antibody format described above are contemplated within the scope of the present invention.

Therapeutic Administration and Formulations

The invention provides therapeutic compositions comprising the anti-GCGR antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTINT™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When the antibody of the present invention is used for lowering blood glucose levels associated with GCGR activity in various conditions and diseases, such as diabetes, in an adult patient, it is advantageous to intravenously administer the antibody of the present invention normally at a single dose of about 0.01 to about 30 mg/kg body weight, more preferably about 0.02 to about 7, about 0.03 to about 5, or about 0.05 to about 3 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see, for example, Langer (1990) Science 249:1527-1533).

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousands Oaks, Calif.), the PENLET™ (Haselmeier, Stuttgart, Germany), the EPIPEN® (Dey, L. P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

Due to their interaction with the glucagon receptor, the present antibodies are useful for lowering blood glucose levels and also for the treatment of a wide range of conditions and disorders in which blocking the interaction of glucagon with its receptor is beneficial. These disorders and conditions may be selected from any glucagon related metabolic disorder, which involves glucagon receptor signaling that results in the pathophysiology of the disorder, or in the homeostatic response to the disorder. Thus, the antibodies may find use for example to prevent, treat, or alleviate, diseases or conditions or associated symptoms or sequelae, of the endocrine system, the central nervous system, the peripheral nervous system, the cardiovascular system, the pulmonary system, and the gastrointestinal system, while reducing and or eliminating one or more of the unwanted side effects associated with the current treatments. Glucagon related metabolic disorders include, but are not limited to, type 1 and type 2 diabetes, diabetic ketoacidosis, hyperglycemia, hyperglycemic hyperosmolar syndrome, perioperative hyperglycemia, hyperglycemia in the intensive care unit patient, hyperinsulinemia, postprandial hyperglycemia, impaired fasting glucose (IFG), metabolic syndrome, hyper-/hypokalemia, poor LDL/HDL ratio, eating disorders, weight gain, obesity as a consequence of diabetes, pediatric diabetes, gestational diabetes, diabetic late complications, micro-/macroalbuminuria, nephropathy, retinopathy, neuropathy, diabetic foot ulcers, wound healing, impaired glucose tolerance (IGT), insulin resistance syndromes, syndrome X, glucagonomas, gastrointestinal disorders, obesity, diabetes as a consequence of obesity, etc. The present invention further provides; a method of treating conditions resulting from excessive glucagon in a mammal; a method of inhibiting the glucagon receptor in a mammal; a method of inhibiting a glucagon receptor mediated cellular response in a mammal, or a method of reducing the glycemic level in a mammal comprising administering to a mammal in need of such treatment a glucagon receptor-inhibiting amount of an anti-GCGR antibody or a biologically active fragment thereof.

The present antibodies are effective in lowering blood glucose, both in the fasting and the postprandial stage. In certain embodiments of the invention, the present antibodies are used for the preparation of a pharmaceutical composition for the treatment of type 2 diabetes. In yet a further embodiment of the invention the present antibodies are used for the preparation of a pharmaceutical composition for the delaying or prevention of the progression from impaired glucose tolerance to type 2 diabetes. In yet another embodiment of the invention the present antibodies are used for the preparation of a pharmaceutical composition for the delaying or prevention of the progression from non-insulin requiring diabetes to insulin requiring diabetes. In a further embodiment of the invention the present antibodies are used for the preparation of a pharmaceutical composition for the treatment of type 1 diabetes. Such treatment is normally accompanied by insulin therapy.

Combination Therapies

Combination therapies may include an anti-hGCGR antibody of the invention and any additional therapeutic agent that may be advantageously combined with an antibody of the invention, or with a biologically active fragment of an antibody of the invention.

For example, a second therapeutic agent may be employed to aid in further lowering of glucose levels, or to reduce at least one symptom in a patient suffering from a disease or condition characterized by high blood glucose levels, such as diabetes mellitus. Such a second agent may be selected from, for example, a glucagon antagonist or another GCGR antagonist (e.g. an anti-glucagon or anti-GCGR antibody or small molecule inhibitor of glucagon or GCGR), or may include other therapeutic moieties useful for treating diabetes, or other diseases or conditions associated with, or resulting from elevated blood glucose levels, or impaired glucose metabolism, or agents useful for treating any long term complications associated with elevated and/or uncontrolled blood glucose levels. These agents include biguanides, which decrease glucose production in the liver and increase sensitivity to insulin (e.g. metformin), or sulfonylureas, which stimulate insulin production (e.g. glyburide, glipizide). Additional treatments directed at maintaining glucose homeostasis including PPAR gamma agonists, which act as insulin sensitizers (e.g. pioglitazone, rosiglitazone); and alpha glucosidase inhibitors, which slow starch absorption and glucose production (e.g. acarbose, voglibose). Additional treatments include injectable treatments such as Exenatide® (glucagon-like peptide 1), and Symlin® (pramlintide).

In certain other embodiments, the composition may include a second agent selected from the group consisting of non-sulfonylurea secretagogues, insulin, insulin analogs, exendin-4 polypeptides, beta 3 adrenoceptor agonists, PPAR agonists, dipeptidyl peptidase IV inhibitors, statins and statin-containing combinations, cholesterol absorption inhibitors, LDL-cholesterol antagonists, cholesteryl ester transfer protein antagonists, endothelin receptor antagonists, growth hormone antagonists, insulin sensitizers, amylin mimetics or agonists, cannabinoid receptor antagonists, glucagon-like peptide-1 agonists, melanocortins, melanin-concentrating hormone receptor agonists, SNRIs, and protein tyrosine phosphatase inhibitors.

In certain other embodiments, combination therapy may include administration of a second agent to counteract any potential side effect(s) resulting from administration of an antibody of the invention, if such side effect(s) occur. For example, in the event that any of the anti-GCGR antibodies increases lipid or cholesterol levels, it may be beneficial to administer a second agent to lower lipid or cholesterol levels, using an agent such as a HMG-CoA reductase inhibitor (for example, a statin such as atorvastatin, (LIPITOR®), fluvastatin (LESCOL®), lovastatin (MEVACOR®), pitavastatin (LIVALO®), pravastatin (PRAVACHOL®), rosuvastatin (CRESTOR®) and simvastatin (ZOCOR®). Alternatively, the antibodies of the invention may be combined with an agent such as VYTORIN®, which is a preparation of a statin and another agent—such as ezetimibe/simvastatin.

In certain embodiments, it may be beneficial to administer the antibodies of the invention in combination with any one or more of the following: (1) niacin, which increases lipoprotein catabolism; (2) fibrates or amphipathic carboxylic acids, which reduce low-density lipoprotein (LDL) level, improve high-density lipoprotein (HDL) and TG levels, and reduce the number of non-fatal heart attacks; and (3) activators of the LXR transcription factor that plays a role in cholesterol elimination such as 22-hydroxycholesterol, or a statin with a bile resin (e.g., cholestyramine, colestipol, colesevelam), a fixed combination of niacin plus a statin (e.g., niacin with lovastatin); or with other lipid lowering agents such as omega-3-fatty acid ethyl esters (for example, omacor).

Furthermore, the second therapeutic agent can be one or more other inhibitors of glucagon or GCGR, as well as inhibitors of other molecules, such as angiopoietin-like protein 3 (ANGPTL3), angiopoietin-like protein 4 (ANGPTL4), angiopoietin-like protein 5 (ANGPTL5), angiopoietin-like protein 6 (ANGPTL6), which are involved in lipid metabolism, in particular, cholesterol and/or triglyceride homeostasis. Inhibitors of these molecules include small molecules and antibodies that specifically bind to these molecules and block their activity.

In certain embodiments, it may be beneficial to administer the antibodies of the invention in combination with an antibody that acts to lower lipid or cholesterol levels, such as, but not limited to, for example, any anti-PCSK9 (proprotein convertase subtilisin/kexin type 9) antibody, such as those described in US2010/0166768, now U.S. Pat. No. 8,062,640. Other anti-PCSK9 antibodies are described in US2010/0040611, US2010/0041102, US2010/0040610, US2010/0113575, now U.S. Pat. No. 8,263,353, US2009/0232795, now U.S. Pat. No. 8,188,233, US2009/0246192, now U.S. Pat. No. 8,188,234, US2010/0233177, US2009/0142352, now U.S. Pat. No. 8,030,457, US2009/0326202, now U.S. Pat. No. 8,563,698, US2010/0068199, now U.S. Pat. No. 8,080,243, US2011/0033465, now U.S. Pat. No. 8,598,320, US2011/0027287, US2010/0150937, US2010/0136028 and WO2009/055783.

In certain embodiments, it may be beneficial to administer the anti-GCGR antibodies of the invention in combination with a nucleic acid that inhibits the activity of PCSK9 (proprotein convertase subtilisin/kexin type 9), such as an antisense molecule, a double stranded RNA, or a siRNA molecule. Exemplary nucleic acid molecules that inhibit the activity of PCSK9 are described in US2011/0065644, US2011/0039914, US2008/0015162, now U.S. Pat. No. 9,045,754, and US2007/0173473.

The additional therapeutically active component(s) may be administered prior to, concurrent with, or after the administration of the anti-GCGR antibody of the present invention. For purposes of the present disclosure, such administration regimens are considered the administration of an anti-GCGR antibody "in combination with" a second therapeutically active component.

Administration Regimens

According to certain embodiments of the present invention, multiple doses of one or more anti-GCGR antibodies (an antibody combination) or a bi-specific antigen-binding molecule may be administered to a subject over a defined time course. The methods according to this aspect of the invention comprise sequentially administering to a subject multiple doses of an antibody, antibody combination, or a bi-specific antigen-binding molecule of the invention. As used herein, "sequentially administering" means that each dose of an antibody, antibody combination, or a bi-specific antigen-binding molecule is administered to the subject at a different point in time, e.g., on different days separated by a predetermined interval (e.g., hours, days, weeks or months). The present invention includes methods, which comprise sequentially administering to the patient a single initial dose of an antibody, antibody combination, or a bi-specific antigen-binding molecule, followed by one or more secondary doses of the antibody, and optionally followed by one or more tertiary doses of the antibody.

The terms "initial dose," "secondary doses," and "tertiary doses," refer to the temporal sequence of administration of an antibody, antibody combination, or a bi-specific antigen-binding molecule of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of an antibody, antibody combination, or a bi-specific antigen-binding molecule, but generally may differ from one another in terms of frequency of administration. In certain embodiments, however, the amount of an antibody, antibody combination, or a bi-specific antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of an antibody, antibody combination, or a bi-specific antigen-binding molecule, which is administered to a patient prior to the administration of the very next dose in the sequence with no intervening doses.

The methods according to this aspect of the invention may comprise administering to a patient any number of secondary and/or tertiary doses of an antibody, antibody combination, or a bi-specific antigen-binding molecule that specifically binds Fel d1. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-GCGR antibodies of the present invention may also be used to detect and/or measure GCGR in a sample, e.g., for diagnostic purposes. For example, an anti-GCGR antibody, or fragment thereof, may be used to diagnose a condition or disease characterized by aberrant expression (e.g., over-expression, under-expression, lack of expression, etc.) of GCGR. Exemplary diagnostic assays for GCGR may comprise, e.g., contacting a sample, obtained from a patient, with an anti-GCGR antibody of the invention, wherein the anti-GCGR antibody is labeled with a detectable label or reporter molecule or used as a capture ligand to selectively isolate GCGR protein from patient samples. Alternatively, an unlabeled anti-GCGR antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$;

a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure GCGR in a sample include enzyme-linked immunosorbent assay (ELISA), radioimmunoassay (RIA), and fluorescence-activated cell sorting (FACS).

Samples that can be used in GCGR diagnostic assays according to the present invention include any tissue or fluid sample obtainable from a patient, which contains detectable quantities of GCGR protein, or fragments thereof, under normal or pathological conditions. Generally, levels of GCGR in a particular sample obtained from a healthy patient (e.g., a patient not afflicted with a disease or condition associated with abnormal GCGR levels or activity) will be measured to initially establish a baseline, or standard, level of GCGR. This baseline level of GCGR can then be compared against the levels of GCGR measured in samples obtained from individuals suspected of having a GCGR related disease or condition, or symptoms associated with such disease or condition.

EXAMPLES

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, preferred methods and materials are now described. All publications mentioned herein are incorporated herein by reference in their entirety.

Example 1

Generation of Human Antibodies to Human GCGR

An immunogen comprising any one of the following can be used to generate antibodies to hGCGR. For example, cells expressing hGCGR were used in certain embodiments as an immunogen to generate antibodies to hGCGR. Additionally, DNA encoding hGCGR was used in certain embodiments as an immunogen to prepare the antibodies of the invention.

Furthermore, in certain embodiments, peptides comprising amino acid sequences from the N-terminal domain of hGCGR were utilized as an immunogen to generate antibodies to human GCGR. In addition, in certain embodiments, peptides comprising amino acid sequences from any of the extracellular loop regions EC1, EC2, or EC3, of hGCGR may be utilized as an immunogen to generate antibodies to human GCGR. The cells, DNA, or peptides that were used as immunogens, as noted above, were administered directly, with an adjuvant to stimulate the immune response, to a VELOCIMMUNE® mouse comprising DNA encoding human Immunoglobulin heavy and kappa light chain variable regions. The antibody immune response was monitored by a GCGR-specific immunoassay. When a desired immune response was achieved splenocytes were harvested and fused with mouse myeloma cells to preserve their viability and form hybridoma cell lines. The hybridoma cell lines were screened and selected to identify cell lines that produce GCGR-specific antibodies. Using this technique, and the various immunogens described above, several anti-GCGR chimeric antibodies (i.e., antibodies possessing human variable domains and mouse constant domains) were obtained; certain exemplary antibodies generated in this manner were designated as H4H1345N, H4H1617N and H4H1765N.

Anti-GCGR antibodies were also isolated directly from antigen-positive B cells without fusion to myeloma cells, as described in U.S. 2007/0280945A1, herein specifically incorporated by reference in its entirety. Using this method, several fully human anti-GCGR antibodies (i.e., antibodies possessing human variable domains and human constant domains) were obtained; exemplary antibodies generated in this manner were designated as follows: H4H1321B, H4H1321P, H4H1327B, H4H1327P, H4H1328B, H4H1328P, H4H1331B, H4H1331P, H4H1339B and H4H1339P.

The biological properties of the exemplary anti-GCGR antibodies generated in accordance with the methods of this Example are described in detail in the Examples set forth below.

Example 2

Heavy and Light Chain Variable Region Amino Acid Sequences

Table 1 sets forth the heavy and light chain variable region amino acid sequence pairs of selected anti-GCGR antibodies and their corresponding antibody identifiers. Antibodies having the same numerical antibody designation, but differing by a letter suffix of N, B or P refer to antibodies having heavy and light chains with identical CDR sequences but with sequence variations in regions that fall outside of the CDR sequences (i.e., in the framework regions). Thus, N, B and P variants of a particular antibody have identical CDR sequences within their heavy and light chain variable regions but differ from one another within their framework regions.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H1345N | 2 | 4 | 6 | 8 | 10 | 12 | 14 | 16 |
| H4H1617N | 18 | 20 | 22 | 24 | 26 | 28 | 30 | 32 |
| H4H1765N | 34 | 36 | 38 | 40 | 42 | 44 | 46 | 48 |
| H4H1321B | 50 | 52 | 54 | 56 | 58 | 60 | 62 | 64 |
| H4H1321P | 66 | 52 | 54 | 56 | 68 | 60 | 62 | 64 |

TABLE 1-continued

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H1327B | 70 | 72 | 74 | 76 | 78 | 80 | 82 | 84 |
| H4H1327P | 86 | 72 | 74 | 76 | 88 | 80 | 82 | 84 |
| H4H1328B | 90 | 92 | 94 | 96 | 98 | 100 | 102 | 104 |
| H4H1328P | 106 | 92 | 94 | 96 | 108 | 100 | 102 | 104 |
| H4H1331B | 110 | 112 | 114 | 116 | 118 | 120 | 122 | 124 |
| H4H1331P | 126 | 112 | 114 | 116 | 128 | 120 | 122 | 124 |
| H4H1339B | 130 | 132 | 134 | 136 | 138 | 140 | 142 | 144 |
| H4H1339P | 146 | 132 | 134 | 136 | 148 | 140 | 142 | 144 |

Example 3

Variable Gene Utilization Analysis

To analyze the structure of antibodies produced, the nucleic acids encoding antibody variable regions were cloned and sequenced. From the nucleic acid sequence and predicted amino acid sequence of the antibodies, gene usage was identified for each Heavy Chain Variable Region (HCVR) and Light Chain Variable Region (LCVR). Table 2 sets forth the gene usage for selected antibodies in accordance with the invention.

TABLE 2

| Antibody | Antibody Identifier HCVR/LCVR SEQ ID NOs | HCVR | | | LCVR | |
|---|---|---|---|---|---|---|
| | | $V_H$ | $D_H$ | $J_H$ | $V_K$ | $J_K$ |
| H4H1617N | 18/26 | V1-24 | D3-9 | J6 | V2-28 | J1 |
| H4H1345N | 2/10 | V1-24 | D3-9 | J6 | V2-28 | J1 |
| H4H1765N | 34/42 | V3-48 | D6-6 | J6 | V2-28 | J1 |
| H4H1321P | 66/68 | V3-30 | D3-9 | J6 | V1-16 | J4 |
| H4H1327P | 86/88 | V3-7 | D3-9 | J6 | V1-17 | J3 |
| H4H1328P | 106/108 | V3-13 | D3-9 | J6 | V1-17 | J4 |
| H4H1331P | 126/128 | V3-33 | D3-9 | J6 | V1-17 | J1/J4 |
| H4H1339P | 146/148 | V3-13 | D3-9 | J6 | V1-6 | J1 |

Example 4

Antibody Binding to Soluble GCGR as Determined by Surface Plasmon Resonance

Binding affinities and kinetic constants of human monoclonal anti-hGCGR antibodies binding to human and monkey soluble recombinant hGCGR ectodomain (hGCGR and MfGCGR, respectively) were determined by surface plasmon resonance at both 25° C. and 37° C. Measurements were conducted on a T100 Biacore instrument. Antibodies were captured onto the Biacore sensor chip surface via a covalently-linked anti-human kappa antibody capture surface, and the soluble GCGR proteins were applied to the surface either in a monovalent (hGCGR expressed with a myc-myc-hexa-histidine C-terminal tag) or bivalent (hGCGR and MfGCGR expressed with an N-terminal Fc fusion) format. The amino acid sequence identifiers of the reagents used in this example are shown in Table 3.

TABLE 3

| Description | Construct | SEQ ID NO: |
|---|---|---|
| anti-GCGR positive control hIgG4(S108P) | 150 kDa, dimer | (See Yan, Hai et al. WO2008/036341) |
| mfGCGR-N-terminal hFc | 160 k | 152 |
| hGCGR-mFc | 80654.42 Da, dimer | 149 |
| hGCGR-mmh | 18,965 Da, monomer | 151 |

The soluble GCGR was applied to the flow cell in separate injections at multiple concentrations ranging from 3.1 nM to 50 nM, and kinetic association ($k_a$) and dissociation ($k_d$) rate constants were determined by fitting the data to a 1:1 binding model using Scrubber v2.0a curve fitting software. Binding dissociation equilibrium constants and dissociative half-lives were calculated from the kinetic rate constants as: $K_D = k_d/k_a$; $t_{1/2} = (\ln 2/k_d)$.

TABLE 4a

| Biacore data for binding at 25° C. | | | | | |
|---|---|---|---|---|---|
| Antibody Designation | Antigen tested | ka | kd | $K_D$ | T½ (min) |
| H4H1321P | hGCGR-mmh | 1.06E+06 | 3.74E−03 | 3.54E−09 | 3 |
| | hGCGR-hFc | 1.20E+06 | 2.85E−04 | 2.38E−10 | 41 |
| | mfGCGR-hFc | 1.76E+06 | 4.18E−05 | 2.38E−11 | 276 |
| H4H1327P | hGCGR-mmh | 9.52E+05 | 3.52E−04 | 3.69E−10 | 33 |
| | hGCGR-hFc | 1.21E+06 | 4.10E−05 | 3.38E−11 | 282 |
| | mfGCGR-hFc | 1.60E+06 | 1.44E−05 | 9.02E−12 | 802 |
| H4H1328P | hGCGR-mmh | 1.03E+06 | 2.12E−03 | 2.06E−09 | 5 |
| | hGCGR-hFc | 1.13E+06 | 2.26E−04 | 2.01E−10 | 51 |
| | mfGCGR-hFc | 1.60E+06 | 8.46E−05 | 5.29E−11 | 137 |
| H4H1331P | hGCGR-mmh | 6.57E+05 | 1.11E−04 | 1.70E−10 | 104 |
| | hGCGR-hFc | 7.60E+05 | 1.54E−05 | 2.02E−11 | 751 |
| | mfGCGR-hFc | 1.17E+06 | 8.12E−06 | 6.90E−12 | 1423 |

TABLE 4a-continued

Biacore data for binding at 25° C.

| Antibody Designation | Antigen tested | ka | kd | $K_D$ | T½ (min) |
|---|---|---|---|---|---|
| H4H1339P | hGCGR-mmh | 6.45E+05 | 5.32E−04 | 8.25E−10 | 22 |
| | hGCGR-hFc | 1.00E+06 | 6.20E−05 | 6.18E−11 | 186 |
| | mfGCGR-hFc | 1.26E+06 | 2.28E−05 | 1.82E−11 | 506 |
| H4H1345N | hGCGR-mmh | 7.98E+05 | 3.44E−04 | 4.31E−10 | 34 |
| | hGCGR-hFc | 7.90E+05 | 5.72E−05 | 7.24E−11 | 202 |
| | mfGCGR-hFc | 9.53E+05 | 2.42E−05 | 2.54E−11 | 477 |
| H4H1617N | hGCGR-mmh | 1.07E+06 | 1.99E−04 | 1.87E−10 | 58 |
| | hGCGR-hFc | 8.18E+05 | 3.18E−05 | 3.89E−11 | 363 |
| | mfGCGR-hFc | 1.26E+06 | 1.38E−05 | 1.10E−11 | 835 |
| H4H1765N | hGCGR-mmh | 3.26E+05 | 3.05E−05 | 9.30E−11 | 379 |
| | hGCGR-hFc | 4.10E+05 | 4.95E−06 | 1.22E−11 | 2331 |
| | mfGCGR-hFc | 6.43E+05 | 1.00E−06 | 1.56E−12 | 11550 |
| Isotype-matched comparator antibody | hGCGR-mmh | 6.67E+05 | 1.68E−04 | 2.52E−10 | 69 |
| | hGCGR-hFc | 8.21E+05 | 2.04E−05 | 2.49E−11 | 565 |
| | mfGCGR-hFc | 1.23E+06 | 6.09E−06 | 4.95E−12 | 1897 |

TABLE 4b

Biacore data for binding at 37° C.

| Antibody Designation | Antigen tested | ka | kd | $K_D$ | T½ (min) |
|---|---|---|---|---|---|
| H4H1321P | hGCGR-mmh | 1.58E+06 | 2.02E−02 | 1.28E−08 | 1 |
| | hGCGR-hFc | 1.41E+06 | 1.09E−04 | 7.70E−11 | 106 |
| | mfGCGR-hFc | 2.19E+06 | 7.59E−05 | 3.47E−11 | 152 |
| H4H1327P | hGCGR-mmh | 1.48E+06 | 2.00E−03 | 1.35E−09 | 6 |
| | hGCGR-hFc | 1.48E+06 | 2.32E−04 | 1.57E−10 | 50 |
| | mfGCGR-hFc | 2.22E+06 | 7.94E−05 | 3.57E−11 | 145 |
| H4H1328P | hGCGR-mmh | 1.61E+06 | 1.08E−02 | 6.67E−09 | 1 |
| | hGCGR-hFc | 1.55E+06 | 1.92E−04 | 1.24E−10 | 60 |
| | mfGCGR-hFc | 2.03E+06 | 7.17E−05 | 3.53E−11 | 161 |
| H4H1331P | hGCGR-mmh | 9.73E+05 | 5.19E−04 | 5.33E−10 | 22 |
| | hGCGR-hFc | 1.17E+06 | 9.12E−05 | 7.79E−11 | 127 |
| | mfGCGR-hFc | 1.60E+06 | 4.12E−05 | 2.57E−11 | 281 |
| H4H1339P | hGCGR-mmh | 8.76E+05 | 4.30E−03 | 4.91E−09 | 3 |
| | hGCGR-hFc | 1.17E+06 | 3.71E−04 | 3.18E−10 | 31 |
| | mfGCGR-hFc | 1.69E+06 | 1.07E−04 | 6.31E−11 | 108 |
| H4H1345N | hGCGR-mmh | 9.28E+05 | 1.97E−03 | 2.12E−09 | 6 |
| | hGCGR-hFc | 9.52E+05 | 3.09E−04 | 3.24E−10 | 37 |
| | mfGCGR-hFc | 1.27E+06 | 1.28E−04 | 1.01E−10 | 91 |
| H4H1617N | hGCGR-mmh | 1.20E+06 | 1.13E−03 | 9.43E−10 | 10 |
| | hGCGR-hFc | 1.18E+06 | 2.14E−04 | 1.81E−10 | 54 |
| | mfGCGR-hFc | 1.49E+06 | 8.72E−05 | 5.86E−11 | 133 |
| H4H1765N | hGCGR-mmh | 4.41E+05 | 1.11E−04 | 2.52E−10 | 104 |
| | hGCGR-hFc | 6.64E+05 | 3.57E−05 | 5.37E−11 | 324 |
| | mfGCGR-hFc | 9.04E+05 | 1.48E−05 | 1.64E−11 | 778 |
| Isotype-matched comparator antibody | hGCGR-mmh | 8.73E+05 | 1.46E−03 | 1.68E−09 | 8 |
| | hGCGR-hFc | 1.15E+06 | 1.82E−04 | 1.59E−10 | 63 |
| | mfGCGR-hFc | 1.66E+06 | 6.27E−05 | 3.77E−11 | 184 |

As shown in Tables 4a and 4b, the exemplary antibodies exhibited high affinity binding to both human and monkey GCGR soluble proteins. A significant increase in binding affinity (5-fold to 15-fold) was observed when flowing the bivalent hGCGR in comparison to monovalent hGCGR. The antibodies consistently bound with higher affinity (3-fold to 10-fold) to the monkey variant, MfGCGR, compared to hGCGR.

Example 5

Bioassay to Measure the Effects of Anti-GCGR Antibodies on GCGR Activation

GCGR is a G-protein coupled receptor and its ligand, glucagon (GCG), stimulates adenylyl cyclase activity through Gαs and phosphoinositol turnover through Gq (Jiang and Zhang, (2003), Am J Physiol Endocrinol Metab 284: E671-E678). A bioassay was developed to detect activation through Gαs, subsequent elevation of cAMP levels and transcriptional activation. HEK293 cell lines were generated to stably express full-lengths of human GCGR (GenBank accession number NP_000151.1; SEQ ID NO: 153), monkey (*Macaca fascicularis*) GCGR (SEQ ID NO: 155), and mouse GCGR (NP_032127.2; SEQ ID NO: 154.) along with a luciferase reporter assay. The stable cell lines were isolated and maintained in 10% FBS, DMEM, NEAA, Pen/Strep, and 500 mg/ml G418. For rat GCGR, the HEK293 cell line expressing the reporter gene [CRE (4x)-luciferase-IRES-GFP] was transiently transfected with full-length rat GCGR (NP_742089.1; SEQ ID NO: 156) using Lipofectamine-2000 (Invitrogen).

For the bioassay, 293/GCGR cells were seeded onto 96-well assay plates at 20,000 cells/well in low serum media, 0.1% FBS and OPTIMEM®, and incubated at 37° C. and 5%

$CO_2$ overnight. Next day, GCG was serially diluted at 1:3 and added to cells starting from 100 nM to 0.002 nM including no GCG control for dose response. For inhibition, antibodies were serially diluted at 1:3 and added to cells starting from 200 to 0.003 (for hGCGR cells) or 100 nM to 0.002 nM (for monkey, mouse and rat GCGR cells) including no antibody control with constant concentration of 100 pM GCG. Luciferase activity was detected after 5.5 hrs of incubation in 37° C. and 5% $CO_2$.

EC50 values for stimulation of each reporter cell-line by 100 pM GCG are shown in Table 5a. The results of the IC50 values for antibodies blocking stimulation of cells by 100 pM GCG are shown in Table 5b, including the results for two control antibodies, Control mAb1 (positive control expressed as hIgG4 isotype; for example, see WO2008/036341 for the antibody designated as "A-9" having the HCVR of SEQ ID NO: 275, HCDR1 of SEQ ID NO: 102, HCDR2 of SEQ ID NO: 128, and HCDR3 of SEQ ID NO: 169 and the LCVR of SEQ ID NO: 229, LCDR1 of SEQ ID NO: 14, LCDR2 of SEQ ID NO: 50 and the LCDR3 of SEQ ID NO: 74) and Control mAb2 (an isotype-matched negative control).

Regarding the inhibition of human GCGR by anti-GCGR antibodies, the activation of GCGR by GCG was shown to stimulate luciferase activity with an EC50 of 113 pM and all antibodies except Control mAb2 (isotype matched negative control) blocked the activation of GCG at 100 pM and decreased the luciferase activity.

With respect to the inhibition of monkey GCGR by anti-GCGR antibodies, the activation of GCGR by GCG was shown to stimulate luciferase activity with an EC50 of 36 pM and all antibodies except Control mAb2 (isotype matched negative control) blocked the activation of GCG at 100 pM and decreased the luciferase activity. H4H1765N showed a partial inhibition of GCG at highest concentration of antibody tested, 100 nM.

Regarding the inhibition of mouse GCGR by anti-GCGR antibodies, the activation of GCGR by GCG was shown to stimulate luciferase activity with an EC50 of 83 pM and all antibodies except H4H1345N, H4H1617N, H4H1765N and Control mAb2 (isotype matched negative control) blocked the activation of GCG at 100 pM and decreased the luciferase activity.

With respect to the inhibition of rat GCGR by anti-GCGR antibodies, the activation of GCGR by GCG was shown to stimulate luciferase activity with an EC50 of 252 pM and all antibodies except H4H1765N and Control mAb2 (isotype matched negative control) blocked the activation of GCG at 100 pM and decreased the luciferase activity.

TABLE 5a

| Cell lines | hGCGR | mfGCGR | mGCGR | rat GCGR |
|---|---|---|---|---|
| EC50 (pM) | 113 | 36 | 83 | 252 |
| Constant GCG (pM) | | | 100 | |

TABLE 5b

| Antibody Designation | IC50 (nM) | | | |
|---|---|---|---|---|
| | hGCGR | mfGCGR | mGCGR | rat GCGR |
| H4H1321P | 0.27 | 4.03 | 1.13 | 1.21 |
| H4H1327P | 0.39 | 2.56 | 1.04 | 0.88 |
| H4H1328P | 0.24 | 2.73 | 1.26 | 0.93 |
| H4H1331P | 0.66 | 8.29 | 1.62 | 3.87 |
| H4H1339P | 0.46 | 2.85 | 1.60 | 0.97 |

TABLE 5b-continued

| Antibody Designation | IC50 (nM) | | | |
|---|---|---|---|---|
| | hGCGR | mfGCGR | mGCGR | rat GCGR |
| H4H1345N | 2.22 | 3.86 | Not Blocked | 8.07 |
| H4H1617N | 1.25 | 4.24 | Not Blocked | 3.66 |
| H4H1765N | 12.78 | 75.16 | Not Blocked | Not Blocked |
| Control mAb1 Positive control | 0.30 | 2.38 | 1.69 | 0.69 |
| Control mAb2 Negative control | Not Blocked | Not Blocked | Not Blocked | Not Blocked |

In summary, eight anti-hGCGR fully-human antibodies were tested and demonstrated blocking of activation of human GCGR by 100 pM GCG in a reporter cell line that exhibited an EC50 of 113 pM when stimulated by GCG alone. In the monkey GCGR reporter cell line, seven out of eight tested antibodies fully inhibited activation by 100 pM GCG. H4H1765N did not fully inhibit monkey GCGR at the highest concentration of antibody tested, 100 nM. Five out of eight of the antibodies fully inhibited the activation by 100 pM GCG in the mouse GCGR reporter cell line, and seven out of eight antibodies inhibited the activation by 100 pM GCG in the rat GCGR-transfected reporter cells.

Example 6

Effect of Anti-GCGR Antibodies in Ob/Ob Mice

Selected anti-hGCGR antibodies, all of which cross-react with mouse GCGR, were tested for their ability to reduce blood glucose levels in ob/ob mice, a mouse model of type 2 diabetes. ob/ob mice were put into ten groups of five or six animals. Each group received subcutaneous injections of each antibody at 1 or 10 mg/kg. The control group was injected with a hIgG isotype control antibody, which does not bind to any known mouse proteins. Two or seven days after antibody dosing at 1 or 10 mg/kg, respectively, a few drops of blood obtained by tail bleeds were collected from mice. Specifically, for the group given the antibody designated H4H1327P at 10 mg/kg, tail bleeds were collected more frequently at 2, 4, 7, 9, 11, 14, 16, 18, and 21 days after dosing. Blood glucose levels from the tail bleed samples were determined by ACCU-CHEK® Compact Plus (Roche). The percent reduction in blood glucose from the mean blood glucose levels of the control group was calculated for each animal at each time point. The average percent reduction in blood glucose was calculated for each antibody group. Table 6 summarizes the mean blood glucose levels of the control group. Results, expressed as (mean±SEM) of percent blood glucose reduction, are shown in Tables 7a and 7b.

TABLE 6

| Time | Blood glucose (mg/dL) |
|---|---|
| Day 0 | 197 ± 14 |
| Day 2 | 185 ± 13 |
| Day 4 | 167 ± 6 |
| Day 7 | 202 ± 20 |
| Day 9 | 205 ± 18 |
| Day 11 | 195 ± 23 |

TABLE 6-continued

| Time | Blood glucose (mg/dL) |
|---|---|
| Day 14 | 229 ± 13 |
| Day 16 | 206 ± 6 |
| Day 18 | 187 ± 11 |
| Day 21 | 209 ± 16 |

TABLE 7a

| Dosage | Time (days) | Blood glucose reduction (%) Antibody Designation | | | |
|---|---|---|---|---|---|
| | | H4H1327P | H4H1328P | H4H1331P | H4H1339P |
| 1 mg/kg | 2 | 49 ± 1 | 45 ± 2 | 46 ± 2 | 46 ± 2 |
| 10 mg/kg | 7 | 53 ± 2 | 50 ± 2 | 55 ± 2 | 52 ± 2 |

TABLE 7b

| Antibody Designation | Blood glucose reduction (%) Time (days) | | | | | | | | |
|---|---|---|---|---|---|---|---|---|---|
| | 2 | 4 | 7 | 9 | 11 | 14 | 16 | 18 | 21 |
| H4H1327P | 58 ± 2 | 52 ± 2 | 53 ± 2 | 56 ± 2 | 47 ± 3 | 51 ± 3 | 45 ± 4 | 34 ± 5 | −5 ± 17 |

Mice treated with the anti-hGCGR antibodies tested (shown in Tables 7a and 7b) exhibited significant reductions in blood glucose levels compared to mice injected with control antibody.

Example 7

Effect of Anti-GCGR Antibodies in Transgenic Mice Expressing the Human GCGR Protein The effects of anti-hGCGR antibodies on blood glucose and plasma lipid levels were determined in transgenic mice expressing the human GCGR protein ("humanized GCGR mice"). Humanized GCGR mice were generated by replacing the mouse GCGR gene with the human GCGR gene (SEQ ID NO: 157; encoding full-length protein, GenBank accession number NP_000151.1; SEQ ID NO: 153) in C57BL6/129 (F1H4) embryonic stem cells. After germ line transmission was established, heterozygous mice (GCGR$^{hum/+}$) were bred together to generate homozygous mice (GCGR$^{hum/hum}$) on a C57BL6 background. Homozygous humanized GCGR mice were put into ten groups of three or four animals. Each group received subcutaneous injections of each antibody at 3 mg/kg. The Control I group was injected with a hIgG isotype negative control antibody, which does not bind to any known mouse proteins. The Control II group was injected with an anti-hGCGR hIgG4 positive control/comparator antibody (See WO2008/036341 for the "A9" antibody sequence), which has been validated to decrease blood glucose levels of humanized GCGR mice. Mice were bled three days after antibody dosing, and blood glucose levels were determined by ACCU-CHEK® Compact Plus (Roche). The percent reduction in blood glucose from the mean blood glucose levels of the Control I group was calculated for each animal. The average percent reduction in blood glucose was calculated for each antibody group. Table 8a summarizes the mean blood glucose levels of the negative control group. Results, expressed as (mean±SEM) of percent blood glucose reduction in animals treated with either the positive Control II comparator antibody, or the test anti-GCGR antibodies as compared to the negative control group, are shown in Table 8b.

Additionally with the Control I, Control II and H4H1765N groups, mice were bled before and 3 and 8 days after antibody dosing, and plasma lipid levels were determined by ADVIA® 1650 Chemistry System (Siemens). Averages were calculated for each of the measurements of low density lipoprotein cholesterol (LDL-C), high density lipoprotein cholesterol (HDL-C), total cholesterol (TOTAL-C), triglycerides (TG), nonesterified fatty acids (NEFA) levels for each of the three groups. Results, expressed as (mean±SEM) of plasma lipid concentrations, are shown in Table 8c.

Mice treated with most of the anti-hGCGR antibodies tested (shown in Table 8b) exhibited significant reductions in blood glucose levels similar to mice receiving the positive control II antibody. Mice treated with certain of the anti-hGCGR antibodies tested (e.g. H4H1765N, shown in Table 8c) exhibited significant reductions in triglyceride levels compared to mice receiving negative Control I antibody. In particular, the lowering of triglyceride levels was observed with two anti-GCGR antibodies, one designated as H4H1765N (data shown below in Table 8c) and the other designated as H4H1327P (data not shown).

TABLE 8a

| Time | Blood glucose (mg/dL) |
|---|---|
| Day 0 | 155 ± 6 |
| Day 1 | 160 ± 5 |
| Day 3 | 155 ± 5 |
| Day 6 | 164 ± 7 |
| Day 8 | 156 ± 7 |
| Day 10 | 154 ± 9 |
| Day 13 | 149 ± 5 |

TABLE 8b

| Antibody Designation | Blood glucose reduction (%) |
|---|---|
| Control II | 37 ± 3 |
| H4H1321P | 32 ± 4 |
| H4H1327P | 40 ± 7 |
| H4H1328P | 31 ± 7 |
| H4H1331P | 33 ± 4 |
| H4H1339P | 31 ± 6 |
| H4H1617N | 15 ± 5 |
| H4H1345N | 14 ± 2 |
| H4H1765N | 32 ± 4 |

TABLE 8c

| Antibody Designation | Time (days) | LDL-C (mg/dL) | HDL-C (mg/dL) | TOTAL-C (mg/dL) | TG (mg/dL) | NEFA (mmol/L) |
|---|---|---|---|---|---|---|
| Control I | Pre | 9.4 ± 1.4 | 47 ± 4 | 97 ± 10 | 98 ± 6 | 0.67 ± 0.06 |
|  | 3 | 7.7 ± 1.1 | 45 ± 3 | 95 ± 4 | 80 ± 8 | 0.96 ± 0.03 |
|  | 8 | 9.8 ± 2.2 | 46 ± 2 | 99 ± 4 | 120 ± 19 | 0.88 ± 0.05 |
| Control II | Pre | 6.7 ± 0.4 | 37 ± 1 | 76 ± 2 | 69 ± 12 | 0.60 ± 0.09 |
|  | 3 | 11.2 ± 1.6 | 51 ± 2 | 101 ± 8 | 58 ± 5 | 0.80 ± 0.11 |
|  | 8 | 14.4 ± 2.1 | 57 ± 3 | 114 ± 7 | 74 ± 15 | 0.73 ± 0.04 |
| H4H1765N | Pre | 8.7 ± 0.2 | 39 ± 6 | 79 ± 8 | 94 ± 19 | 0.81 ± 0.12 |
|  | 3 | 8.0 ± 1.1 | 46 ± 6 | 91 ± 9 | 68 ± 7 | 0.72 ± 0.06 |
|  | 8 | 9.2 ± 1.6 | 46 ± 6 | 92 ± 8 | 75 ± 7 | 0.70 ± 0.05 |

Example 8

Effect of Combination Therapy with an Anti-GCGR Antibody and an Antibody Specific for PCSK9 (Proprotein Convertase Subtilisin/Kexin Type 9) on Blood Glucose, Plasma Lipid and Hepatic Triglyceride Levels in Mice Reagents The following antibodies were used to study the effect of combination therapy with an anti-GCGR antibody and an antibody specific for PCSK9 on blood glucose levels, plasma lipid levels and hepatic triglyceride levels in C57BL/6 mice: An anti-hIL4R antibody designated REGN496, which is an hIgG4 isotype control; an anti-GCGR (hIgG4) antibody designated H4H1327P; and an anti-PCSK9 (hIgG1) antibody designated H1H316P. The amino acid sequence identifiers for the HCVR, LCVR, HCDRs, and LCDRs are shown below in Table 9.

TABLE 9

| REGN AB Designation | SEQ ID NUMBERS | | | | | | | |
|---|---|---|---|---|---|---|---|---|
|  | HCVR | HCDR1 | HCDR2 | HCDR3 | LCVR | LCDR1 | LCDR2 | LCDR3 |
| REGN496 | 194 | 195 | 196 | 197 | 198 | 199 | 200 | 201 |
| H4H1327P | 86 | 72 | 74 | 76 | 88 | 80 | 82 | 84 |
| H1H316P | 173 | 161 | 163 | 165 | 175 | 167 | 169 | 171 |

Experimental Procedure

The combined effects of H4H1327P, an anti-hGCGR antibody, and H1H316P, an anti-hPCSK9 antibody, on blood glucose, plasma lipid, and hepatic triglyceride (TG) levels were determined in C57BL/6 mice.

H4H1327P cross-reacts with mouse GCGR, and H1H316P cross-reacts with mouse PCSK9. C57BL/6 mice were put into six groups of six animals. Each group received once a week subcutaneous injections of an antibody or a combination of two antibodies. The first group was injected at 10 mg/kg with a hIgG4 isotype control antibody, which does not bind to any known mouse protein. The second and third group received H4H1327P at 3 mg/kg and 10 mg/kg, respectively. The fourth group was injected with 10 mg/kg H1H316P. The fifth group received a combination of 3 mg/kg H4H1327P and 10 mg/kg H1H316P, and the sixth group was injected with a combination of 10 mg/kg H4H1327P and 10 mg/kg H1H316P. Eleven and 19 days after the initial antibody dosing, mice were bled for blood glucose and plasma lipid measurements. At Day 19, liver was harvested for the determination of hepatic TG content. Blood glucose levels were measured with the use of ACCU-CHEK® Compact Plus (Roche). The percent reduction in blood glucose from the mean blood glucose level of the isotype control group was calculated for each animal. The percent reduction and associated error in blood glucose for each treatment group was then calculated by averaging across values for the individual animals in each group. Results, expressed as (mean±SEM) of percent blood glucose reduction, are shown in Table 10a and in FIG. 1.

Figure 2:
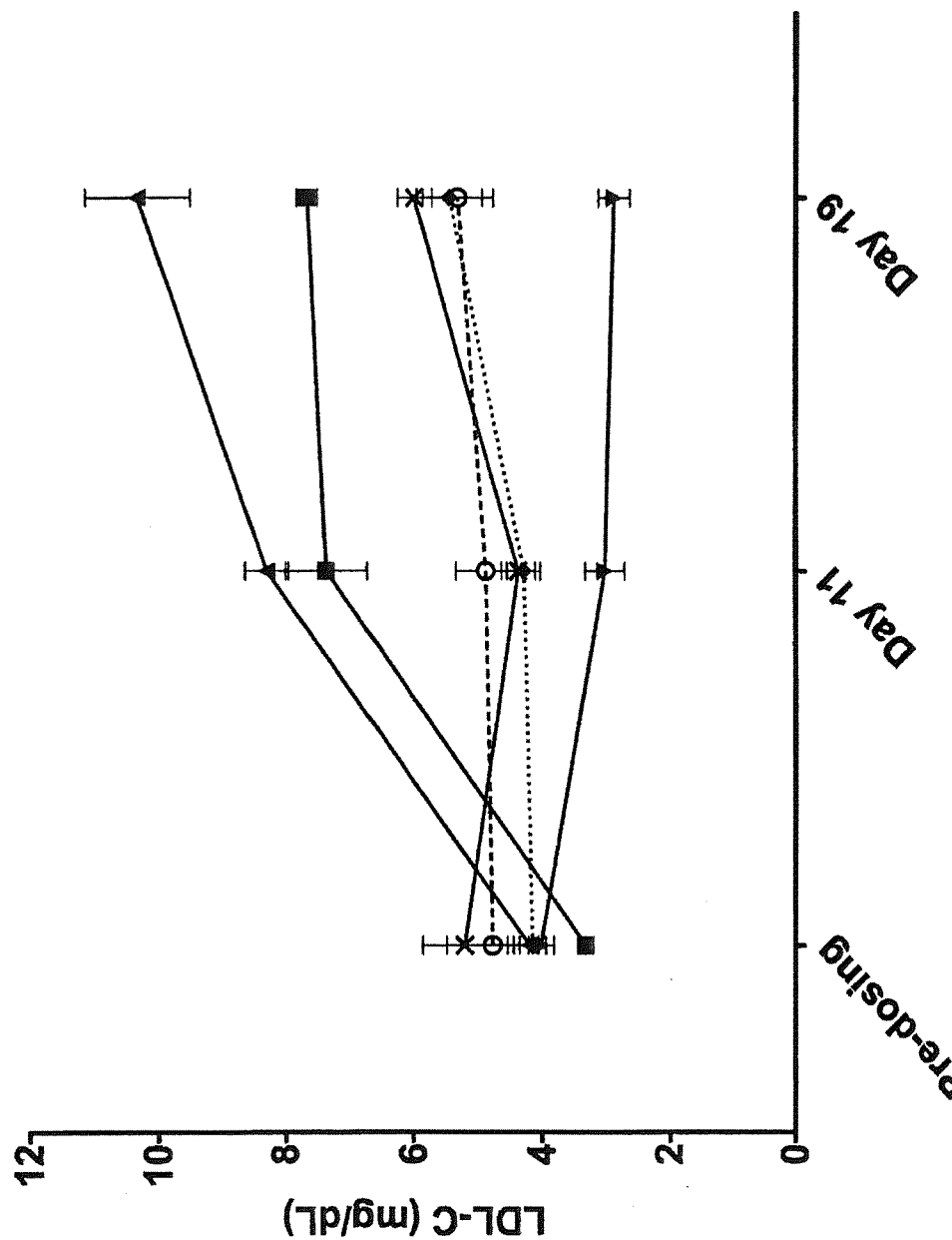
FIG. 2 shows plasma LDL-C levels in C57BL6 mice after administration of H4H1327P, and/or H1H316P when given alone or in combination. Control (X with solid line); H4H1327P at 3 mg/kg (■ with solid line); H4H1327P at 10 mg/kg (▲ with solid line); H1H316P at 10 mg/kg (◉ with solid line); H4H1327P at 3 mg/kg+H1H316P at 10 mg/kg (● with dashed line); H4H1327P at 10 mg/kg+H1H316P at 10 mg/kg (○ with dashed lines).
Figure 3:
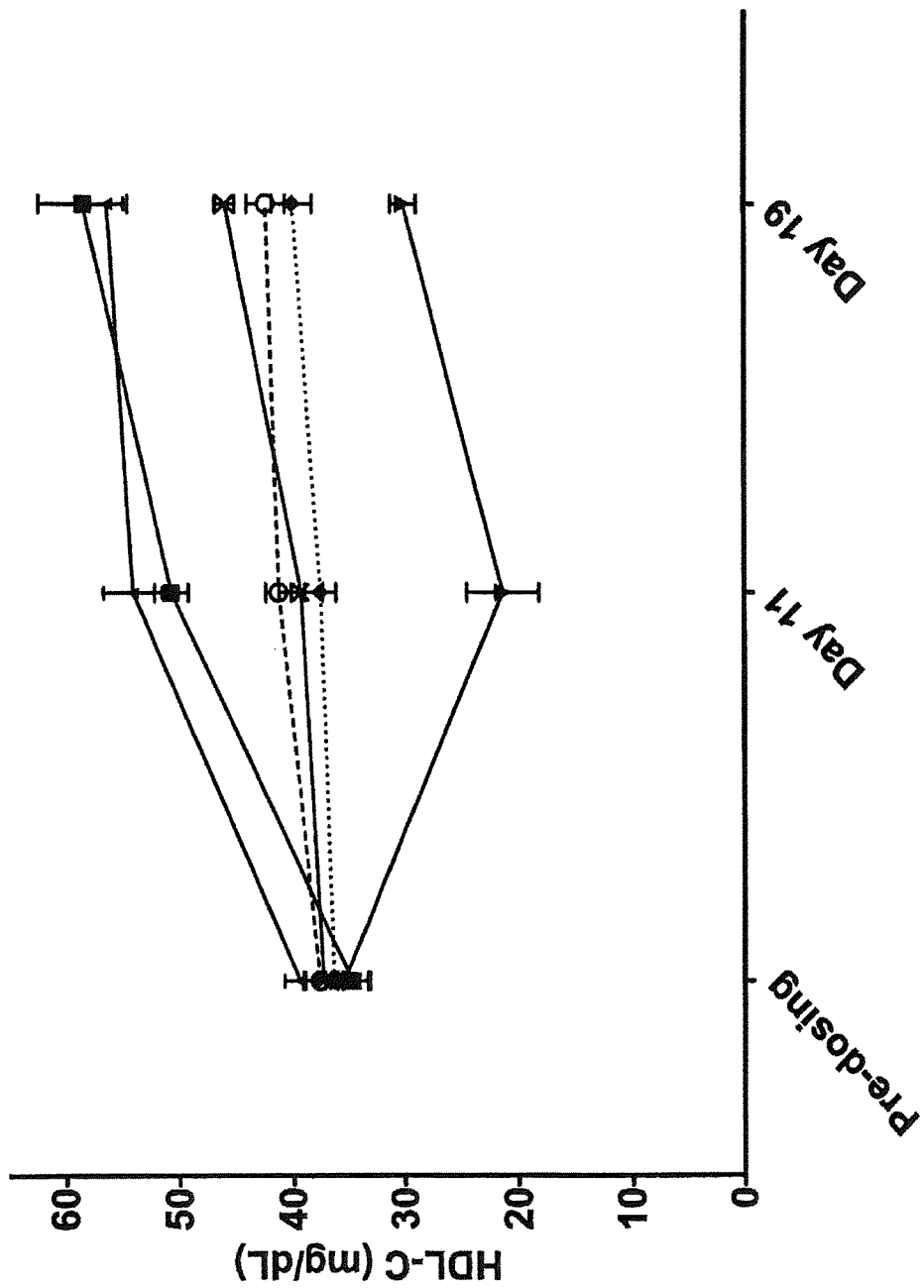
FIG. 3 shows plasma HDL-C levels in C57BL6 mice after administration of H4H1327P, and/or H1H316P when given alone or in combination. Control (X with solid line); H4H1327P at 3 mg/kg (■ with solid line); H4H1327P at 10 mg/kg (▲ with solid line); H1H316P at 10 mg/kg (◉ with solid line); H4H1327P at 3 mg/kg+H1H316P at 10 mg/kg (● with dashed line); H4H1327P at 10 mg/kg+H1H316P at 10 mg/kg (○ with dashed lines).
Figure 4:
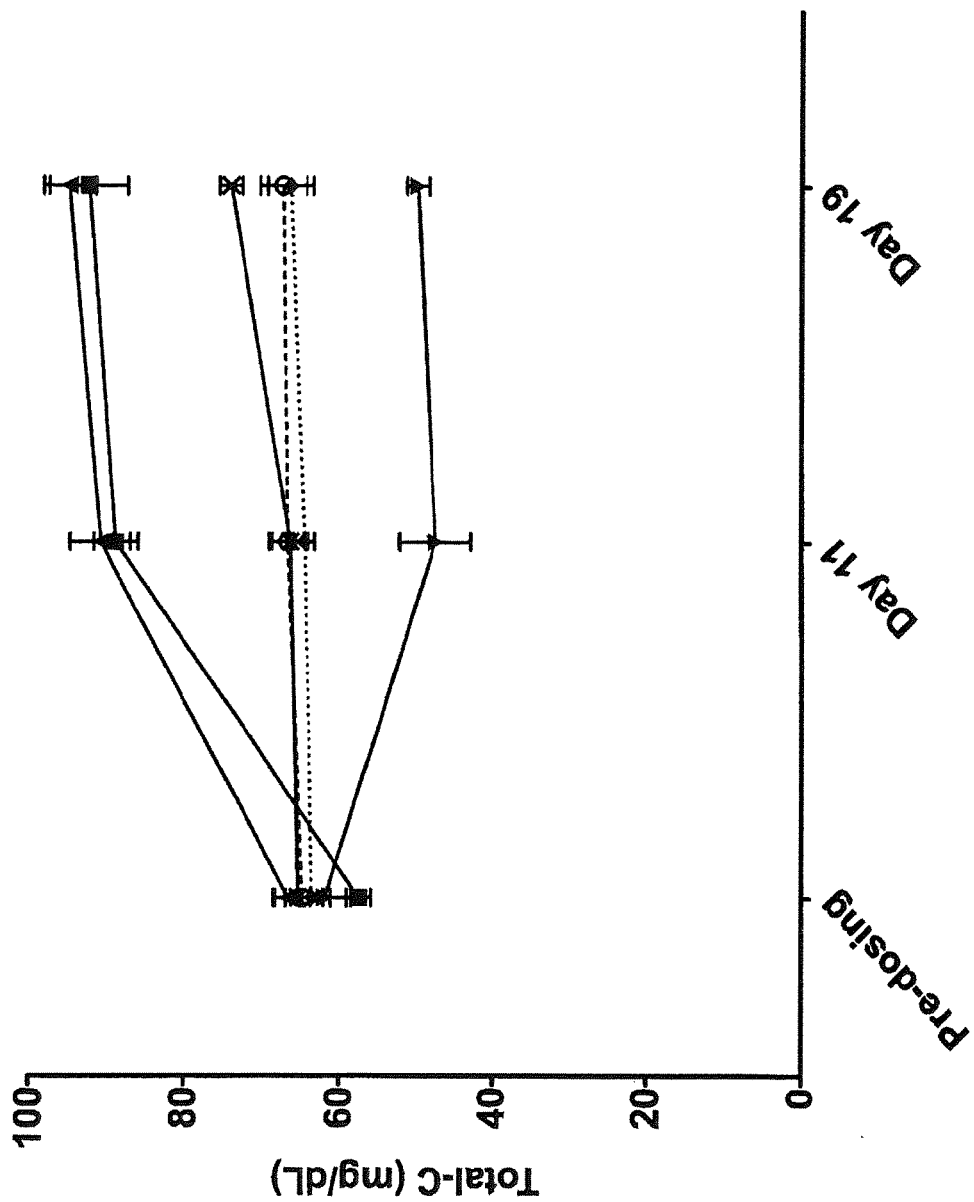
FIG. 4 shows total plasma cholesterol levels in C57BL6 mice after administration of H4H1327P, and/or H1H316P when given alone or in combination. Control (X with solid line); H4H1327P at 3 mg/kg (■ with solid line); H4H1327P at 10 mg/kg (▲ with solid line); H1H316P at 10 mg/kg (◉ with solid line); H4H1327P at 3 mg/kg+H1H316P at 10 mg/kg (● with dashed line); H4H1327P at 10 mg/kg+ H1H316P at 10 mg/kg (○ with dashed lines).
Figure 5:
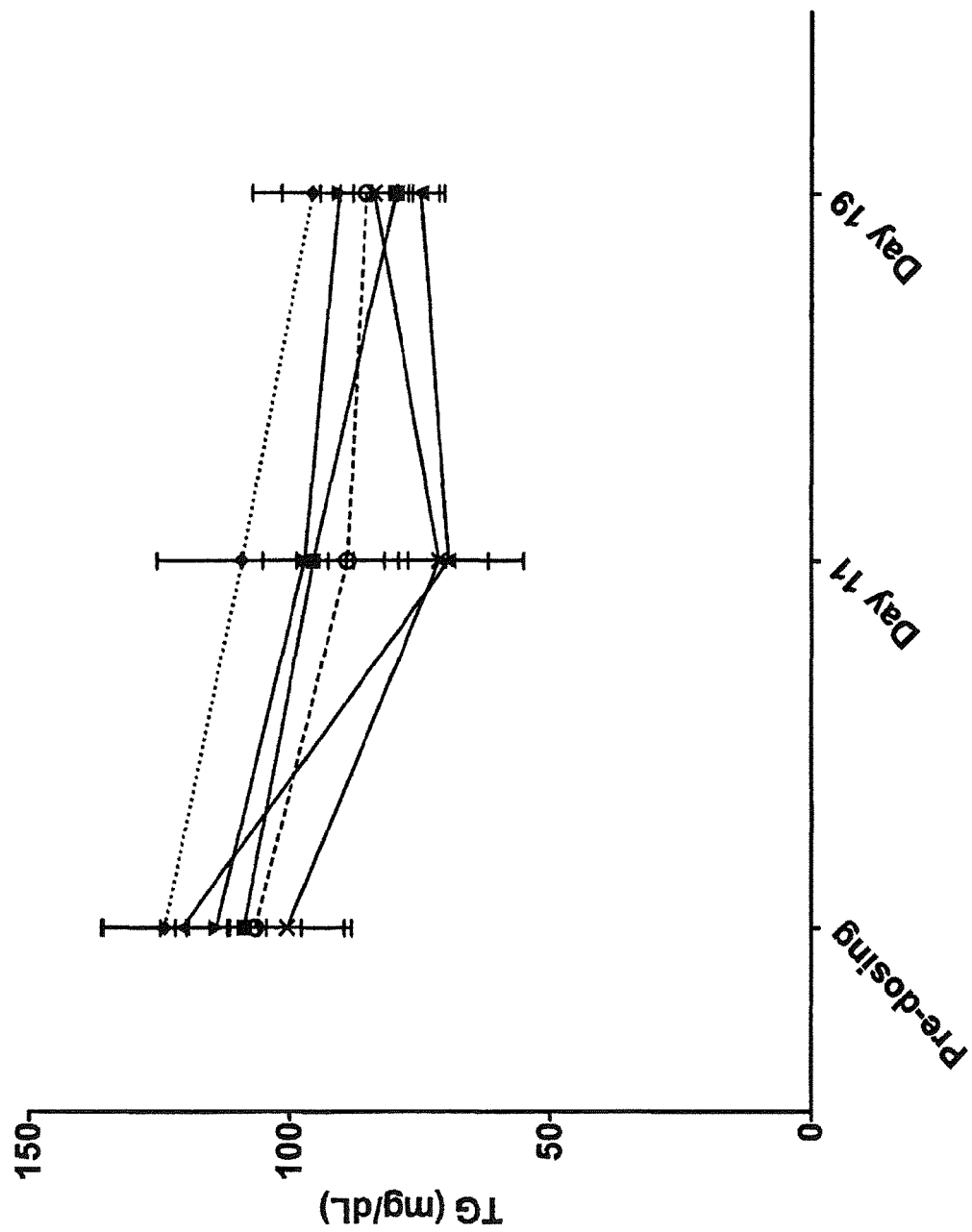
FIG. 5 shows plasma triglyceride levels in C57BL6 mice after administration of H4H1327P, and/or H1H316P when given alone or in combination. Control (X with solid line); H4H1327P at 3 mg/kg (■ with solid line); H4H1327P at 10 mg/kg (▲ with solid line); H1H316P at 10 mg/kg (⊙ with solid line); H4H1327P at 3 mg/kg+H1H316P at 10 mg/kg (◐ with dashed line); H4H1327P at 10 mg/kg+H1H316P at 10 mg/kg (○ with dashed lines).
Figure 6:
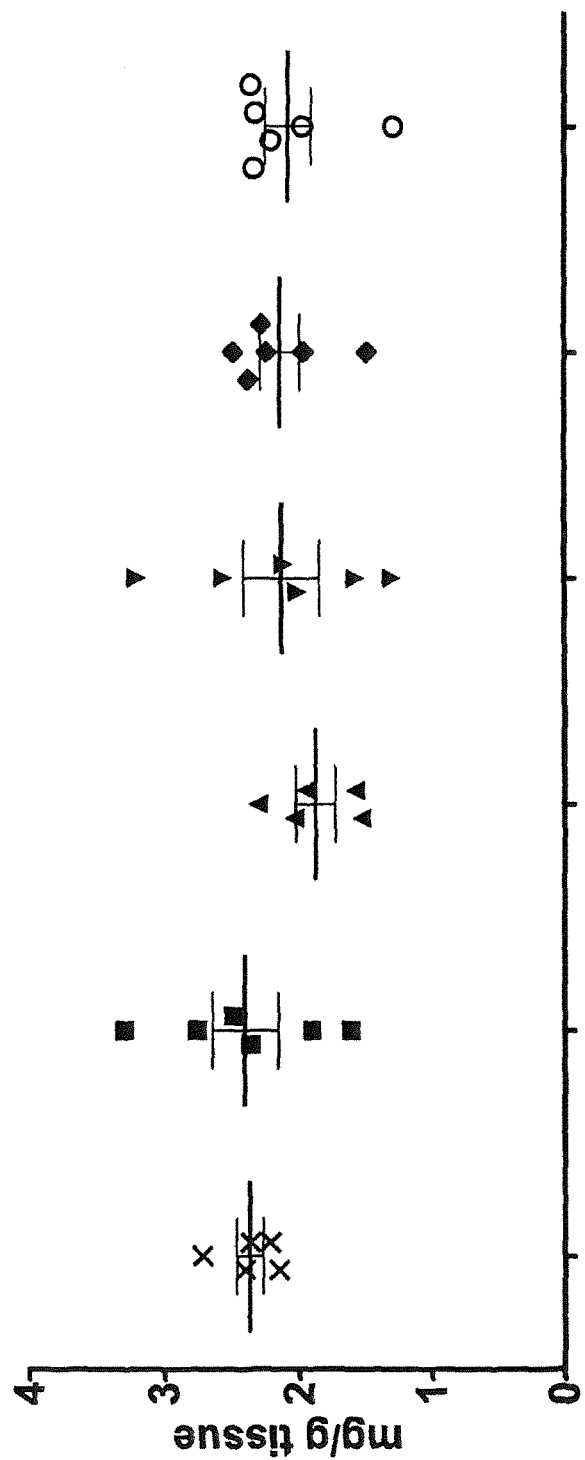
FIG. 6 shows hepatic triglyceride levels in C57BL6 mice after administration of H4H1327P, and/or H1H316P when given alone or in combination. Control (X); H4H1327P at 3 mg/kg (■); H4H1327P at 10 mg/kg (▲); H1H316P at 10 mg/kg (⊙); H4H1327P at 3 mg/kg+H1H316P at 10 mg/kg (◐); H4H1327P at 10 mg/kg+H1H316P at 10 mg/kg (○).

Plasma lipid levels were determined by ADVIA® 1650 Chemistry System (Siemens). Hepatic TG contents were measured using a colorimetric assay (Teco Diagnostics) after extraction of TG from tissue with chloroform/methanol. Means were calculated for each of the measurements of plasma low density lipoprotein cholesterol (LDL-C), high density lipoprotein cholesterol (HDL-C), total cholesterol (TOTAL-C), TG and hepatic TG levels for each group. Results, expressed as (mean±SEM) of plasma and hepatic lipid concentrations, are shown in Table 10b and in FIG. 2 (plasma LDL-C levels); FIG. 3 (Plasma HDL-C levels); FIG. 4 (Plasma Total-C levels); FIG. 5 (Plasma TG levels); and FIG. 6 (hepatic TG content).

TABLE 10a

| | Blood glucose reduction (%) | | | | |
|---|---|---|---|---|---|
| Time (days) | H4H1327P 3 mg/kg | H4H1327P 10 mg/kg | H1H316P 10 mg/kg | H4H1327P 3 mg/kg + H1H316P 10 mg/kg | H4H1327P 10 mg/kg + H1H316P 10 mg/kg |
| 11 | 33 ± 7 | 40 ± 5 | 3 ± 3 | 28 ± 7 | 39 ± 2 |
| 19 | 25 ± 4 | 28 ± 4 | −4 ± 6 | 21 ± 7 | 27 ± 2 |

TABLE 10b

| Antibody | Time (days) | Plasma | | | | Liver TG |
| | | LDL-C (mg/dL) | HDL-C (mg/dL) | TOTAL-C (mg/dL) | TG (mg/dL) | (mg/g tissue) |
| --- | --- | --- | --- | --- | --- | --- |
| Control | Pre-dosing | 5.2 ± 0.7 | 37 ± 2 | 65 ± 2 | 101 ± 11 | NA |
| | 11 | 4.4 ± 0.3 | 39 ± 2 | 66 ± 2 | 72 ± 16 | NA |
| | 19 | 6.0 ± 0.3 | 46 ± 1 | 74 ± 1 | 84 ± 6 | 2.4 ± 0.1 |
| H4H1327P 3 mg/kg | Pre-dosing | 3.3 ± 0.1 | 35 ± 1 | 58 ± 2 | 109 ± 11 | NA |
| | 11 | 7.4 ± 0.6 | 51 ± 2 | 89 ± 3 | 96 ± 14 | NA |
| | 19 | 7.7 ± 0.2 | 59 ± 4 | 93 ± 5 | 80 ± 8 | 2.4 ± 0.2 |
| H4H1327P 10 mg/kg | Pre-dosing | 4.2 ± 0.2 | 39 ± 1 | 67 ± 2 | 120 ± 16 | NA |
| | 11 | 8.3 ± 0.3 | 54 ± 3 | 91 ± 4 | 70 ± 8 | NA |
| | 19 | 10.4 ± 0.8 | 56 ± 1 | 95 ± 3 | 75 ± 5 | 1.9 ± 0.1 |
| H1H316P 10 mg/kg | Pre-dosing | 4.0 ± 0.2 | 35 ± 2 | 62 ± 3 | 114 ± 8 | NA |
| | 11 | 3.0 ± 0.3 | 21 ± 3 | 48 ± 5 | 97 ± 8 | NA |
| | 19 | 2.9 ± 0.2 | 30 ± 1 | 50 ± 1 | 91 ± 11 | 2.1 ± 0.3 |
| H4H1327P 10 mg/kg + H1H316P 10 mg/kg | Pre-dosing | 4.2 ± 0.2 | 36 ± 1 | 64 ± 1 | 124 ± 12 | NA |
| | 11 | 4.3 ± 0.3 | 38 ± 1 | 65 ± 1 | 109 ± 16 | NA |
| | 19 | 5.4 ± 0.5 | 40 ± 2 | 66 ± 3 | 96 ± 11 | 2.1 ± 0.1 |
| H4H1327P 3 mg/kg + H1H316P 10 mg/kg | Pre-dosing | 4.8 ± 0.7 | 38 ± 2 | 65 ± 4 | 107 ± 18 | NA |
| | 11 | 4.9 ± 0.5 | 41 ± 1 | 67 ± 2 | 89 ± 10 | NA |
| | 19 | 5.3 ± 0.6 | 42 ± 2 | 67 ± 3 | 85 ± 9 | 2.1 ± 0.2 |

NA: Not applicable

Tabulated Data Summary:

Mice treated with H4H1327P alone showed significant reductions in blood glucose levels and increases in LDL, HDL, and total cholesterol levels in comparison to mice receiving control mAb. Mice treated with H1H316P alone exhibited significant reductions in cholesterol levels with no change in blood glucose levels. Mice treated with a combination of H4H1327P and H1H316P showed significant reductions in blood glucose levels with no alterations in cholesterol levels in comparison to mice receiving control mAb. Hepatic TG contents were not altered in any of the treatment groups compared to the isotype control group.

Example 9

The Effect of an Anti-GCGR Antibody in a Diet-Induced Obesity Mouse Model

The effects of H4H1327P, an anti-hGCGR antibody that cross-reacts with mouse GCGR, on blood glucose levels and body weights were determined in a diet-induced obesity (DIO) mouse model of type 2 diabetes (T2D).

The DIO model is developed by feeding mice on a high fat (60% kcal) diet (HFD) from 5-6 weeks of age. After approximately 6 weeks on the diet, mice develop metabolic abnormalities including insulin resistance, glucose intolerance, and obesity. The DIO model induces a physiological condition in mice closer to human T2D than that induced by the other two commonly used T2D models, ob/ob and db/db mice, since the latter two models result from mutations in leptin or leptin receptor genes, respectively, which are rarely the cause of T2D in humans.

In this study, eleven week-old male C57Bl/6 mice, placed on HFD since 5 weeks of age, were purchased from Taconic farms, Inc. and kept on the diet for another 8 weeks. The mice were divided into 4 groups of 10 animals per group at 19 weeks of age. Each group received weekly (on days 0, 7, 14, and 21) subcutaneous injections of H4H1327P at 3, 10, or 30 mg/kg, or 30 mg/kg of the hIgG4 isotype control, which does not bind to any known mouse protein. Blood glucose levels and body weights were measured periodically, and 6 days after administering the last antibody dose (on day 27), 6 mice/group were sacrificed. For the next 6 weeks, blood glucose and body weights were monitored for the remaining 4 mice/group. The percent reduction in blood glucose levels compared to the mean blood glucose level of the isotype control group was calculated for each animal. The percent reduction and associated error in blood glucose for each treatment group was then calculated by averaging across values for the individual animals in each group. Results, expressed as (mean±SEM) of percent blood glucose reduction, are shown in Table 11. The percent change in body weight from the baseline (weight at day 0) was calculated for each animal. The percent change and associated error in body weight for each treatment group was then calculated by averaging across values for the individual animals in each group. Results, expressed as (mean±SEM) of percent body weight change from baseline, are shown in Table 12.

Results Summary and Conclusions:

H4H1327P, at all dosages tested, reduced blood glucose and body weight of DIO mice compared to the isotype control groups. The greatest relative blood glucose reduction (48.5%) occurred in the highest dose (30 mg/kg) group at day 10, and the greatest relative body weight reduction (12.8%) occurred in the highest dose group at day 28. The lowest dose (3 mg/kg) groups achieved mean relative blood glucose lowering and mean body weight lowering values of at least 70% the values exhibited by the highest dose groups through day 28 (one week following the last dose). The observed blood glucose and body weight lowering effects following the last treatment on day 21 (i.e., on days 28, 47, and 68) persisted longer for the higher H4H1327P dose groups compared to the lower dose groups.

TABLE 11

| | Blood glucose reduction (%) | | |
| Time (days) | H4H1327P 3 mg/kg | H4H1327P 10 mg/kg | H4H1327P 30 mg/kg |
| --- | --- | --- | --- |
| 10 | 44.6 ± 2.8 | 44.4 ± 1.8 | 48.5 ± 1.5 |
| 19 | 33.9 ± 2.3 | 39.0 ± 1.9 | 37.5 ± 2.5 |
| 28 | 24.8 ± 1.7 | 28.1 ± 2.8 | 32.4 ± 1.6 |

TABLE 11-continued

| | Blood glucose reduction (%) | | |
|---|---|---|---|
| Time (days) | H4H1327P 3 mg/kg | H4H1327P 10 mg/kg | H4H1327P 30 mg/kg |
| 47 | −3.9 ± 7.1 | 21.2 ± 7.0 | 30.0 ± 2.4 |
| 68 | −4.3 ± 7.9 | −1.1 ± 5.8 | −12.9 ± 12.1 |

TABLE 12

| | Body weight change from baseline (%) | | | |
|---|---|---|---|---|
| Time (days) | Isotype control 30 mg/kg | H4H1327P 3 mg/kg | H4H1327P 10 mg/kg | H4H1327P 30 mg/kg |
| 10 | 1.8 ± 0.6 | −5.5 ± 0.6 | −6.1 ± 0.6 | −5.8 ± 0.6 |
| 19 | 2.2 ± 0.6 | −7.3 ± 0.6 | −9.6 ± 0.6 | −10.3 ± 0.7 |
| 28 | 1.8 ± 0.4 | −9.2 ± 1.2 | −10.5 ± 0.5 | −12.8 ± 1.0 |
| 47 | 6.6 ± 0.8 | 5.2 ± 1.3 | 2.5 ± 1.4 | −3.7 ± 2.2 |
| 68 | 10.4 ± 1.1 | 9.7 ± 0.7 | 10.6 ± 1.0 | 8.2 ± 1.1 |

Example 10

The Effect of an Anti-GCGR Antibody in a Streptozotocin (STZ)-Induced Mouse Model of Diabetic Ketoacidosis The effects of H4H1327P, an anti-hGCGR antibody, which cross-reacts with mouse GCGR, on plasma ketone and glucose levels were determined in a streptozotocin (STZ)-induced mouse model of diabetic ketoacidosis (DKA). STZ is a chemical toxic to pancreatic beta cells of mammals which, therefore, destroys this cell type when administered to rodents. A single, high dose (200 mg/kg) injection of STZ to C57B1/6 mice leads to the development of severe hyperglycemia and ketonuria, conditions exhibited in human DKA, in 3 days. Nine-week-old male C57B1/6 mice, purchased from Taconic farms, Inc. were divided into 2 groups of 10 animals, and each group received either intraperitoneal injections of STZ (in citrate buffer) at 200 mg/kg or vehicle (also in citrate buffer). Three days later, severe hyperglycemia (blood glucose levels >400 mg/dL) and ketonuria were confirmed in all STZ treated animals. The next morning, the STZ treated mice were divided into 2 groups of 5 animals, and each group received an intravenous injection of H4H1327P or hIgG4 isotype control at 10 mg/kg. The citrate buffer treated mice were also divided into 2 groups of 5 animals, and each group received intravenous injection of H4H1327P or hIgG4 isotype control at 10 mg/kg. Mice were bled 18 hours before antibody dosing (2.5 days after the STZ administration) and 28 hours after antibody dosing under isoflurane anesthesia for plasma collection. Plasma ketone levels were determined by beta-hydroxybutyrate assay (Biovision), and plasma glucose levels by ADVIA® 1650 Chemistry System (Siemens). Averages were calculated for the measurements of beta-hydroxybutyrate and glucose levels for each of the four groups. Results, expressed as (mean±SEM) of plasma beta-hydroxybutyrate and glucose concentrations, are shown in Table 13.

Results Summary and Conclusions:

A reduction (average 67%) in plasma beta-hydroxybutyrate (ketone) concentration was observed in STZ-induced diabetic ketoacidotic mice 28 hours after H4H1327P treatment in comparison to plasma levels 18 hours prior to the treatment, demonstrating that H4H1327P effectively lowered plasma ketone levels in a mouse model of DKA. For the STZ-treated mice dosed with isotype control antibody, a 14% average increase in blood glucose was observed for the serum samples collected 28 hours after control antibody treatment compared to the samples collected 18 hours before antibody treatment, whereas for the H4H1327P dosed mice in the STZ-treated group less than 1% average change in glucose was observed between serum samples collected at these two time points.

TABLE 13

| | Time from antibody treatment (hrs) | Vehicle/ Isotype control | Vehicle/ H4H1327P | STZ/ Isotype control | STZ/ H4H1327P |
|---|---|---|---|---|---|
| Beta-hydroxybutyrate (mM) | −18 | 1.1 ± 0.6 | 0.6 ± 0.2 | 3.4 ± 0.7 | 3.6 ± 0.2 |
| | 28 | 0.4 ± 0.0 | 0.8 ± 0.4 | 2.4 ± 0.6 | 1.2 ± 0.1 |
| Glucose (mg/dL) | −18 | 214 ± 24 | 250 ± 6 | 610 ± 39 | 601 ± 26 |
| | 28 | 238 ± 16 | 152 ± 5 | 696 ± 66 | 606 ± 59 |

Example 11

Generation of a Bi-Specific Antibody

Various bi-specific antibodies are generated for use in practicing the methods of the invention. For example, GCGR-specific antibodies are generated in a bi-specific format (a "bi-specific") in which variable regions binding to distinct ectodomain and/or EC loop epitopes on GCGR are linked together to confer dual-loop specificity within a single binding molecule. Appropriately designed bi-specifics may enhance overall glucagon receptor blocking efficacy through increasing both GCGR specificity and binding avidity. Variable regions with specificity for individual ectodomain epitopes (e.g., segments of the N-terminal domain, or of the EC1, EC2, or EC3 GCGR loops) or that can bind to different regions within one ectodomain segment or loop are paired on a structural scaffold that allows each variable region to bind simultaneously to the separate epitopes, or to different regions within one ectodomain or EC loop. In one example for a bi-specific, heavy chain variable regions (VH) from a binder with one ectodomain or loop specificity are recombined with light chain variable regions (VL) from a series of binders with a second ectodomain or EC loop specificity to identify non-cognate VL partners that can be paired with an original VH without disrupting the original specificity for that VH. In this way, a single VL segment (e.g., VL1) can be combined with two different VH domains (e.g., VH1 and VH2) to generate a bi-specific comprised of two binding "arms" (VH1-VL1 and VH2-VL1). Use of a single VL segment reduces the complexity of the system and thereby simplifies and increases efficiency in cloning, expression, and purification processes used to generate the bi-specific (See, for example, US2011/0195454 U.S. Ser. No. 13/022,759 and US2010/0331527, now U.S. Pat. No. 8,586,713).

Alternatively, antibodies that bind both GCGR and a second target, such as, but not limited to, for example, human proprotein convertase subtilisin/kexin type 9 (hPCSK9), may be prepared in a bi-specific format using techniques described herein, or other techniques known to those skilled in the art. Antibody variable regions binding to distinct GCGR regions that are extracellularly exposed are linked together with variable regions that bind to relevant sites on, for example, PCSK9, to confer dual-antigen specificity within a single binding molecule. Appropriately designed bi-specifics of this nature serve a dual function. For example, in the case of a bi-specific antibody that binds both GCGR and PCSK9, one may be able to lower blood glucose by virtue of one arm of the bi-specific antibody binding GCGR, while at the same time lowering plasma lipids, by virtue of the second arm of the antibody binding PCSK9. Variable regions with specificity for individual ectodomain epitopes of GCGR, are combined with a variable region with specificity for PCSK9 and are paired on a structural scaffold that allows each variable region to bind to the separate antigens.

The bi-specific binders are tested for binding and functional blocking of the target antigens, for example, GCGR and/or PCSK9, in any of the assays described above for antibodies. For example, standard methods to measure soluble protein binding are used to assess the bispecific-PCSK9 interaction, such as Biacore, ELISA, size exclusion chromatography, multi-angle laser light scattering, direct scanning calorimetry, and other methods. Binding of bi-specific antibodies to cells expressing GCGR is determined through flow cytometry using a fluorescently labeled secondary antibody recognizing either or both of the two target antigens bound to cells. Cross-reactivity to the different GCGR ectodomains or loops within and between different species variants is assessed using an ELISA binding assay in which synthetic peptides representing the different ectodomains or loops are coated onto the wells of microtiter plates, and binding of a bi-specific is determined through use of a secondary detection antibody. Binding experiments with loop peptides can also be conducted using surface plasmon resonance experiments, in which real-time binding interaction of peptide to antibody is measured by flowing a peptide or bi-specific across a sensor surface on which bi-specific or peptide, respectively, is captured. Functional in vitro blocking of the GCGR receptor by a bi-specific is determined using any bioassay such as that described herein, or by in vivo determination of blood glucose levels in appropriate animal models, such as those described herein. Functional in vitro blocking of PCSK9 by a bi-specific is determined using any bioassay such as that described in WO2010/077854, or in US2010/0166768, now U.S. Pat. No. 8,062,640, or by in vivo determination of plasma lipid levels in appropriate animal models, such as those described herein.

Example 12

The Effect of an Anti-GCGR Antibody in a Ketamine/Xylazine-Induced Mouse Model of Short Term Stress Hyperglycemia The effects of H4H1327P anti-GCGR antibody on blood glucose levels were determined in an anesthesia (ketamine/xylazine)-induced mouse model of stress hyperglycemia. The combination of ketamine and xylazine is a commonly used anesthesia for many species including rodents. Ketamine is a dissociative anesthetic, and xylazine is a powerful sedative/analgesic. Ketamine/xylazine anesthesia has been shown to induce stress hormone release and elevate blood glucose levels temporarily (Saha J K et al., *Experimental Biology and Medicine* 2005, 230:777-784). Baseline blood glucose levels were measured in seven 2-month-old male C57BL6 mice, and the mice received intramuscular injection of a combination of ketamine (120 mg/kg) and xylazine (5 mg/kg). All mice became unconscious within 5 minutes of ketamine/xylazine injection. Based on the blood glucose levels measured earlier, mice were divided into 2 groups of n=3 or n=4. Thirty minutes after ketamine/xylazine administration, while mice were still unconscious, each group received intravenous injections of the anti-GCGR antibody designated H4H1327P (n=4) or the hIgG isotype control antibody designated H1H316P (n=3) at 10 mg/kg. 45-60 minutes after ketamine/xylazine administration, all mice regained consciousness. Mice were bled retroorbitally 0.5, 1.5, 3, 4.5, 6 and 24 hours after ketamine/xylazine administration (=immediately before and 1, 2.5, 4, 5.5, and 23.5 hours after mAb injections) for blood glucose measurements. Mean±SEM of blood glucose levels at each time point are calculated for each group and shown in Table 14.

Tabulated Data Summary:

TABLE 14

| | Time (hrs) | Isotype control | Anti-GCGR Ab H4H1327P |
|---|---|---|---|
| Blood Glucose (mg/dL) | 0 | 197 ± 6 | 200 ± 6 |
| | 0.5 | 247 ± 27 | 244 ± 10 |
| | 1.5 | 432 ± 23 | 184 ± 6 |
| | 3 | 502 ± 18 | 267 ± 19 |
| | 4.5 | 478 ± 36 | 273 ± 53 |
| | 6 | 330 ± 54 | 230 ± 52 |
| | 24 | 172 ± 2 | 118 ± 8 |

Figure 7:
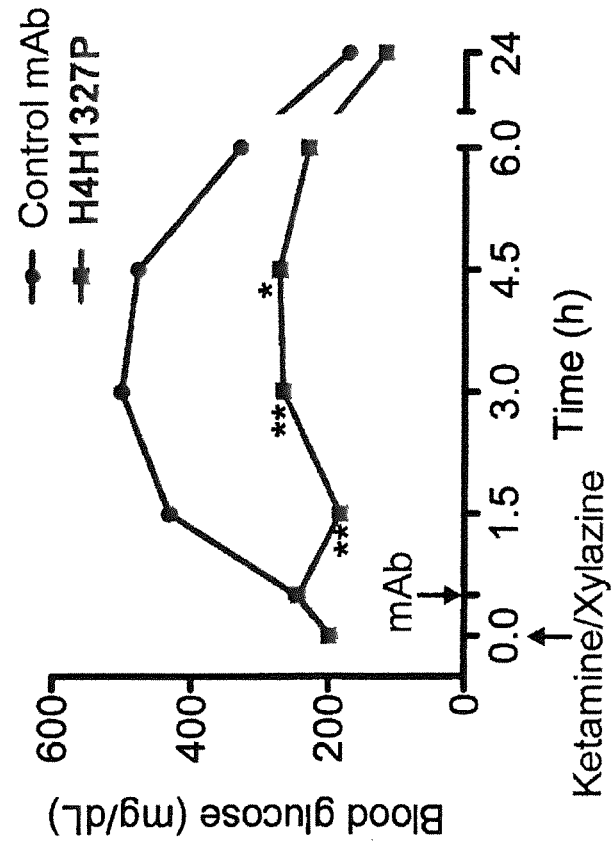
FIG. 7 shows the blood glucose levels in a C57BL6 mouse model of stress hyperglycemia (see Saha, J K, Exptl. Biol. & Med. (2005), 230:777-784) after administration of a control antibody or an anti-GCGR antibody. Briefly, groups of C57BL6 mice received an intramuscular injection of a combination of ketamine (120 mg/kg) and xylazine (5 mg/kg). Thirty minutes later, each group received intravenous injections of either an isotype control antibody (●), or an anti-GCGR antibody designated H4H1327P (■), each at a concentration of 10 mg/kg. Blood glucose was measured at 0.5, 1.5, 3, 4.5, 6 and 24 hours after ketamine/xylazine administration.

Results Summary and Conclusions:

A ketamine/xylazine-induced increase in blood glucose levels was observed in mice treated with control mAb between 1.5 and 6 hours after ketamine/xylazine administration. In contrast, mice treated with the anti-GCGR antibody, H4H1327P, showed minimum changes in blood glucose levels. These data suggest that H4H1327P, within 1 hour of administration, blocks ketamine/xylazine-induced hyperglycemia. The results are also depicted in FIG. 7.

Example 13

The Effects an Anti-GCGR Antibody in Combination with Humulin on Blood Glucose in Ketamine/Xylazine-Treated Mice Using the stress hyperglycemia animal model described above, a study was conducted to determine the effect of therapy with insulin and the anti-GCGR antibody H4H1327P alone, or combined together, on blood glucose levels.

In this study a total of 23 mice were divided into 6 groups. All mice received an IM injection of a combination of ketamine (120 mg/kg) and xylazine (5 mg/kg). All mice became unconscious within 5 minutes of ketamine/xylazine injection and regained consciousness 45-60 minutes after ketamine/xylazine administration. Thirty minutes after ketamine/xylazine administration, Groups 1 (n=3), 2 (n=4), 3 (n=4), and 4 (n=4) received an IV injection (via the tail) of the hIgG isotype (negative control) antibody, REGN496, (n=3) at 5 mg/kg, and Groups 5 (n=4) and 6 (n=4) received an IV injection (via the tail) of ant-GCGR antibody, H4H1327P at 5 mg/kg. One hour after ketamine/xylazine administration, Groups 2, 3, 4, and 6 received an SC injection of Humulin R (Lilly) at 0.1, 0.033, 0.01, and 0.01 U/kg, respectively, at a volume of 5 µL per gram of body weight. Groups 1 and 5 received an SC injection of water at 5 µL per gram of body weight. Water was used to dilute the insulin and serves as a vehicle control. Nonfasted blood glucose was measured using an ACCU-CHEK® Compact Plus glucometer (Roche) at 0, 1.5, 3, 4.5, 6, 7.5 and 24 h post-ketamine/xylazine administration. Mice were sorted into antibody treatment groups based on their baseline glucose reading so that the mean glucose level across treatment groups was approximately equal. The 6 treatment groups are summarized in Table 15.

TABLE 15

Treatment group details for H4H1327P and Humulin combination study

| Treatment group # | Anesthesia (Time 0) | Antibody treatment IV (5 mg/kg) (30 minutes post-anesthesia) | Humulin SC (U/kg) (60 minutes post-anesthesia) |
|---|---|---|---|
| 1 | Ketamine/xylazine | REGN496 (control) | Water |
| 2 | Ketamine/xylazine | REGN496 (control) | 0.1 |
| 3 | Ketamine/xylazine | REGN496 (control) | 0.033 |
| 4 | Ketamine/xylazine | REGN496 (control) | 0.01 |
| 5 | Ketamine/xylazine | H4H1327P | Water |
| 6 | Ketamine/xylazine | H4H1327P | 0.01 |

Data Analyses

For blood glucose data, treatment group values are plotted as mean±standard error of the mean (SEM). Statistical analyses were performed utilizing GraphPad software Prism 5.0 (Macintosh Version). Blood glucose data were initially analyzed by two-way analysis of variance (ANOVA); a threshold of $p<0.05$ was considered statistically significant. After a significant F ratio was obtained with two-way ANOVA, post hoc analysis was conducted between groups with Bonferroni post-tests.

Results

Figure 8:
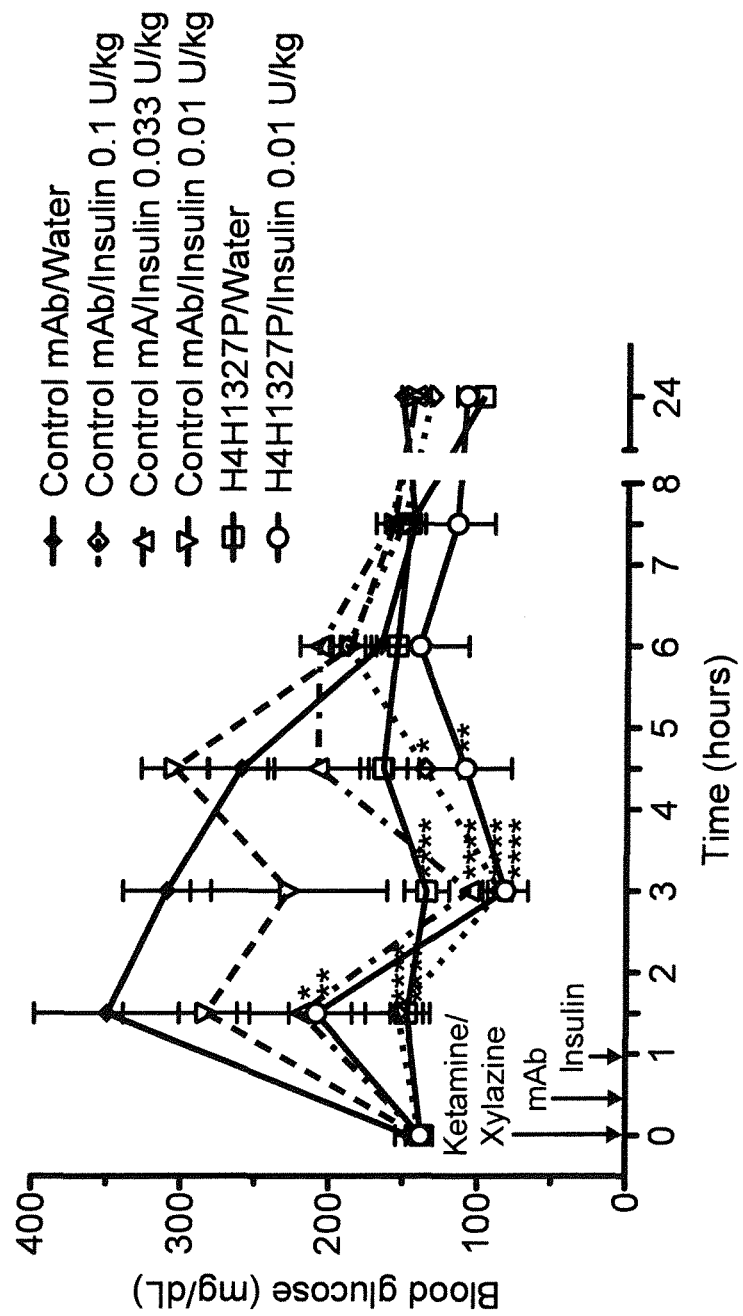
FIG. 8 shows the effect of H4H1327P on glucose lowering when used alone or in combination with insulin in a model of stress hyperglycemia. (●) Isotype negative control antibody in water; (◇) Isotype negative control antibody plus insulin at 0.1 U/kg; (Δ) Isotype negative control antibody plus insulin at 0.033 U/kg; (∇) Isotype negative control antibody plus insulin at 0.01 U/kg; (□) H4H1327P in water; (○) H4H1327P plus insulin at 0.01 U/kg.

Baseline glucose levels in mice before ketamine/xylazine injection were approximately 140 mg/dL (FIG. 8, 0 hr). In mice treated with control antibody and water, blood glucose levels increased more than 2-fold at 90 minutes post-ketamine/xylazine injection and then steadily declined, returning to baseline levels by 6 h post-ketamine/xylazine injection. In contrast, mice treated with 5 mg/kg H4H1327P and water (H4H1327P monotherapy) showed no hyperglycemic response to ketamine/xylazine injection and blood glucose levels remained stable throughout the study (See FIG. 8).

Mice treated with control antibody and insulin, showed a dose-dependent reduction in blood glucose levels compared with mice treated with control antibody and water. The lowest dose of insulin (0.01 U/kg) caused a trend toward reduced blood glucose levels at 90 minutes and 3 hr post-ketamine/xylazine injection, but this was not statistically significant compared with mice treated with control antibody and water. The 2 higher insulin dose groups (0.033 and 0.1 U/kg) caused significant reductions in blood glucose at 90 minutes, 3 hr and 4.5 hr (0.1 U/kg only) post-ketamine/xylazine injection compared with mice treated with control antibody and water. However, both 0.033 and 0.1 U/kg doses of insulin caused blood glucose levels to fall below baseline glucose levels at 3 h post-ketamine/xylazine injection.

The anti-GCGR antibody H4H1327P was tested in combination with the lowest dose of insulin (0.01 U/kg), which by itself did not significantly affect blood glucose levels. The combination of 5 mg/kg H4H1327P and 0.01 U/kg insulin significantly decreased blood glucose levels at 90 minutes, 3 hr and 4.5 hr post-ketamine/xylazine injection, compared with mice treated with control antibody and water. However, in contrast to H4H1327P monotherapy, blood glucose levels fell below baseline levels at 3 hr and 4.5 hr.

SUMMARY

In agreement with the findings of Saha et al., (Saha et al., (2005), Experimental Biology and Medicine 230 (10):777-84) in rats, the anesthetic combination of ketamine/xylazine induced a marked hyperglycemic response in mice that lasted for up to 6 hours. A single dose of 5 or 10 mg/kg of the anti-GCGR antibody H4H1327P prevented the hyperglycemic response to ketamine/xylazine anesthesia with a rapid onset of action; a significant reduction in blood glucose was observed within 1 hour and was sustained for up to 4 hours post-H4H1327P administration. Further, H4H1327P monotherapy effectively reduced and stabilized blood glucose in this model without causing glucose to fall below baseline values. In contrast, insulin monotherapy (at 0.033 U/kg or 0.1 U/kg) or H4H1327P and insulin combination therapy were both able to reduce blood glucose but caused glucose levels to fall below baseline values.

To summarize, the study presented here demonstrated a beneficial effect of combined treatment of insulin plus the anti-GCGR antibody of the invention, H4H1327P. In contrast to treatment with insulin alone (which may result in a possible hypoglycemic response, which could result in an increase in morbidity or mortality), the use of the anti-GCGR antibody, H4H1327P in conjunction with insulin has an insulin sparing effect in this animal model of stress hyperglycemia. Based on these findings, it may be possible to lower the dose of insulin needed (or shorten the duration of use) if therapy is combined with the anti-GCGR antibody of the invention, H4H1327P. Furthermore, treatment with H4H1327P monotherapy prevents ketamine/xylazine-induced hyperglycemia without causing hypoglycemia. Accordingly, these findings support the use of H4H1327P as stand alone therapy, or for use as adjunct therapy with insulin in perioperative stress hyperglycemia.

Example 14

Single Dosing of H4H1327P in Cynomolgus Monkeys with Spontaneous Diabetes

A study was done to determine the effect of a single dose of mAb H4H1327P, at two dose levels, on glucose under fasting, fed, and oral and IV glucose challenge conditions in cynomolgus monkeys with spontaneous diabetes. In addition, a second objective of this study was to estimate the onset and duration of a glucose lowering effect in order to assess the feasibility of pursuing the use of the antibodies for short-term indications, where glucose lowering in the first hours after administration is desired. Safety endpoints (lipids, liver enzymes, and pancreatic enzymes) and PK were also evaluated.

Figure 9:
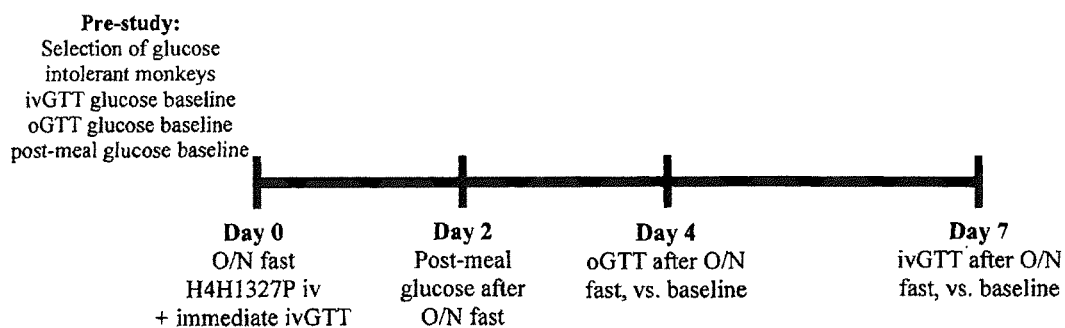
FIG. 9 shows an outline of a pharmacology study in diabetic cynomolgus monkeys using H4H1327P mAb.

Twenty-six cynomolgus monkeys (12 males and 14 females, ages between 11 and 21-years-old, body weights between 4.7 and 14.9 kg) with a history of diabetes and/or pre-diabetes were first screened for the presence of mild fasting hyperglycemia (blood glucose>90 mg/dL), and 15 animals were selected. Next, a 60 minute intravenous glucose tolerance test (ivGTT) (0.25 g glucose/kg body weight) was performed following an overnight fasting to select animals with glucose intolerance (glucose AUC>8500 mg/dLxmin). Blood samples were collected 5, 10, 20, 40, and 60 minutes after glucose administration, and all procedures were performed under ketamine anesthesia. Ten out of the 15 hyperglycemic animals satisfied the glucose intolerance criteria and these monkeys were used for the study described below and also depicted in FIG. 9.

Methods and Results 5 days prior to H4H1327P administration, an oral glucose tolerance test (oGTT) (1.75 g glucose/kg body weight) was performed following an overnight fasting to establish baseline oGTT data. Blood samples were collected 15, 30, 60, 90, 120, and 180 min after glucose administration for blood glucose measurements, and no anesthesia was used throughout the procedure. 2 days prior to H4H1327P administration, 30 and 60 minutes post-meal blood glucose levels following an overnight fasting were measured to establish baseline post-meal blood glucose values. No anesthesia was used throughout the procedure.

The 10 selected monkeys were divided into two groups of 5 animals each based on the baseline fasting blood glucose levels and ivGTT and oGTT glucose AUC data. The monkeys were fasted overnight, and fasting blood was collected for serum chemistry immediately prior to H4H1327P administration. The animals received an intravenous bolus administration of H4H1327P at 20 mg/kg (n=5) or 5 mg/kg (n=5). Immediately after H4H1327P dosing, ivGTT was performed to determine the onset of H4H1327P action. Blood samples were collected 5, 10, 20, 40, and 60 min after glucose administration for blood glucose and plasma insulin, and glucagon measurements. All procedures were performed under ketamine anesthesia.

Two animals treated with 20 mg/kg H4H1327P and one animal treated with 5 mg/kg H4H1327P were excluded from the study analysis as they exhibited Time 0 (fasting) blood glucose levels equal to or below 90 mg/dL. Since Time 0 glucose levels of ivGTT immediately after H4H1327P administration were measured prior to H4H1327P dosing, and there was slight reduction in group mean Time 0 glucose levels in comparison to the levels during baseline ivGTT, % of Time 0 glucose level was calculated for glucose level of each time point for each animal. Using the % glucose, area under the curve (AUC) from the beginning to the end of ivGTT and fractional (20 or 40 min interval) glucose AUC were calculated for each animal. Mean±SEM of % glucose AUC and fractional % glucose AUC were calculated for each group. Mean % glucose AUC of the entire 60 min and mean fractional % glucose AUC of 20-60 and 40-60 min intervals were significantly reduced in monkeys treated with 5 mg/kg H4H1327P (Table 17). Mean fractional % glucose AUC of 40-60 min interval was significantly reduced in monkeys treated with 20 mg/kg H4H1327P (Table 16). Mean±SEM of plasma insulin and glucagon levels were calculated for each group for each blood collection time points. No significant changes in mean plasma insulin or glucagon levels were observed during the ivGTT, in comparison to the levels during baseline ivGTT, in both treatment groups. Statistical analysis was performed with Prism software (version 5). To assess the significance before and after H4H1327P administration, paired T-test was used. *: p<0.05, : p<0.01, *: p<0.001, ****: p<0.000.

Two days after H4H1327P administration, 30 and 60 minutes post-meal blood glucose levels following an overnight fast were measured. Mean±SEM of 30 and 60 minutes post-meal glucose levels were calculated for each group. Significant reduction in mean 60 min post-meal blood glucose level was detected in monkeys treated with 20 mg/kg H4H1327P (Table 18). Although the data did not reach statistical significance, trends toward reduction in 30 min post-meal blood glucose levels in monkeys treated with 20 mg/kg H4H1327P (Table 18) and 30 and 60 min post-meal blood glucose levels in monkeys treated with 5 mg/kg H4H1327P were observed (Table 19). It is important to note that the greatest post-meal glucose reductions were seen in animals with the highest glucose at baseline. The lowest post-meal blood glucose recorded was 86 mg/dL in an animal treated with 20 mg/kg H4H1327P. Statistical analysis was performed with Prism software (version 5). To assess the significance before and after H4H1327P administration, paired T-test was used. *: p<0.05, : p<0.01, *: p<0.001, ****: p<0.0001.

Four days after H4H1327P administration, oGTT was performed in conscious animals following an overnight fasting. Blood samples were collected 15, 30, 60, 90, 120, and 180 min after glucose administration for blood glucose measurements. Mean±SEM of fasting blood glucose levels were calculated for each group. Significant (p=0.0045) and near-significant (p=0.052) reductions in mean fasting blood glucose levels were observed in monkeys treated with 20 and 5 mg/kg H4H1327P, respectively (Table 20). The lowest fasting blood glucose recorded was 67 mg/dL in an animal treated with 20 mg/kg H4H1327P. Mean±SEM of blood glucose levels at each time point during oGTT were calculated for each group. Blood glucose AUC during oGTT was calculated for each animal, and mean±SEM of blood glucose AUC were calculated for each group. A significant reduction in mean glucose AUC was observed in monkeys treated with 20 mg/kg H4H1327P. Trends toward reductions in glucose AUC were observed in monkeys treated with 5 mg/kg H4H1327P (Table 21). Statistical analysis was performed with Prism software (version 5). To assess the significance before and after H4H1327P administration, paired T-test was used. *: p<0.05, : p<0.01, *: p<0.001, ****: p<0.0001.

Seven days after H4H1327P administration, ivGTT was performed in ketamine anesthetized animals following an overnight fast. Blood samples were collected 5, 10, 20, 40, and 60 min after glucose administration for blood glucose and plasma insulin and glucagon measurements. Mean±SEM of fasting blood glucose levels were calculated for each group. A significant reduction in mean fasting blood glucose level was observed in monkeys treated with 20 mg/kg H4H1327P (Table 22). The lowest fasting blood glucose recorded was 79 mg/dL in an animal treated with 20 mg/kg H4H1327P. Mean±SEM of blood glucose levels at each time point during ivGTT were calculated for each group. Blood glucose AUC during ivGTT was calculated for each animal, and mean±SEM of blood glucose AUC were calculated for each group.

Seven days post H4H1327P administration, a significant reduction in mean glucose AUC was observed in monkeys treated with 20 mg/kg H4H1327P (Table 23). Non-significant reductions in glucose AUC were also observed in monkeys treated with 5 mg/kg H4H1327P (Table 23). Mean±SEM of plasma insulin and glucagon levels at each blood sampling time point were calculated for each group. Although they did not reach statistical significance, in both treatment groups, circulating insulin levels appear to be elevated after glucose administration 7 days post H4H1327P administration in comparison to the levels during baseline ivGTT. In both treatment groups, mean glucagon levels were significantly increased before and after glucose administration 7 days post H4H1327P administration in comparison to baseline. Immediately prior to glucose administration, fasting blood was collected for serum chemistry. Mean±SEM of each serum parameter were calculated for each group. Significant increases in serum triglyceride levels were observed in monkeys treated with 20 mg/kg H4H1327P 7 days post H4H1327P administration. Trends toward an increase in serum triglyceride levels were also observed in monkeys treated with 5 mg/kg H4H1327P 7 days post H4H1327P administration in comparison to baseline.

Statistical analysis was performed with Prism software (version 5). To assess the significance before and after H4H1327P administration, paired T-test was used. *: $p<0.05$, : $p<0.01$, *: $p<0.001$, ****: $p<0.0001$.

TABLE 16

Fractional % Glucose AUC (%*min), 20 mg/kg (n = 3)

|  | Baseline | | Day 0 | |
| --- | --- | --- | --- | --- |
|  | Mean | SEM | Mean | SEM |
| 0-20 min | 2752 | 57 | 2715 | 205 |
| 20-40 min | 2500 | 72 | 2388 | 149 |
| 40-60 min | 2240 | 71 | 2009 | 103 |

TABLE 17

Fractional % Glucose AUC (%*min), 5 mg/kg (n = 4)

|  | Baseline | | Day 0 | |
| --- | --- | --- | --- | --- |
|  | Mean | SEM | Mean | SEM |
| 0-20 min | 2814 | 249 | 2797 | 275 |
| 20-40 min | 2467 | 100 | 2329 | 137 |
| 40-60 min | 2199 | 62 | 1898 | 72 |

TABLE 18

30 and 60 min Post-meal Glucose (mg/dL), 20 mg/kg (n = 5)

|  | Baseline | | Day 2 | |
| --- | --- | --- | --- | --- |
|  | Mean | SEM | Mean | SEM |
| 30 min | 208 | 44 | 112 | 12 |
| 60 min | 235 | 44 | 131 | 12 |

TABLE 19

30 and 60 min Post-meal Glucose (mg/dL), 5 mg/kg (n = 4)

|  | Baseline | | Day 2 | |
| --- | --- | --- | --- | --- |
|  | Mean | SEM | Mean | SEM |
| 30 min | 240 | 41 | 166 | 23 |
| 60 min | 287 | 53 | 199 | 30 |

TABLE 20

Fasting Glucose Before oGTT (mg/dL)

|  | Baseline | | Day 4 | |
| --- | --- | --- | --- | --- |
|  | Mean | SEM | Mean | SEM |
| 20 mg/kg REGN1193 | 153 | 16 | 83 | 9 |
| 5 mg/kg REGN1193 | 178 | 35 | 131 | 22 |

TABLE 21 oGTT Glucose AUC (mg/dL*min)

|  | Baseline | | Day 4 | |
| --- | --- | --- | --- | --- |
|  | Mean | SEM | Mean | SEM |
| 20 mg/kg REGN1193 | 38181 | 6302 | 24597 | 3461 |
| 5 mg/kg REGN1193 | 40656 | 7656 | 34044 | 5056 |

TABLE 22

Fasting Glucose Before ivGTT (mg/dL)

|  | Baseline | | Day 7 | |
| --- | --- | --- | --- | --- |
|  | Mean | SEM | Mean | SEM |
| 20 mg/kg REGN1193 | 167 | 22 | 86 | 4 |
| 5 mg/kg REGN1193 | 176 | 28 | 150 | 27 |

TABLE 23 ivGTT Glucose AUC (mg/dL*min)

|  | Baseline | | Day 7 | |
| --- | --- | --- | --- | --- |
|  | Mean | SEM | Mean | SEM |
| 20 mg/kg REGN1193 | 12633 | 1481 | 8112 | 385 |
| 5 mg/kg REGN1193 | 13472 | 1871 | 12100 | 1613 |

Summary of In Vivo Pharmacology Data in the Cynomolgus Monkey Study with H4H1327P The objective of this study was to evaluate the effects of H4H1327P on blood glucose levels, glucose tolerance, and other serum parameters, when administered at two different doses in cynomolgus monkeys with spontaneous diabetes.

In animals treated with 20 mg/kg H4H1327P, 46% (p=0.04) and 50% (p=0.01) reductions in fasting blood glucose levels were observed 4 and 7 days post H4H1327P administration, respectively, in comparison to baseline values. Post-meal blood glucose levels measured 2 days post H4H1327P administration were 46% (p=0.03) reduced. During an ivGTT performed immediately after H4H1327P administration, % glucose AUC of 40-60 min interval was reduced by 10% (p=0.02), suggesting the onset of H4H1327P action on blood glucose is ~1 h. At oGTT and ivGTT performed 4 and 7 days after H4H1327P administration, 35% (p=0.01) and 36% (p=0.02) reductions in glucose AUC were observed, respectively.

In animals treated with 5 mg/kg H4H1327P, 26% (p=0.052) and 15% (p=0.2) reductions in fasting blood glucose levels were observed 4 and 7 days post H4H1327P administration, respectively, in comparison to baseline values. Post-meal blood glucose levels measured 2 days post H4H1327P administration were 30% (p=0.08) reduced. During an ivGTT performed immediately after H4H1327P administration, % glucose AUC of 40-60 min interval was reduced by 14% (p=0.01). At oGTT and ivGTT performed 4 and 7 days after H4H1327P administration, non-significant 20% (p=0.2) and 10% (p=0.3) reductions in glucose AUC were observed, respectively. In both dose groups, there were no changes in plasma insulin or glucagon concentrations during ivGTT performed before and immediately after H4H1327P administration. However, trends toward increases in plasma insulin levels after glucose administration were observed during the ivGTT performed 7 days post H4H1327P administration, suggesting elevated glucose induced insulin secretion in H4H1327P treated animals. 7 days post H4H1327P administration, plasma glucagon levels were increased by 5.5-(p<0.001) and 4-fold (p<0.001) with 20 and 5 mg/kg H4H1327P, respectively. 1.8-(p=0.043) and 4.3-fold (p=0.119) increases in serum triglyceride levels were also observed in monkeys treated with 20 and 5 mg/kg H4H1327P. It is of note that in no case did fasting blood glucose levels of H4H1327P treated animals fall below normal monkey range (50-70 mg/dL).

In conclusion, the anti-GCGR mAb H4H1327P reduced blood glucose levels and improved glucose tolerance in monkeys with spontaneous diabetes in a dose-dependent manner, demonstrating that H4H1327P has glucose-lowering efficacy in non-human primates. H4H1327P onset of action was observed within 1 hour after IV bolus administration of the mAb, supporting the use of H4H1327P for short-term indications. H4H1327P also increased glucose induced insulin secretion without changes in LDL cholesterol levels 7 days after drug administration. No differences in body weight were detected in all animals after H4H1327P administration and throughout the study. These data in diabetic monkeys support the clinical use of H4H1327P as a glucose lowering agent for both long and short term indications.

Example 15

A Proposed Clinical Study to Determine the Effect of an Anti-GCGR Antibody on Stress Hyperglycemia in Human Patients Two distinct programs are proposed for testing the effects of an anti-GCGR antibody in patients with stress hyperglycemia. These programs are as follows:

Study Plan A) a development program for H4H1327P in stress hyperglycemia for critical patients in the ICU using composite metabolic endpoints as a surrogate endpoint and a post approval morbidity and mortality outcome study.

Study Plan B) a clinical development program in patients with stress hyperglycemia in non-critical ICU patients with metabolic endpoints, insulin dose, and resource utilization as key endpoints. Morbidity and mortality will be designated as other secondary endpoints since this population is at a low risk for death.
Position According to 2012 guidelines, stress hyperglycemia in the diabetic and non-diabetic hospitalized patient is considered a medical condition requiring prompt therapeutic intervention (Korytkowski M, McDonnell M E, Umpierrez G E, Zonszein J, J Clin Endocrinol Metab. (2012), January; 97(1):27A-8A; Umpierrez G E, Hellman R, Korytkowski M T, Kosiborod M, Maynard G A, Montori V M, et al. J Clin Endocrinol Metab. (2012) January; 97(1):16-38). Hyperglucagonemia plays a key role in stress hyperglycemia by increasing hepatic glucose output and thus counterbalancing the glucose lowering effect of insulin. In ICU and non-ICU patients, elevated blood glucose levels are associated with increased morbidity and mortality (Baker E H, Janaway C H, Philips B J, Brennan A L, Baines D L, Wood D M, et al., Thorax, (2006), April; 61(4): 284-9), Umpierrez G E, Isaacs S D, Bazargan N, You X, Thaler L M, Kitabchi A E, J Clin Endocrinol Metab. (2002), March 87(3):978-82; McAlister F A, Majumdar S R, Blitz S, Rowe B H, Romney J, Marrie T J, Diabetes Care. (2005), April 28(4):810-5). Eighty percent of ICU patients with stress hyperglycemia have no history of diabetes before hospital admission. Patients with new hyperglycemia (induced or diagnosed at the time of hospitalization) have significantly higher in-hospital mortality rate and worse functional outcome than patients with a prior history of diabetes and subjects with normoglycemia. Current treatment for stress hyperglycemia is insulin, which is quite effective in controlling glucose but tight glucose control is often associated with episodes of hypoglycemia. Therefore, an unmet medical need exists for effective treatment with no associated hypoglycemia irrespective of the underlying critical illness. We hypothesize that for the treatment of stress hyperglycemia, H4H1327P in combination with insulin compared to insulin alone will be effective in decreasing morbidity and mortality through improved metabolic control, an indication that addresses an unmet medical need.

A Phase 2 dose ranging study is planned in ICU patients (randomized 1:1 to H4H1327P or placebo) to assess the efficacy and safety of H4H1327P. For the Phase 3, a study is planned whereby-patients will be randomized 1:1 to H4H1327P (treatment arms will be added depending on the number of doses) or placebo using a surrogate primary endpoint that would most likely predict morbidity and mortality benefit. Mackenzie et. al. demonstrated that the combination of metrics of central tendency (average glucose), variability of glucose (excursions) and hypoglycemia (minimum glucose) are better predictors of mortality than the individual metrics alone (Table 24), (MacKenzie, I M et al., Intensive Care Med. (2011), March, 37(3):435-43) In addition, (1) the interaction between glucose concentrations and outcome may arise from these three independent and synergistic domains, namely, central tendency, variability, and minimum value; (2) the relationship may be non-linear and specific to both patient population (medical or surgical) and domain; (3) the relationship has a dose-response component meaning the longer the metric is met, the better the outcome.

Thus, the goal for therapy with an anti-GCGR antibody, as described herein, in combination with insulin, is to maintain a constant level of glucose control in the target range, devoid of glucose swings, both high and low.

TABLE 24

Mean and variability of glucose and hypoglycemia are better predictors of mortality than individual metrics alone

| | Low risk Death % | High risk Death % | OR (95% CI) Low vs High |
|---|---|---|---|
| 1. Average glucose | 11.4 | 22.5 | 2.0 (1.6, 2.5) |
| 2. Glucose excursions | 9.9 | 19.4 | 2.2 (1.8, 2.7) |
| 3. Minimum glucose | 9.3 | 20.5 | 2.5 (2.0, 3.1) |
| 1 + 2 | 7.8 | 23.4 | 3.6 (2.6, 4.9) |
| 1 + 3 | 6.2 | 24.2 | 4.8 (3.4, 6.8) |
| 2 + 3 | 7.6 | 24.2 | 3.9 (2.9, 5.2) |
| 1 + 2 + 3 | 6.0 | 27.8 | 6.0 (3.9, 9.2) |

We propose that the study in critically ill patients with stress hyperglycemia, assuming it meets key endpoints, would be followed by a post-approval morbidity and mortality outcome study in ICU patients.
B. Study Plan B.
Study Population Under Consideration The population under consideration is patients 18-65 years of age with non-critical illness (not in the ICU) and stress hyperglycemia and who have a blood glucose>180 mg/dL and expected length of hospital stay that exceeds 5 days are eligible for the proposed study. Patients will not be in the ICU but may be admitted to monitored (e.g., telemetry or diabetes unit) beds or general ward beds. Patients may or may not have a history of diabetes mellitus. Patients admitted for DKA and HHS are not eligible for this study.

Study Design Under Consideration

The design under consideration is a randomized double blind placebo controlled parallel study in patients with non-critical stress hyperglycemia. Subjects will be randomized to H4H1327P or placebo, in addition to their usual care. Based on the current practice guidelines, providers are expected to treat blood glucoses of 140-180 mg/dL with basal/bolus insulin. They are also expected to reassess patients and treatment plans when blood glucose <100 mg/dL and to alter treatment when blood glucose <70 mg/dL. In this trial, patients will be randomized if their blood glucose is >180 mg/dL to receive insulin (basal/bolus) and H4H1327P or insulin (basal/bolus) and placebo for H4H1327P (number of arms and doses to be determined) in a 1:1 ratio). The insulin will not be blinded. Patients will be followed until discharge. The primary endpoints of metabolic control and insulin dose will be collected for 72 hr after randomization.

What is claimed is:

1. A method of reducing the amount and/or dosage of insulin necessary to lower blood glucose levels to a normal range in a patient at risk for developing stress hyperglycemia, or in a patient suffering from stress hyperglycemia, the method comprising administering, concomitantly with insulin, an effective amount of a glucagon receptor (GCGR) antagonist, wherein the GCGR antagonist is an isolated human monoclonal antibody that binds specifically to the glucagon receptor.

2. The method of claim 1, wherein the amount and/or dosage of insulin may be reduced by about 30% to about 95% when administered concomitantly with a GCGR antagonist, wherein the antagonist is an isolated human monoclonal antibody that binds specifically to the glucagon receptor.

3. The method of claim 2, wherein the amount and/or dosage of insulin may be reduced by about 90% when administered concomitantly with a GCGR antagonist, wherein the antagonist is an isolated human monoclonal antibody that binds specifically to the glucagon receptor.

4. The method of claim 1, wherein the GCGR antagonist is an isolated human monoclonal antibody comprising the complementarity determining regions (CDRs) of a heavy chain variable region (HCVR), wherein the HCVR has an amino acid sequence selected from the group consisting of SEQ ID NOs: 2, 18, 34, 50, 66, 70, 86, 90, 106, 110, 126, 130 and 146; and the CDRs of a light chain variable region (LCVR), wherein the LCVR has an amino acid sequence selected from the group consisting of SEQ ID NOs: 10, 26, 42, 58, 68, 78, 88, 98, 108, 118, 128, 138 and 148.

5. The method of claim 4, wherein the isolated human monoclonal antibody or antigen-binding fragment thereof comprises a heavy chain variable region (HCVR) having an amino acid sequence selected from the group consisting of SEQ ID NO: 2, 18, 34, 50, 66, 70, 86, 90, 106, 110, 126, 130 and 146.

6. The method of claim 4, wherein the isolated human monoclonal antibody or antigen-binding fragment thereof comprises a light chain variable region (LCVR) having an amino acid sequence selected from the group consisting of SEQ ID NO: 10, 26, 42, 58, 68, 78, 88, 98, 108, 118, 128, 138 and 148.

7. The method of claim 4, wherein the isolated human monoclonal antibody or antigen-binding fragment thereof comprises: (a) a HCVR having an amino acid sequence selected from the group consisting of SEQ ID NO: 2, 18, 34, 50, 66, 70, 86, 90, 106, 110, 126, 130 and 146; and (b) a LCVR having an amino acid sequence selected from the group consisting of SEQ ID NO: 10, 26, 42, 58, 68, 78, 88, 98, 108, 118, 128, 138 and 148.

8. The method of claim 4, wherein the isolated human monoclonal antibody or antigen-binding fragment thereof comprises:
   (a) a HCDR1 domain having an amino acid sequence selected from the group consisting of SEQ ID NO: 4, 20, 36, 52, 72, 92, 112 and 132;
   (b) a HCDR2 domain having an amino acid sequence selected from the group consisting of SEQ ID NO: 6, 22, 38, 54, 74, 94, 114 and 134;
   (c) a HCDR3 domain having an amino acid sequence selected from the group consisting of SEQ ID NOs: 8, 24, 40, 56, 76, 96, 116 and 136;
   (d) a LCDR1 domain having an amino acid sequence selected from the group consisting of SEQ ID NO: 12, 28, 44, 60, 80, 100, 120 and 140;
   (e) a LCDR2 domain having an amino acid sequence selected from the group consisting of SEQ ID NO: 14, 30, 46, 62, 82, 102, 122 and 142; and
   (f) a LCDR3 domain having an amino acid sequence selected from the group consisting of SEQ ID NO: 16, 32, 48, 64, 84, 104, 124 and 144.

9. The method of claim 4, wherein the isolated human monoclonal antibody or antigen-binding fragment comprises a HCVR/LCVR sequence pair selected from the group consisting of SEQ ID NO: 2/10, 18/26, 34/42, 50/58, 66/68, 70/78, 86/88, 90/98, 106/108, 110/118, 126/128, 130/138, and 146/148.

10. The method of claim 4, wherein the isolated human monoclonal antibody comprises a HCVR/LCVR amino acid sequence pair as set forth in SEQ ID NOs: 86/88.

\* \* \* \* \*